(12) United States Patent  
Christensen et al.

(10) Patent No.: US 8,871,747 B2  
(45) Date of Patent: Oct. 28, 2014

(54) UREA AND THIOUREA DERIVATIVES

(75) Inventors: Mette Knak Christensen, Holte (DK); Fredrik Bjorkling, Helsingborg (SE)

(73) Assignee: Topotarget A/S, Copenhagen (DK)

( * ) Notice: Subject to any disclaimer, the term of this patent is extended or adjusted under 35 U.S.C. 154(b) by 306 days.

(21) Appl. No.: 13/060,789

(22) PCT Filed: Aug. 31, 2009

(86) PCT No.: PCT/EP2009/061200  
§ 371 (c)(1),  
(2), (4) Date: Sep. 27, 2011

(87) PCT Pub. No.: WO2010/023307  
PCT Pub. Date: Mar. 4, 2010

(65) Prior Publication Data  
US 2012/0010172 A1    Jan. 12, 2012

Related U.S. Application Data

(60) Provisional application No. 61/092,838, filed on Aug. 29, 2008.

(51) Int. Cl.
| | |
|---|---|
| A61K 31/675 | (2006.01) |
| C07D 253/07 | (2006.01) |
| C07D 213/40 | (2006.01) |
| C07D 231/40 | (2006.01) |
| C07D 413/12 | (2006.01) |
| C07D 213/75 | (2006.01) |
| C07D 239/42 | (2006.01) |

(52) U.S. Cl.  
CPC ............ *C07D 213/75* (2013.01); *C07D 253/07* (2013.01); *C07D 213/40* (2013.01); *C07D 231/40* (2013.01); *C07D 413/12* (2013.01); *C07D 239/42* (2013.01)  
USPC .......................................................... 514/90

(58) Field of Classification Search  
USPC ........ 514/90, 580, 585, 588, 595; 564/17, 26, 564/47, 56  
See application file for complete search history.

(56) References Cited

U.S. PATENT DOCUMENTS

| 4,921,856 | A | 5/1990 | Schickaneder et al. | |
|---|---|---|---|---|
| 2002/0156102 | A1* | 10/2002 | Duncia et al. ................ | 514/331 |
| 2007/0238746 | A1 | 10/2007 | Brandl et al. | |
| 2007/0259855 | A1 | 11/2007 | Maier et al. | |

FOREIGN PATENT DOCUMENTS

| DE | 2614189 | | 10/1977 |
|---|---|---|---|
| EP | 0283040 | | 9/1988 |
| EP | 0283041 | | 9/1988 |
| EP | 0304534 | A1 | 3/1989 |
| EP | 1522540 | | 4/2005 |
| EP | 1816124 | | 8/2007 |
| EP | 2098231 | | 9/2009 |
| JP | 64-068360 | A | 3/1989 |
| WO | WO97/48397 | | 12/1997 |
| WO | WO97/48695 | | 12/1997 |
| WO | WO97/48696 | | 12/1997 |
| WO | WO98/54144 | | 12/1998 |
| WO | WO99/31060 | | 6/1999 |
| WO | WO99/31063 | | 6/1999 |
| WO | WO99/31087 | | 6/1999 |
| WO | WO00/50399 | | 8/2000 |
| WO | WO00/61559 | | 10/2000 |
| WO | WO00/61561 | | 10/2000 |
| WO | WO02/42265 | | 5/2002 |
| WO | WO02/094265 | | 11/2002 |
| WO | WO02/094813 | | 11/2002 |
| WO | WO03/080054 | | 10/2003 |
| WO | WO03/097601 | | 11/2003 |
| WO | WO03/097602 | | 11/2003 |
| WO | WO2004/028539 | | 4/2004 |
| WO | WO2006/066584 | | 6/2006 |

(Continued)

OTHER PUBLICATIONS

Binderup et al., "EB1627: a soluble prodrug of the potent anticancer cyanoguanidine CHS828," *Biorg Med Chem Lett*, vol. 15, pp. 2491-2494 (2005).

(Continued)

*Primary Examiner* — Wu-Cheng Winston Shen  
*Assistant Examiner* — Christopher R Stone  
(74) *Attorney, Agent, or Firm* — McDermott Will & Emery LLP

(57) ABSTRACT

The present application discloses compounds of formula (I) wherein X is =O, =S, =NH, =NOH and =NO-Me; A is —C(=O)—, —S(=O)$_2$—, —C(=S)— and P(=O)(R$^5$)—; B is, —O—, —(CH$_2$)$_{3\text{-}6}$—, and O—(CH$_2$)$_{2\text{-}5}$—; D is, —O—, —CR$^7$R$^8$— and —NR$^9$; m is 0-12, n is 0-12, m+n is 1-20; p is 0-4; R$^1$ is opt. sub. heteroaryl; and pharmaceutically acceptable salts thereof, and prodrugs thereof. The application also discloses the compound for use as a medicament for the treatment of a disease or a condition caused by an elevated level of nicotinamide phosphoribosyltransferase (NAMPRT), e.g. inflammatory and tissue repair disorders; dermatosis; autoimmune diseases, Alzheimer's disease, stroke, atherosclerosis, restenosis, diabetes, glomerulonephritis, cancer, cachexia, inflammation associated with infection and certain viral infections, including Acquired Immune Deficiency Syndrome (AIDS), adult respiratory distress syndrome, ataxia telengiectasia.

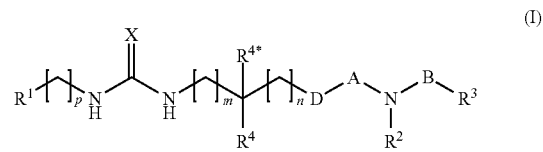

(I)

8 Claims, 1 Drawing Sheet

(56) References Cited

FOREIGN PATENT DOCUMENTS

| WO | WO2007/068473 | 6/2007 |
|---|---|---|
| WO | WO2007/134827 | 11/2007 |
| WO | WO2008/000421 | 1/2008 |
| WO | WO2008/025857 | 3/2008 |
| WO | WO2009/026446 | 2/2009 |
| WO | WO2009/086835 | 7/2009 |

OTHER PUBLICATIONS

Chemical Abstract Service, Scientific Exchange Product List, CAS Registry No. 360571-032-0, 1 page (2011).

Fitzmaurice et al., "Carboxylate binding in polar solvents using pyridylguanidinium salts," *Organic & Biomolecular Chemistry*, vol. 5, No. 11, pp. 1706-1714 (2007).

Hjarnaa et al., "CHS 828, a Novel Pyridyl Cynanoguanidine with Potent Antitumor Activity in Vitro and in Vivo," *Cancer Research*, vol. 59, pp. 5751-5757 (1999).

Wang et al. "Synthesis and Peptydyl-Prolyl Isomerase Inhibitory Activity of Quinoxalines as Ligands of Cyclophilin A," *Chem. Pharm. Bull.*, vol. 54, No. 3, pp. 372-376 (2006).

Bellstein—CrossFire Bellstein Database, Registry No. 8287323, XP-002555440, 2009 (2 pages).

Chemical Abstract Service, Scientific Exchange Product List, XP-002555441, Acession No. 2023092884 CHEMCATS, 1 page (2009).

Hasmann et al., "FK866, a Highly Specific Noncompetitive Inhibitor of Nicotinamide Phosphoribosyltransferase, Represents a Novel Mechanism for Induction of Tumor Cell Apoptosis," *Cancer Research*, vol. 63, pp. 7436-7442 (2003).

D. Glaβ et al., 4-(4-Guanidinobenzoyl)-2-imidazolones and Related Compounds: Phosphodiesterase Inhibitors and Novel Cardiotonics with Combined Histamine H2 Receptor Agonist and PDE III Inhibitor Activity, Archiv der Pharmazie (Weinheim, Germany), 1995, 328(10), pp. 709-719.

Office Action, mailed Feb. 4, 2014, which issued during the prosecution of Japanese Patent Application No. 2011-524406, which corresponds to the present application.

\* cited by examiner

UREA AND THIOUREA DERIVATIVES

CROSS REFERENCE TO PRIOR APPLICATIONS

This application is a U.S. National Phase application under 35 U.S.C. §371 of International Application No. PCT/EP2009/061200, filed on Aug. 31, 2009 and claims benefit of priority to U.S. Provisional Patent Application No. 61/092,838, filed on Aug. 29, 2008. The International Application was published in English on Mar. 4, 2010 as WO 2010/023307 A1 under PCT Article 21(2). All of these applications are herein incorporated by reference.

FIELD OF THE INVENTION

This invention relates to urea and thiourea derivatives, which are useful for the inhibiting of the enzyme nicotinamide phosphoribosyltransferase (NAMPRT), and to medical use of such derivatives.

BACKGROUND OF THE INVENTION

Inhibition of the enzyme nicotinamide phosphoribosyltransferase (NAMPRT) results in the inhibition of NF-kB, the inhibition of NF-kB being a result of the lowering of cellular concentrations of nicotinamide adenine dinucleotide (NAD) (Beauparlant et al. (2007) AACR-NCI-EORTC International Conference on Molecular Targets and Cancer Therapeutics, 2007 Oct. 22-26 Abstract nr A82; and Roulson et al. (2007) AACR-NCI-EORTC International Conference on Molecular Targets and Cancer Therapeutics, 2007 Oct. 22-26 Abstract nr A81). Tumor cells have elevated expression of NAMPRT and a high rate of NAD turnover due to high ADP-ribosylation activity required for DNA repair, genome stability, and telomere maintenance making them more susceptible to NAMPRT inhibition than normal cells. This also provides a rationale for the use of compounds of this invention in combination with DNA damaging agents for future clinical trials.

The pathways of NAD biosynthesis are shown in FIG. 1.

NAMPRT is involved in the biosynthesis of nicotinamide adenine dinucleotide (NAD) and NAD(P). NAD can be synthesized in mammalian cells by three different pathways starting either from tryptophan via quinolinic acid, from nicotinic acid (niacin) or from nicotinamide (niacinamide).

Quinolinic acid reacts with phosphoribosyl pyrophosphate to form niacin mononucletide (dNAM) using the enzyme quinolinic acid phosphoribosyltransferase ❸ which is found in liver kidney and brain.

Nicotinic acid (niacin) reacts with PRPP to form niacin mononucleotide (dNAM), using the enzyme niacin phosphoribosyltransferase ❷ which is widely distributed in various tissues.

Nicotinamide (niacinamide) reacts with PRPP to give niacinamide mononucleotide (NAM) using the enzyme nicotinamide phosphoribosyltransferase (NAMPRT) ❶ which is also widely distributed in various tissues.

The subsequent addition of adenosine monophosphate to the mononucleotides results in the formation of the corresponding dinucleotides: Niacin mononucleotide and niacinamide mononucleotide react with ATP to form niacin adenine dinucleotide (dNAD) and niacinamide adenine dinucleotide (NAD) respectively. Both reactions, although they take place on different pathways, are catalysed by the same enzyme, NAD pyrophosphorylase ❹.

A further amidation step is required to convert niacin adenine dinucleotide (dNAD) to niacinamide adeinine dinucleotide (NAD) The enzyme which catalyses this reaction is NAD synthetase ❺. NAD is the immediate precursor of niacinamide adenine dinucleotide phosphate (NAD(P)) The reaction is catalysed by NAD kinase. For details see, e.g., Cory J. G. Purine and pyrimidine nucleotide metabolism In: Textbook of Biochemistry and Clinical Correlations 3$^{rd}$ edition ed. Devlin, T, Wiley, Brisbane 1992, pp 529-574.

Normal cells can typically utilize both precursors niacin and niacinamide for NAD(P) synthesis, and in many cases additionally tryptophan or its metabolites. Accordingly, murine glial cells use niacin, niacinamide and quinolinic acid (Grant et al. (1998) J. Neurochem. 70: 1759-1763). Human lymphocytes use niacin and niacinamide (Carson et al. (1987) J. Immunol. 138: 1904-1907; Berger et al. (1982) Exp. Cell Res. 137; 79-88). Rat liver cells use niacin, niacinamide and tryptophan (Yamada et al. (1983) Int. J. Vit. Nutr. Res. 53: 184-1291; Shin et al. (1995) Int. J. Vit. Nutr. Res. 65: 143-146; Dietrich (1971) Methods Enzymol. 18B; 144-149). Human erythrocytes use niacin and niacinamide (Rocchigiani et al. (1991) Purine and pyrimidine metabolism in man VII Part B ed. Harkness et al. Plenum Press New York pp 337-3490). Leukocytes of guinea pigs use niacin (Flechner et al. (1970), Life Science 9: 153-162).

NAD(P) is involved in a variety of biochemical reactions which are vital to the cell and have therefore been thoroughly investigated. The role of NAD(P) in the development and growth of tumours has also been studied. It has been found that many tumour cells utilize niacinamide for cellular NAD(P) synthesis. It is thought that niacin and tryptophan which constitute alternative precursors in many normal cell types cannot be utilized in tumour cells, or at least not to an extent sufficient for cell survival. Selective inhibition of an enzyme which is only on the niacinamide pathway (such as NAMPRT) would constitute a method for the selection of tumour specific drugs. This is exemplified by the NAMPRT inhibitors which have been in clinical trials as anti cancer agents, namely FK866/APO866, (see Hasmann and Schemainda, Cancer Res 63(21):7463-7442.), CHS828/GMX1778 and its prodrug EB1627/GMX1777 (see Hjarnaa et al, Cancer Research 59; 5751-5757; Binderup et al, Bioorg Med Chem Lett 15:2491-2494). Further inhibitors of NAMPRT are found in WO 2006/066584, WO 2003/097602, WO 2003/097601, WO 2002/094813, WO 2002/094265, WO 2002/042265, WO 2000/61561, WO2000/61559, WO 1997/048695, WO 1997/048696, WO 1997/048397, WO 1999/031063, WO 1999/031060 and WO 1999/031087.

It is known that various derivatives of urea, substituted in a specific manner have pharmacologically useful properties. In particular, certain derivatives are known to possess therapeutic activity. All of these compounds however are structurally dissimilar from the compounds of the present invention.

Compounds comprising urea moieties are described in the following publications:

Budd et al. (WO 2007/068473) describe the following compound as an inhibitor of PI-3-kinase.:

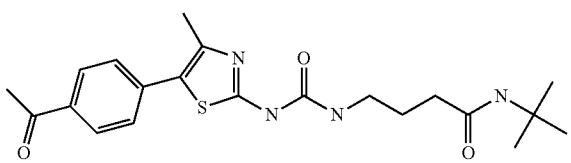 [SMILES: CC(=O)c1ccc(-c2sc(NC(=O)NCCCC(=O)NC(C)(C)C)nc2C)cc1]

Bruce et al. (WO 2008/000421) describe compounds of the following structure as inhibitors of PI-3 kinase delta:

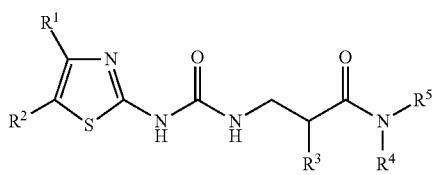

Further inhibitors of PI-3 kinase are described by Budd et al. (WO 2007/134827):

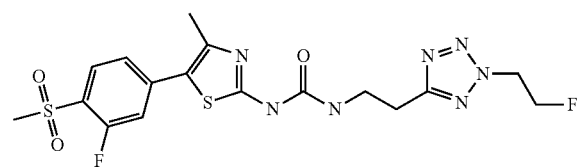 [SMILES: Cc1nc(NC(=O)NCCc2nnn(CCF)n2)sc1-c1ccc(S(C)(=O)=O)c(F)c1]

Weber et al. (DE 2614189) describe compounds of the following generic structure as analgesic agents.

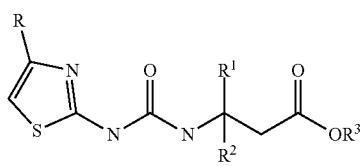

Ashwell et al. (2009) [WO 2009/026446] describe the following compounds as inhibitors of histone deacetylases:

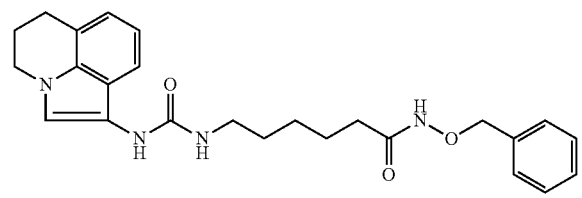

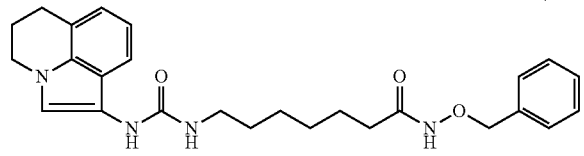

The following compounds are listed in the Ambinter Stock Screening Collection of 20 Feb. 2009:

(CAS no. 1010932-67-8)

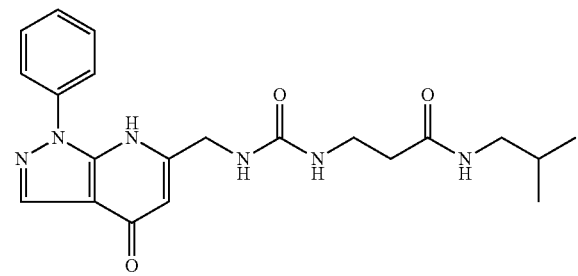

(CAS no. 1100188-32-6)

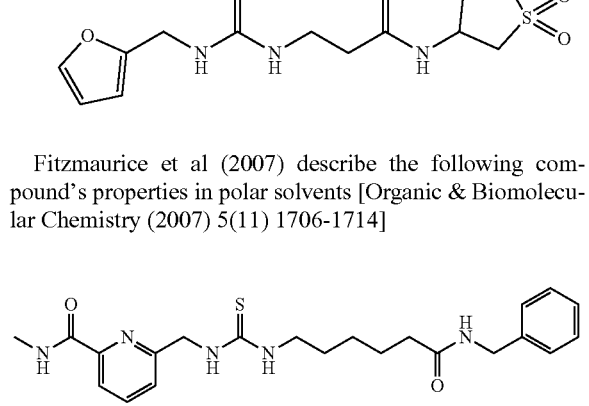

Fitzmaurice et al (2007) describe the following compound's properties in polar solvents [Organic & Biomolecular Chemistry (2007) 5(11) 1706-1714]

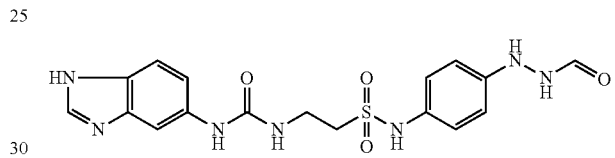

Morio et al (1998) [European patent application EP283040] describe the following compound for use in photographic material:

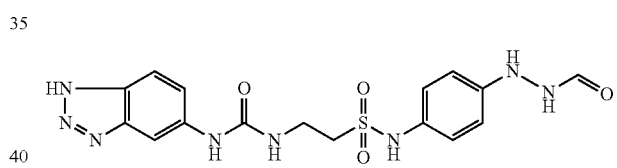

Inoue et al (1998) [EP 283041] describe the following compound for use in photographic material:

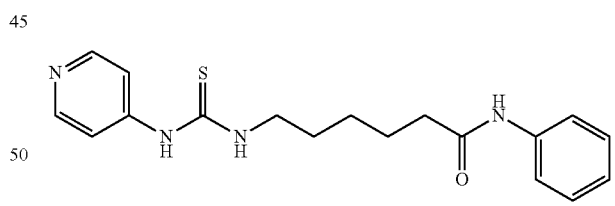

Schoue et al (1998) [WO 1998/54144] describe the following compound as a potential inhibitor of cell proliferation:

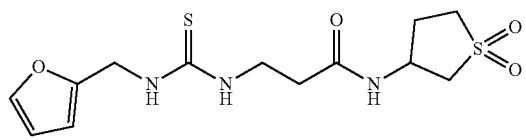

BRIEF DESCRIPTION OF THE INVENTION

It is believed that the novel compounds of the invention are acting on the enzyme nicotinamide phosphoribosyltransferase (NAMPRT), and that the down-stream inhibition of NF-kB is the result of the lowering of cellular concentrations of nicotinamide adenine dinucleotide (NAD).

Hence, the present invention provides compounds of the general formula (I) according to claim 1, and the utilization of these compounds in medicine.

Inhibitors of the enzyme NAMPRT may be used in the treatment of cancer (WO 97/48696), to cause immunosuppression (WO 97/48397), for the treatment of diseases involving angiogenesis (WO 2003/80054), for the treatment of rheumatoid arthritis or septic shock (WO 2008/025857), or for the prophylaxis and treatment of ischaemia (EP 08102310.3 (unpublished application)).

DETAILED DESCRIPTION OF THE INVENTION

Compounds of the Invention

Figure 1:
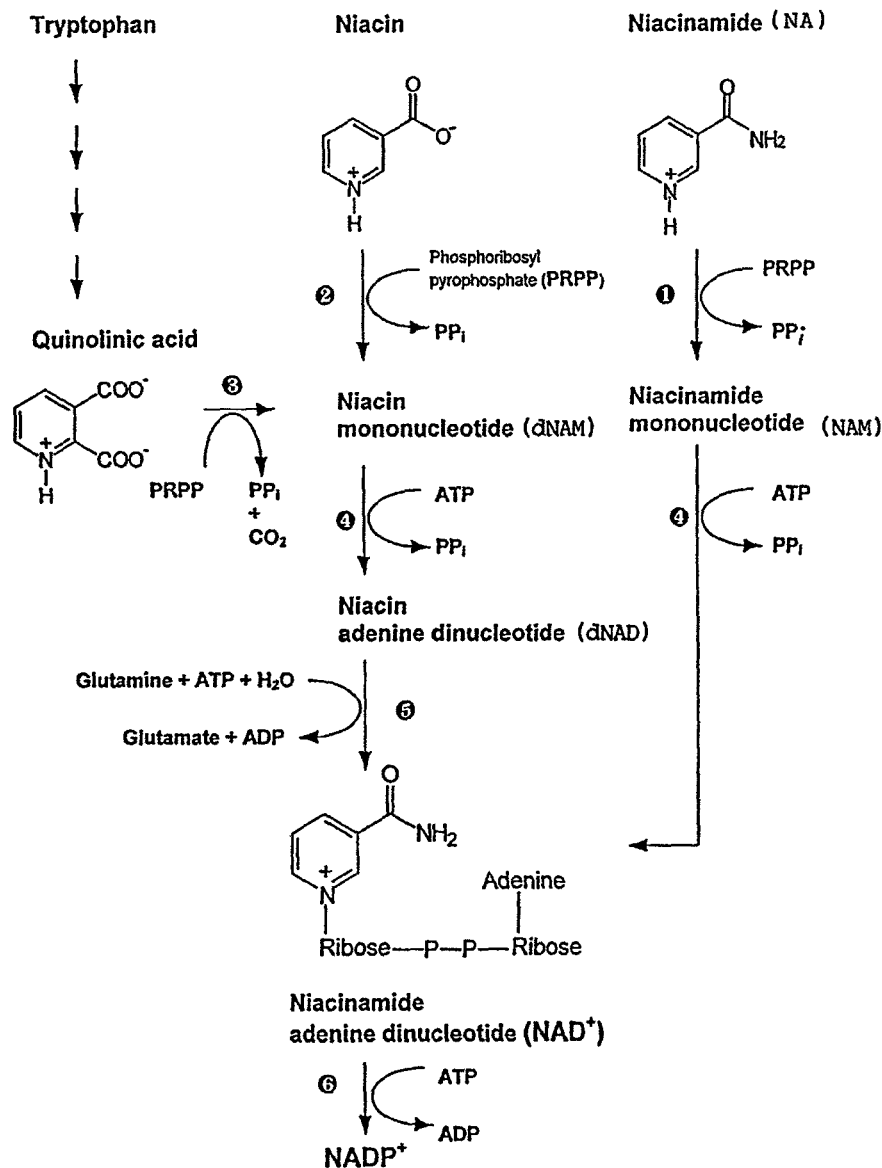
FIG. 1 illustrates the pathway of NAD biosynthesis (from Biedermann E. et al, WO 00/50399).

The present invention i.a. relates to particular urea and thiourea derivatives which are useful for the inhibition of the enzyme nicotinamide phosphoribosyltransferase (NAM-PRT).

The present invention relates to compounds of the formula (I)

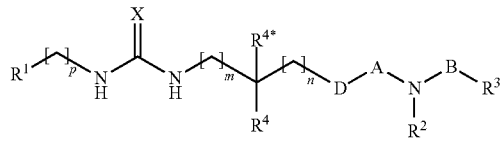

wherein
X is selected from =O, =S, =NH, =NOH and =NO-Me;
A is selected from —C(=O)—, —S(=O)$_2$—, —C(=S)— and —P(=O)(R$^5$)—, wherein R$^5$ is selected from C$_{1-6}$-alkyl, C$_{1-6}$-alkoxy and hydroxy;
B is selected from a single bond, —(CH$_2$)$_{3-6}$—, —O—, and —O—(CH$_2$)$_{2-5}$—;
D is selected from a single bond, —O—, —CR$^7$R$^8$— and —NR$^9$, wherein R$^7$, R$^8$ and R$^9$ are independently selected from hydrogen, optionally substituted C$_{1-12}$-alkyl, optionally substituted C$_{1-12}$-alkenyl, optionally substituted aryl, optionally substituted heterocyclyl, and optionally substituted heteroaryl;
m is an integer of 0-12 and n is an integer of 0-12, wherein the sum m+n is 1-20;
p is an integer of 0-4;
R$^1$ is selected from optionally substituted heteroaryl;
R$^2$ is selected from hydrogen, optionally substituted C$_{1-12}$-alkyl, optionally substituted C$_{3-12}$-cycloalkyl, —[CH$_2$CH$_2$O]$_{1-10}$-(optionally substituted C$_{1-6}$-alkyl), optionally substituted C$_{1-12}$-alkenyl, optionally substituted aryl, optionally substituted heterocyclyl, and optionally substituted heteroaryl; and R$^3$ is selected from optionally substituted C$_{1-12}$-alkyl, optionally substituted C$_{3-12}$-cycloalkyl, —[CH$_2$CH$_2$O]$_{1-10}$-(optionally substituted C$_{1-6}$-alkyl), optionally substituted C$_{1-12}$-alkenyl, optionally substituted aryl, optionally substituted heterocyclyl, and optionally substituted heteroaryl; or R$^2$ and R$^3$ together with the intervening atoms (i.e. —N—B—) form an optionally substituted N-containing heterocyclic or heteroaromatic ring;
each of R$^4$ and R$^{4*}$ is independently selected from hydrogen, optionally substituted C$_{1-12}$-alkyl and optionally substituted C$_{1-12}$-alkenyl;
with the proviso that R$^1$ is not optionally substituted thiazol-2-yl when p is 0;
and with the proviso that the compound is not phenyl-NH—C(=O)—(CH$_2$)$_5$—NH—C(=S)—NH—(4-pyridyl); and pharmaceutically acceptable salts thereof, and prodrugs thereof.

In particular,
when X is =O and A is —SO$_2$—, then B is —O— or —(CH$_2$)$_{3-6}$— or —O—(CH$_2$)$_{2-5}$—; and
when X is =O, A is —C(=O)—, and p=0, then B is —O— or —(CH$_2$)$_{3-6}$— or —O—(CH$_2$)$_{2-5}$—; and
when X is =O, A is —C(=O)—, and p=0, then R$^1$ is not

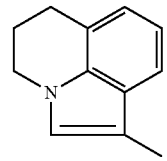

when X is =O, A is —C(=O)—, and p=1-4, then R$^1$ is not

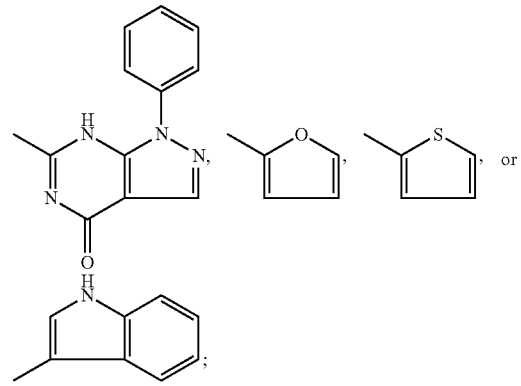

and
when X is =S, A is —C(=O)—, and p=1-4, then R$^3$ is not benzyl or

Definitions

In the present context, the terms "C$_{1-12}$-alkyl" and "C$_{1-6}$-alkyl" are intended to mean a linear, cyclic or branched hydrocarbon group having 1 to 12 carbon atoms and 1 to 6 carbon atoms, respectively, such as methyl, ethyl, propyl, iso-propyl, cyclopropyl, butyl, iso-butyl, tert-butyl, cyclobutyl, pentyl, cyclopentyl, hexyl, and cyclohexyl.

Although the term "C$_{3-12}$-cycloalkyl" is encompassed by the term "C$_{1-12}$-alkyl", it refers specifically to the mono- and bicyclic counterparts, including alkyl groups having exo-cyclic atoms, e.g. cyclohexyl-methyl.

Similarly, the terms "C$_{2-12}$-alkenyl" and "C$_{2-6}$-alkenyl" are intended to cover linear, cyclic or branched hydrocarbon groups having 2 to 12 carbon atoms and 2 to 6 carbon atoms, respectively, and comprising (at least) one unsaturated bond. Examples of alkenyl groups are vinyl, allyl, butenyl, pentenyl, hexenyl, heptenyl, octenyl, heptadecaenyl. Preferred examples of alkenyl are vinyl, allyl, butenyl, especially allyl.

Although the term "C$_{3-12}$-cycloalkenyl" is encompassed by the term "C$_{2-12}$-alkenyl", it refers specifically to the mono- and bicyclic counterparts, including alkenyl groups having exo-cyclic atoms, e.g. cyclohexenyl-methyl and cyclohexyl-allyl.

In the present context, i.e. in connection with the terms "alkyl", "cycloalkyl", "alkoxy", "alkenyl", "cycloalkenyl" and the like, the term "optionally substituted" is intended to mean that the group in question may be substituted one or several times, preferably 1-3 times, with group(s) selected from hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo (forming a keto or aldehyde functionality), $C_{1-6}$-alkoxycarbonyl, $C_{1-6}$-alkylcarbonyl, formyl, aryl, aryloxy, arylamino, arylcarbonyl, aryloxycarbonyl, arylcarbonyloxy, arylaminocarbonyl, arylcarbonylamino, heteroaryl, heteroaryloxy, heteroarylamino, heteroarylcarbonyl, heteroaryloxycarbonyl, heteroarylcarbonyloxy, heteroarylaminocarbonyl, heteroarylcarbonylamino, heterocyclyl, heterocyclyloxy, heterocyclylamino, heterocyclylcarbonyl, heterocyclyloxycarbonyl, heterocyclylcarbonyloxy, heterocyclylaminocarbonyl, heterocyclylcarbonylamino, amino, mono- and di($C_{1-6}$-alkyl)amino, —N($C_{1-4}$-alkyl)$_3^+$, carbamoyl, mono- and di($C_{1-6}$-alkyl)aminocarbonyl, $C_{1-6}$-alkylcarbonylamino, cyano, guanidino, carbamido, $C_{1-6}$-alkyl-sulphonyl-amino, aryl-sulphonyl-amino, heteroaryl-sulphonyl-amino, $C_{1-6}$-alkanoyloxy, $C_{1-6}$-alkyl-sulphonyl, $C_{1-6}$-alkyl-sulphinyl, $C_{1-6}$-alkylsulphonyloxy, nitro, $C_{1-6}$-alkylthio, and halogen, where any aryl, heteroaryl and heterocyclyl may be substituted as specifically described below for aryl, heteroaryl and heterocyclyl, and any alkyl, alkoxy, and the like, representing substituents may be substituted with hydroxy, $C_{1-6}$-alkoxy, amino, mono- and di($C_{1-6}$-alkyl)amino, carboxy, $C_{1-6}$-alkylcarbonylamino, $C_{1-6}$-alkylaminocarbonyl, or halogen(s).

Typically, the substituents are selected from hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo (forming a keto or aldehyde functionality), $C_{1-6}$-alkylcarbonyl, formyl, aryl, aryloxy, arylamino, arylcarbonyl, heteroaryl, heteroaryloxy, heteroarylamino, heteroarylcarbonyl, heterocyclyl, heterocyclyloxy, heterocyclylamino, heterocyclylcarbonyl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, guanidino, carbamido, $C_{1-6}$-alkyl-sulphonyl-amino, $C_{1-6}$-alkyl-sulphonyl, $C_{1-6}$-alkyl-sulphinyl, $C_{1-6}$-alkylthio, halogen, where any aryl, heteroaryl and heterocyclyl may be substituted as specifically described below for aryl, heteroaryl and heterocyclyl.

In some embodiments, substituents are selected from hydroxy, $C_{1-6}$-alkoxy, amino, mono- and di($C_{1-6}$-alkyl) amino, carboxy, $C_{1-6}$-alkylcarbonylamino, $C_{1-6}$-alkylaminocarbonyl, or halogen.

The term "halogen" includes fluoro, chloro, bromo, and iodo.

In the present context, the term "aryl" is intended to mean a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl and xanthenyl, among which phenyl is a preferred example.

The term "heteroaryl" is intended to mean a fully or partially aromatic carbocyclic ring or ring system where one or more of the carbon atoms have been replaced with heteroatoms, e.g. nitrogen (=N— or —NH—), sulphur, and/or oxygen atoms. Examples of such heteroaryl groups are oxazolyl, isoxazolyl, thiazolyl, isothiazolyl, pyrrolyl, imidazolyl, pyrazolyl, pyridinyl, pyrimidinyl, pyrazinyl, pyridazinyl, triazinyl, coumaryl, furanyl, thienyl, quinolyl, benzothiazolyl, benzotriazolyl, benzodiazolyl, benzooxozolyl, phthalazinyl, phthalanyl, triazolyl, tetrazolyl, isoquinolyl, acridinyl, carbazolyl, dibenzazepinyl, indolyl, benzopyrazolyl, phenoxazonyl. Particularly interesting heteroaryl groups are benzimidazolyl, oxazolyl, isoxazolyl, thiazolyl, isothiazolyl, pyrrolyl, imidazolyl, pyrazolyl, pyridinyl, pyrimidinyl, pyrazinyl, pyridazinyl, furyl, thienyl, quinolyl, triazolyl, tetrazolyl, isoquinolyl, indolyl in particular benzimidazolyl, pyrrolyl, imidazolyl, pyridinyl, pyrimidinyl, furyl, thienyl, quinolyl, tetrazolyl, and isoquinolyl.

The term "heterocyclyl" is intended to mean a non-aromatic carbocyclic ring or ring system where one or more of the carbon atoms have been replaced with heteroatoms, e.g. nitrogen (=N— or —NH—), sulphur, and/or oxygen atoms. Examples of such heterocyclyl groups (named according to the rings) are imidazolidine, piperazine, hexahydropyridazine, hexahydropyrimidine, diazepane, diazocane, pyrrolidine, piperidine, azepane, azocane, aziridine, azirine, azetidine, pyrroline, tropane, oxazinane (morpholine), azepine, dihydroazepine, tetrahydroazepine, and hexahydroazepine, oxazolane, oxazepane, oxazocane, thiazolane, thiazinane, thiazepane, thiazocane, oxazetane, diazetane, thiazetane, tetrahydrofuran, tetrahydropyran, oxepane, tetrahydrothiophene, tetrahydrothiopyrane, thiepane, dithiane, dithiepane, dioxane, dioxepane, oxathiane, oxathiepane. The most interesting examples are tetrahydrofuran, imidazolidine, piperazine, hexahydropyridazine, hexahydropyrimidine, diazepane, diazocane, pyrrolidine, piperidine, azepane, azocane, azetidine, tropane, oxazinane (morpholine), oxazolane, oxazepane, thiazolane, thiazinane, and thiazepane, in particular tetrahydrofuran, imidazolidine, piperazine, hexahydropyridazine, hexahydropyrimidine, diazepane, pyrrolidine, piperidine, azepane, oxazinane (morpholine), and thiazinane.

The term "N-containing heterocyclic or heteroaromatic ring" are intended to encompass those mentioned under "heterocyclyl" and "heteroaryl", respectively, which include one or more heteroatoms, at least one of which begin a nitrogen atom. Examples hereof are piperazine, isoxazole, isoxazolidine, and morpholine, etc.

The term "N,O-containing heterocyclic or heteroaromatic ring" are intended to encompass those mentioned under "heterocyclyl" and "heteroaryl", respectively, which include two or more heteroatoms, two of which being neighbouring nitrogen and oxygen atoms. Examples hereof are isoxazole, isoxazolidine, morpholine, etc.

In the present context, i.e. in connection with the terms "aryl", "heteroaryl", "heterocyclyl", "N,O-containing heterocyclic or heteroaromatic ring" and the like (e.g. "aryloxy", "heteroarylcarbonyl", etc.), the term "optionally substituted" is intended to mean that the group in question may be substituted one or several times, preferably 1-5 times, in particular 1-3 times, with group(s) selected from hydroxy (which when present in an enol system may be represented in the tautomeric keto form), $C_{1-6}$-alkyl, $C_{1-6}$-alkoxy, $C_{2-6}$-alkenyloxy, oxo (which may be represented in the tautomeric enol form), oxide (only relevant as the N-oxide), carboxy, $C_{1-6}$-alkoxycarbonyl, $C_{1-6}$-alkylcarbonyl, formyl, aryl, aryloxy, arylamino, aryloxycarbonyl, arylcarbonyl, heteroaryl, heteroarylamino, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkanoyloxy, $C_{1-6}$-alkyl-sulphonyl-amino, aryl-sulphonyl-amino, heteroaryl-sulphonyl-amino, $C_{1-6}$-alkyl-suphonyl, $C_{1-6}$-alkyl-sulphinyl, $C_{1-6}$-alkylsulphonyloxy, nitro, sulphanyl, amino, amino-sulfonyl, mono- and di($C_{1-6}$-alkyl)amino-sulfonyl, dihalogen-$C_{1-4}$- alkyl, trihalogen-$C_{1-4}$-alkyl, halogen, where aryl and heteroaryl representing substituents may be substituted 1-3 times with $C_{1-4}$-alkyl, $C_{1-4}$-alkoxy, nitro, cyano, amino or halogen, and any alkyl, alkoxy, and the like, representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonylamino, or guanidino.

Typically, the substituents are selected from hydroxy, $C_{1-6}$-alkyl, $C_{1-6}$-alkoxy, oxo (which may be represented in the tautomeric enol form), carboxy, $C_{1-6}$-alkylcarbonyl, formyl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, $C_{1-6}$-alkylcarbonylamino, guanidino, carbamido, $C_{1-6}$-alkyl-sulphonyl-amino, aryl-sulphonyl-amino, heteroaryl-sulphonyl-amino, $C_{1-6}$-alkyl-suphonyl, $C_{1-6}$-alkyl-sulphinyl, $C_{1-6}$-alkylsulphonyloxy, sulphanyl, amino, amino-sulfonyl, mono- and di($C_{1-6}$-alkyl)amino-sulfonyl or halogen, where any alkyl, alkoxy and the like, representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, or guanidino. In some embodiments, the substituents are selected from $C_{1-6}$-alkyl, $C_{1-6}$-alkoxy, amino, mono- and di($C_{1-6}$-alkyl)amino, sulphanyl, carboxy or halogen, where any alkyl, alkoxy and the like, representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, or guanidino.

Groups (e.g. $R^2$ and $R^3$) including $C_{3-12}$-cycloalkyl, $C_{3-12}$-cycloalkenyl and/or aryl as at least a part of the substituent are said to include "a carbocyclic ring".

Groups (e.g. $R^2$ and $R^3$) including heterocyclyl or heteroaryl as at least a part of the substituent are said to include "a heterocyclic ring" and "a heteroaromatic ring", respectively.

The term "pharmaceutically acceptable salts" is intended to include acid addition salts and basic salts. Illustrative examples of acid addition salts are pharmaceutically acceptable salts formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of such inorganic salts are those with hydrochloric, hydrobromic, sulfuric, sulfamic, phosphoric, and nitric acids. Examples of basic salts are salts where the (remaining) counter ion is selected from alkali metals, such as sodium and potassium, alkaline earth metals, such as calcium, and ammonium ions ($^+N(R)_3R'$, where R and R' independently designates optionally substituted $C_{1-6}$-alkyl, optionally substituted $C_{2-6}$-alkenyl, optionally substituted aryl, or optionally substituted heteroaryl). Pharmaceutically acceptable salts are, e.g., those described in Remington's Pharmaceutical Sciences, 17. Ed. Alfonso R. Gennaro (Ed.), Mack Publishing Company, Easton, Pa., U.S.A., 1985 and more recent editions and in Encyclopedia of Pharmaceutical Technology. Thus, the term "an acid addition salt or a basic salt thereof" used herein is intended to comprise such salts. Furthermore, the compounds as well as any intermediates or starting materials may also be present in hydrate form.

The term "prodrug" used herein is intended to mean a compound which—upon exposure to physiological conditions—will liberate a derivative said compound which then will be able to exhibit the desired biological action. Typical examples are labile esters (i.e. a latent hydroxyl group or a latent acid group).

Moreover, it should be understood that the compounds may be present as racemic mixtures or the individual stereoisomers such as enantiomers or diastereomers. The present invention encompasses each and every of such possible stereoisomers (e.g. enantiomers and diastereomers) as well as racemates and mixtures enriched with respect to one of the possible stereoisomers.

Embodiments

In one primary embodiment, X is selected from =O and =S.

In one embodiment hereof, X is =O and B is —O—. Within one important variant of this embodiment A is —S(=O)$_2$—. Within another important variant of this embodiment, A is —C(=O)—.

In another embodiment X is =S and B is —O—. Within one important variant of this embodiment A is —S(=O)$_2$—. Within another important variant of this embodiment, A is —C(=O)—.

In another embodiment, X is selected from =O and =S and B is a single bond. Within one important variant of this embodiment A is —S(=O)$_2$—. Within another important variant of this embodiment, A is —C(=O)—.

In another embodiment, B is selected from —(CH$_2$)$_{3-6}$— and —O—(CF$_{12}$)$_{2-5}$—, preferably from —(CH$_2$)$_{3-4}$— and —O—(CH$_2$)$_{1-3}$—. Within this embodiment, X is preferably selected from =O and =S.

In the above embodiments, D is preferably selected from a single bond, —O—, and —NR$^9$. More particular, D is a single bond.

With respect to R$^1$, this substituent is preferably selected from optionally substituted pyridin-4-yl, optionally substituted pyrimidin-4-yl, optionally substituted 1,2,4-triazin-3-yl, optionally substituted isoxazol-4-yl, optionally substituted pyrazin-2-yl, and optionally substituted picolyl; in particular from pyridin-4-yl, pyrimidin-4-yl, 1,2,4-triazin-3-yl, 3,5-isoxazol-4-yl, pyrazin-2-yl, and picolyl.

The distance between R$^1$ and the urea moiety is determined by p. p is an integer of 0-4, but is preferably 0-2, in particular 0.

In a currently particularly interesting embodiment, p is 0 and R$^1$ is pyridin-4-yl.

In another particularly interesting embodiment, p is 1.

The length of the spacer element is defined by m and n. Preferably, m is an integer of 0-10 and n is an integer of 0-10, wherein the sum m+n is 1-12; in particular m is an integer of 1-8 and n is an integer of 0-3, wherein the sum m+n is 3-8. In a currently most preferred variant, m is an integer of 2-8 and n is 0.

It appears that—besides D, A and B—R$^2$ and R$^3$ (and in part also R$^4$ and R$^{4*}$) play an important role for the efficacy of the compounds of the invention. Hence, in one particularly interesting embodiment, at least one of R$^2$ and R$^3$ includes a carbocyclic ring, heterocyclic ring or a heteroaromatic ring, or R$^2$ and R$^3$ together with the intervening atoms form an optionally substituted N-containing heterocyclic or heteroaromatic ring. In a particularly interesting variant of this embodiment R$^2$ is carbocyclic, in particular is cyclohexyl. In interesting alternative embodiments, R$^2$ not hydrogen.

In one variant hereof, R$^2$ and R$^3$ together with the intervening atoms form an optionally substituted N,O-containing heterocyclic or heteroaromatic ring.

Moreover, $R^4$ is preferably selected from hydrogen, $C_{1-6}$-alkyl and optionally substituted benzyl and $R^{4*}$ is hydrogen. More particular, $R^4$ and $R^{4*}$ are preferably both hydrogen.

In one currently particularly relevant embodiment,
X is selected from =O and =S;
A is selected from —C(=O)— and —S(=O)$_2$—;
B is —O—;
D is selected from a single bond, —O—, and —NR$^9$;
m is an integer of 2-8 and n is 0;
p is an integer of 0-2;
$R^2$ is selected from hydrogen, optionally substituted $C_{3-12}$-cycloalkyl, —[CH$_2$CH$_2$O]$_{1-10}$-(optionally substituted $C_{1-6}$-alkyl), —(CH$_2$)$_{0-2}$-(optionally substituted aryl), —(CH$_2$)$_{0-2}$-(optionally substituted heteroaryl) and —(CH$_2$)$_{0-2}$-(optionally substituted heterocyclyl);
$R^3$ is selected from optionally substituted $C_{3-12}$-cycloalkyl, —[CH$_2$CH$_2$O]$_{1-10}$-(optionally substituted $C_{1-6}$-alkyl), optionally substituted $C_{1-12}$-alkenyl, optionally substituted aryl, optionally substituted heterocyclyl, and optionally substituted heteroaryl;
$R^4$ is selected from hydrogen, optionally substituted $C_{3-12}$-cycloalkyl, —(CH$_2$)$_{0-2}$-(optionally substituted aryl), —(CH$_2$)$_{0-2}$-(optionally substituted heteroaryl) and —(CH$_2$)$_{0-2}$-(optionally substituted heterocyclyl); and
$R^{4*}$ is hydrogen.

In another particularly relevant embodiment,
X is selected from =O and =S;
A is selected from —C(=O)— and —S(=O)$_2$—;
B is selected from —(CH$_2$)$_{3-6}$— and —O—(CH$_2$)$_{2-5}$—, preferably from —(CH$_2$)$_{3-4}$— and —O—(CH$_2$)$_{1-3}$—;
D is selected from a single bond, —O—, and —NR$^9$;
m is an integer of 2-8 and n is 0;
p is an integer of 0-2;
$R^2$ is selected from hydrogen, optionally substituted $C_{3-12}$-cycloalkyl, —[CH$_2$CH$_2$O]$_{1-10}$-(optionally substituted $C_{1-6}$-alkyl), —(CH$_2$)$_{0-2}$-(optionally substituted aryl), —(CH$_2$)$_{0-2}$-(optionally substituted heteroaryl) and —(CH$_2$)$_{0-2}$-(optionally substituted heterocyclyl);
$R^3$ is selected from optionally substituted $C_{3-12}$-cycloalkyl, —[CH$_2$CH$_2$O]$_{1-10}$-(optionally substituted $C_{1-6}$-alkyl), optionally substituted $C_{1-12}$-alkenyl, optionally substituted aryl, optionally substituted heterocyclyl, and optionally substituted heteroaryl;
$R^4$ is selected from hydrogen, optionally substituted $C_{3-12}$-cycloalkyl, —(CH$_2$)$_{0-2}$-(optionally substituted aryl), —(CH$_2$)$_{0-2}$-(optionally substituted heteroaryl) and —(CH$_2$)$_{0-2}$-(optionally substituted heterocyclyl); and
$R^{4*}$ is hydrogen.

This being said, currently most interesting compounds are those selected from compounds 1001-1101 described in the following:

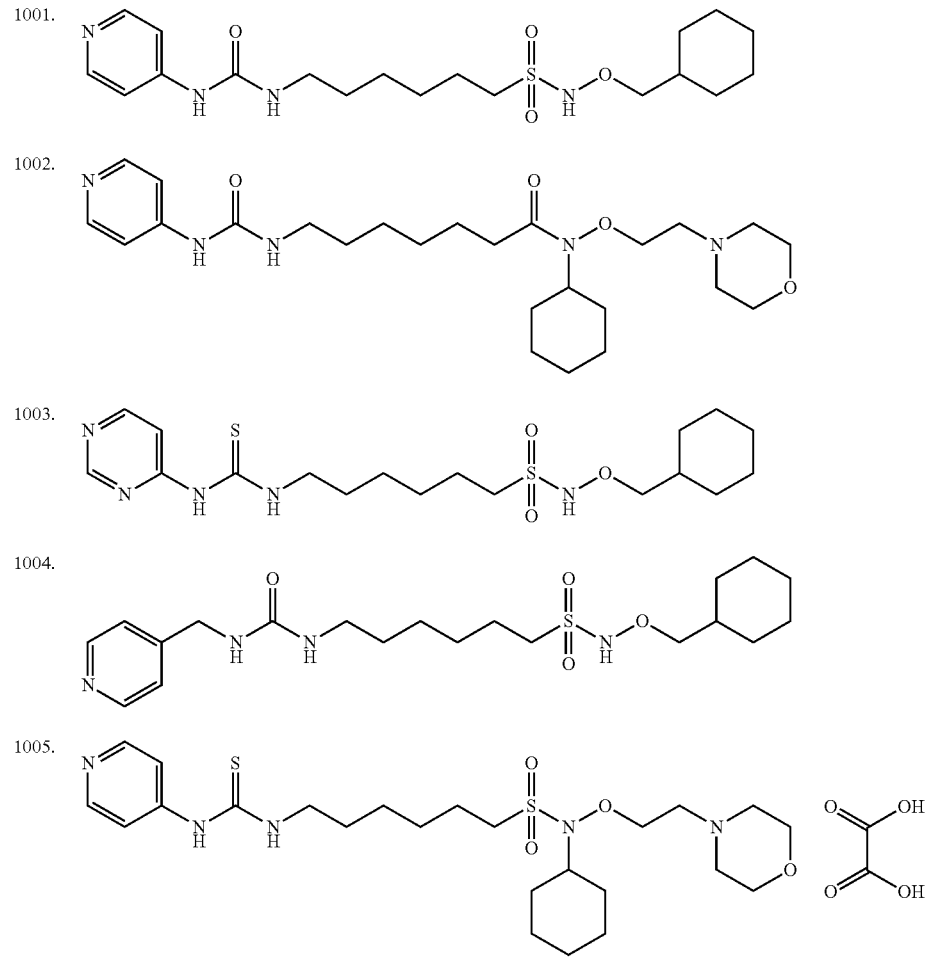

| Compound | Structure |
|---|---|
| 1001. | 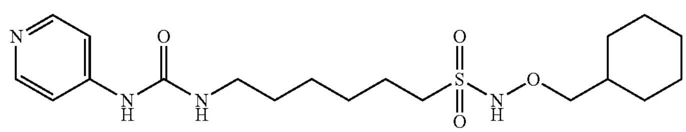 [SMILES: O=C(NCCCCCCS(=O)(=O)NOCC1CCCCC1)Nc1ccncc1] |
| 1002. | 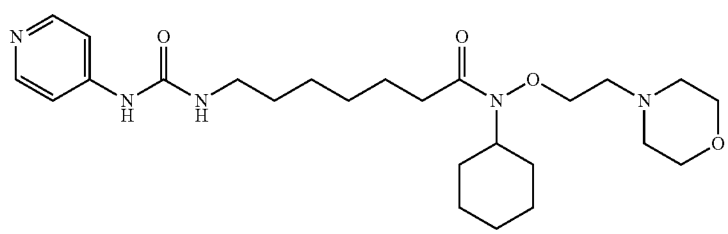 [SMILES: O=C(NCCCCCCC(=O)N(OCCN1CCOCC1)C1CCCCC1)Nc1ccncc1] |
| 1003. | 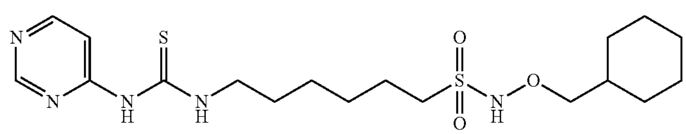 |
| 1004. | 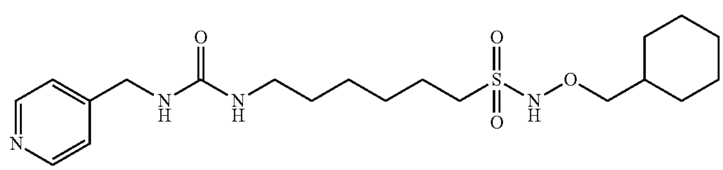 [SMILES: O=C(NCCCCCCS(=O)(=O)NOCC1CCCCC1)NCc1ccncc1] |
| 1005. | 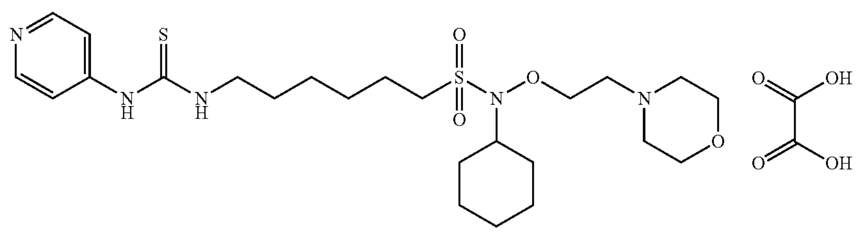 |

| Compound | Structure |
|---|---|
| 1006. | 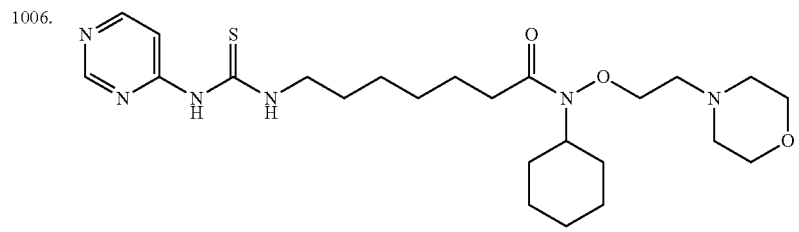 |
| 1007. | 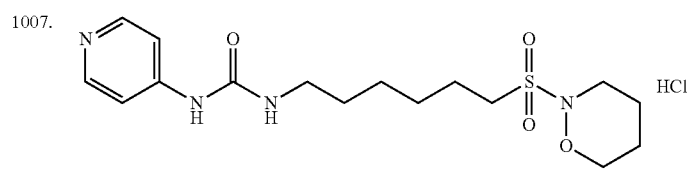 |
| 1008. | 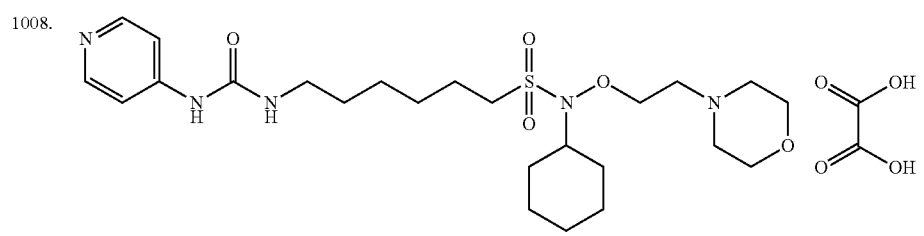 |
| 1009. | 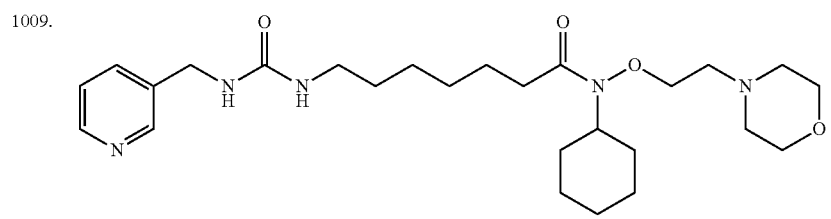 |
| 1010. | 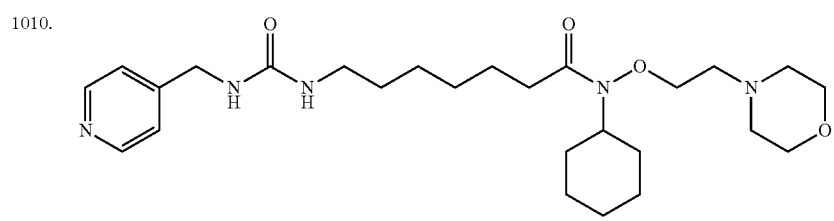 |
| 1011. | 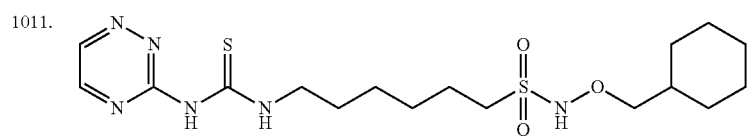 |
| 1012. | 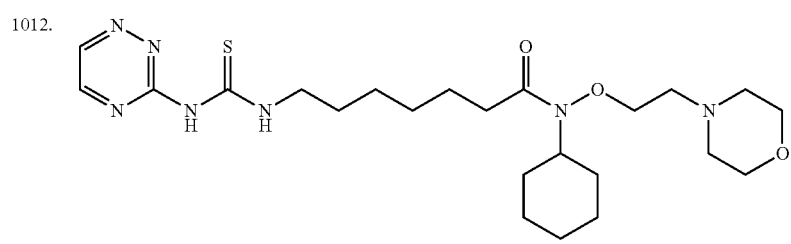 |

-continued
| Compound | Structure |
|---|---|
| 1013. | 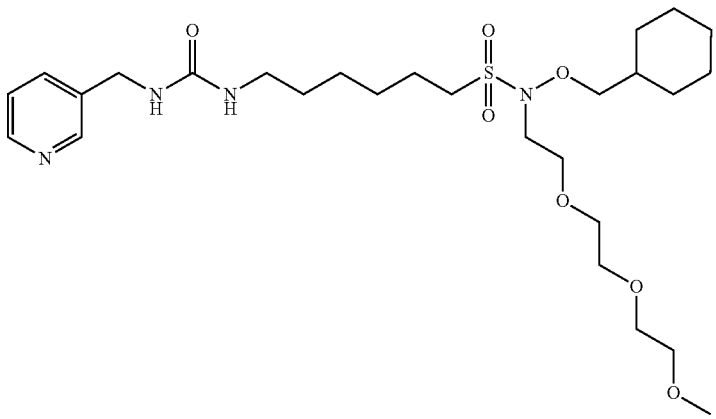 |
| 1014. | 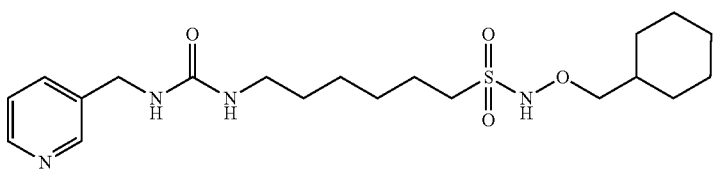 [SMILES: O=C(NCCCCCCS(=O)(=O)NOCC1CCCCC1)NCc1cccnc1] |
| 1015. | 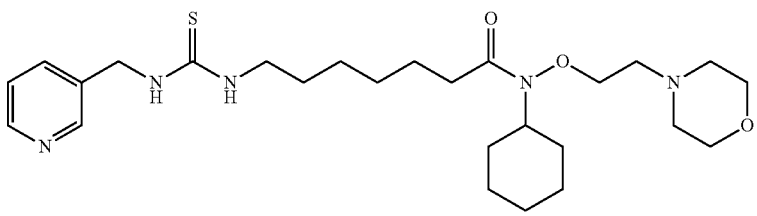 |
| 1016. | 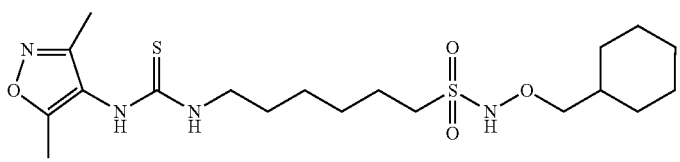 [SMILES: Cc1noc(C)c1NC(=S)NCCCCCCS(=O)(=O)NOCC1CCCCC1] |
| 1017. | 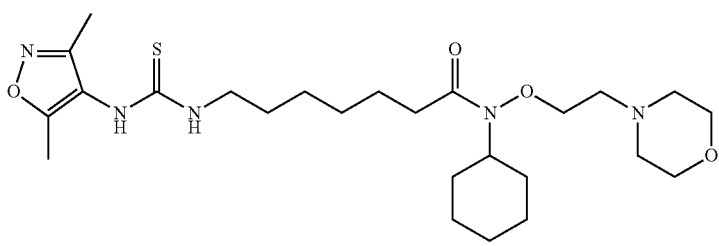 [SMILES: Cc1noc(C)c1NC(=S)NCCCCCCC(=O)N(OCCN1CCOCC1)C1CCCCC1] |
| 1018. | 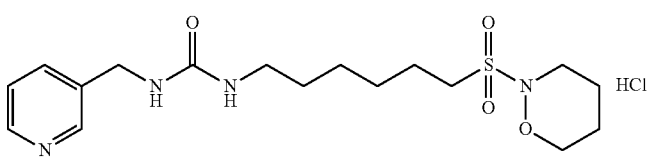 [SMILES: O=C(NCCCCCCS(=O)(=O)N1CCCCO1)NCc1cccnc1 ; Cl] |
| 1019. | 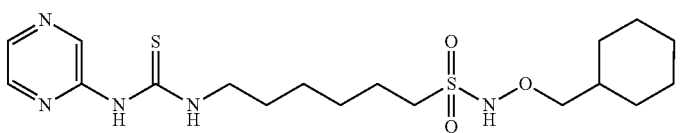 [SMILES: O=S(=O)(CCCCCCNC(=S)Nc1cnccn1)NOCC1CCCCC1] |

-continued
| Compound | Structure |
|---|---|
| 1020. | 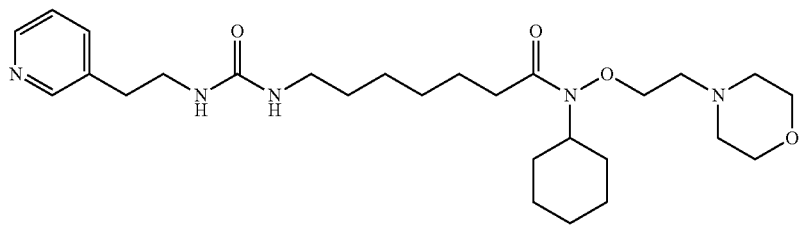 |
| 1021. | 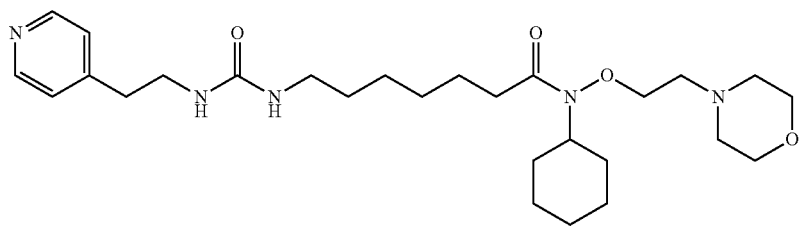 |
| 1022. | 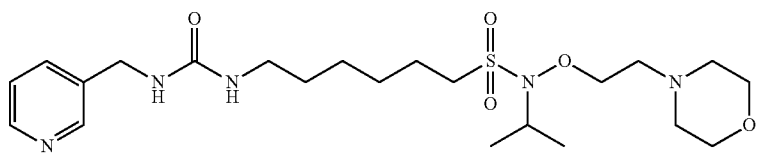 |
| 1023. | 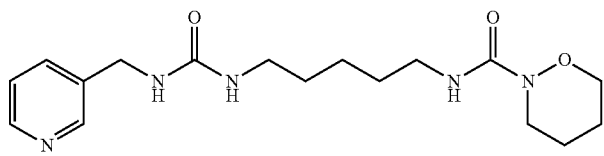 [SMILES: O=C(NCCCCCNC(=O)N1CCCCO1)NCc1cccnc1] |
| 1024. | 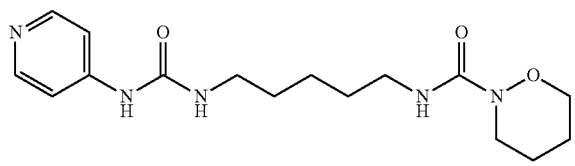 [SMILES: O=C(NCCCCCNC(=O)N1CCCCO1)Nc1ccncc1] |
| 1025. | 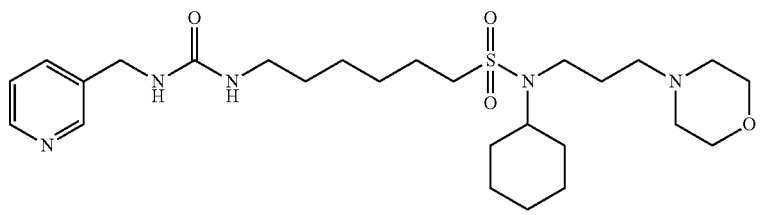 [SMILES: O=C(NCCCCCCS(=O)(=O)N(CCCN1CCOCC1)C1CCCCC1)NCc1cccnc1] |
| 1026. | 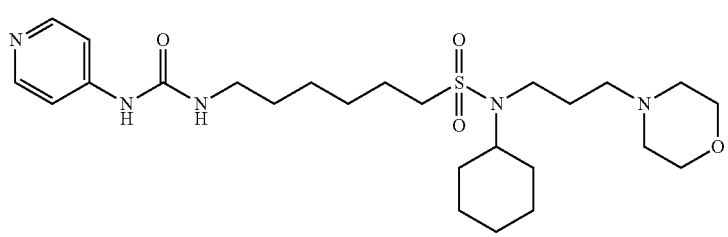 [SMILES: O=C(NCCCCCCS(=O)(=O)N(CCCN1CCOCC1)C1CCCCC1)Nc1ccncc1] |

| Compound | Structure |
|---|---|
| 1027. | 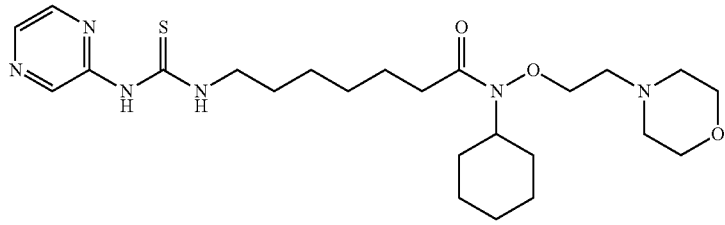 |
| 1028. | 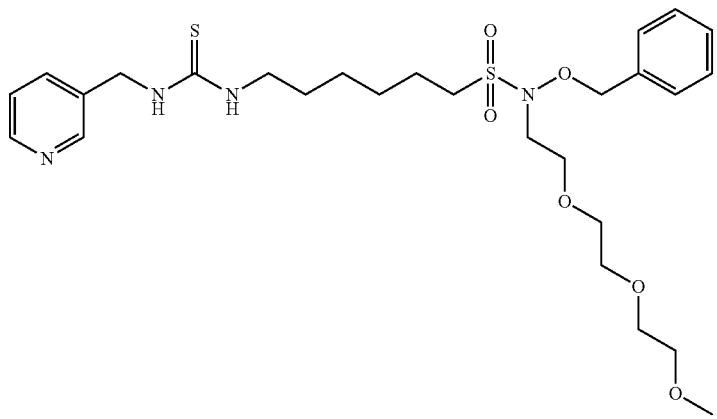 [SMILES: COCCOCCOCCN(OCc1ccccc1)S(=O)(=O)CCCCCCNC(=S)NCc1cccnc1] |
| 1029. | 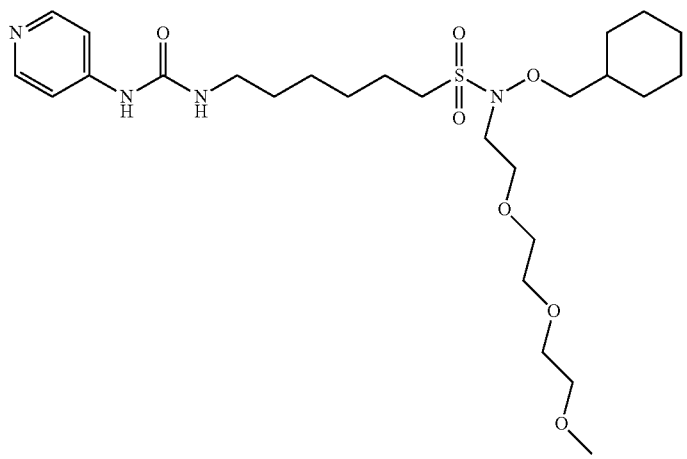 [SMILES: COCCOCCOCCN(OCC1CCCCC1)S(=O)(=O)CCCCCCNC(=O)Nc1ccncc1] |
| 1030. | 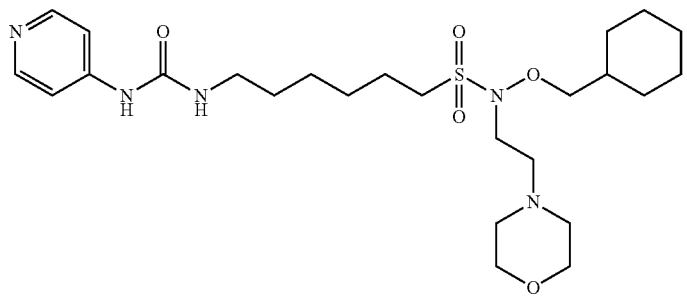 [SMILES: O=C(NCCCCCCS(=O)(=O)N(CCN1CCOCC1)OCC1CCCCC1)Nc1ccncc1] |

| Compound | Structure |
|---|---|
| 1031. | 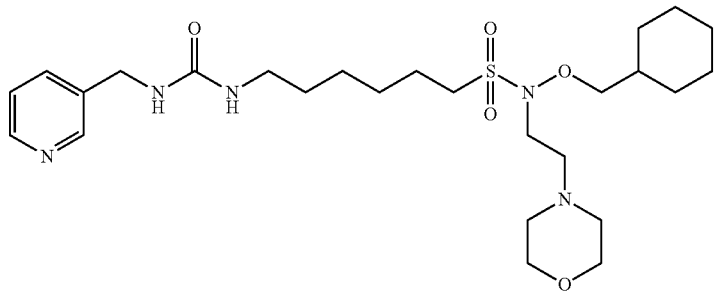 [SMILES: O=C(NCCCCCCS(=O)(=O)N(CCN1CCOCC1)OCC1CCCCC1)NCc1cccnc1] |
| 1032. | 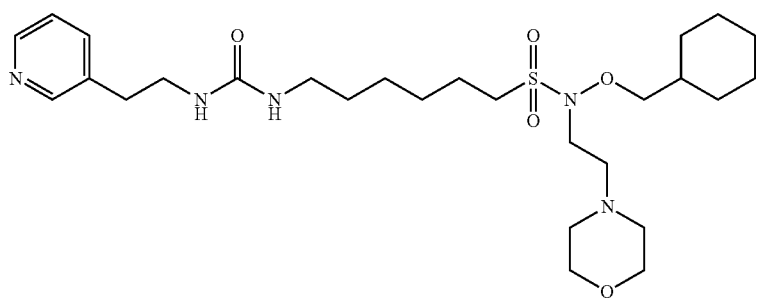 [SMILES: O=C(NCCCCCCS(=O)(=O)N(CCN1CCOCC1)OCC1CCCCC1)NCCc1cccnc1] |
| 1033. | 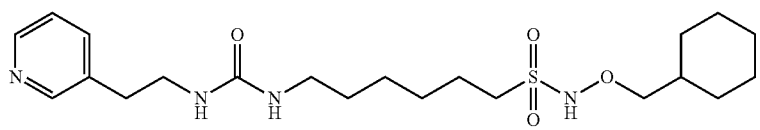 [SMILES: O=C(NCCCCCCS(=O)(=O)NOCC1CCCCC1)NCCc1cccnc1] |
| 1034. | 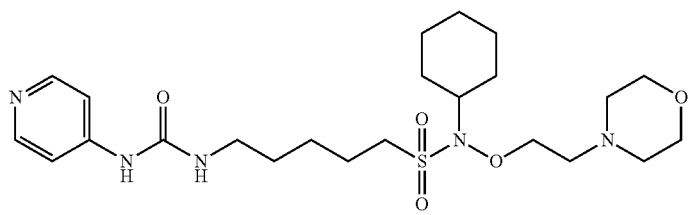 [SMILES: O=C(NCCCCCS(=O)(=O)N(OCCN1CCOCC1)C1CCCCC1)Nc1ccncc1] |
| 1035. | 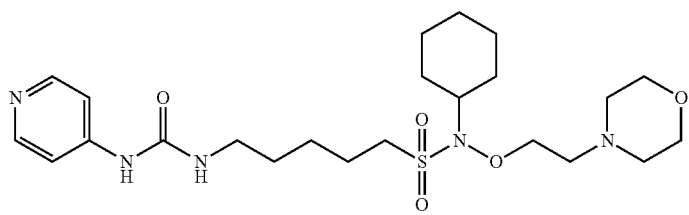 [SMILES: O=C(NCCCCCS(=O)(=O)N(OCCN1CCOCC1)C1CCCCC1)Nc1ccncc1] |
| 1036. | 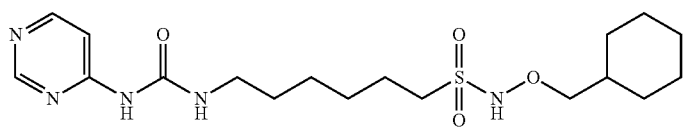 |
| 1037. | 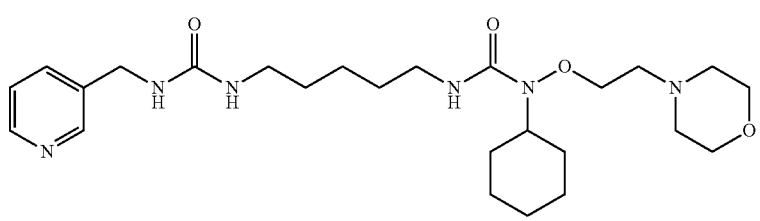 [SMILES: O=C(NCCCCCNC(=O)N(OCCN1CCOCC1)C1CCCCC1)NCc1cccnc1] |

-continued
| Compound Structure |
|---|
| 1038. 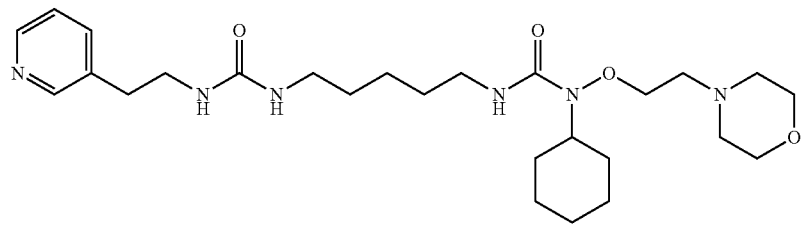 |
| 1039. 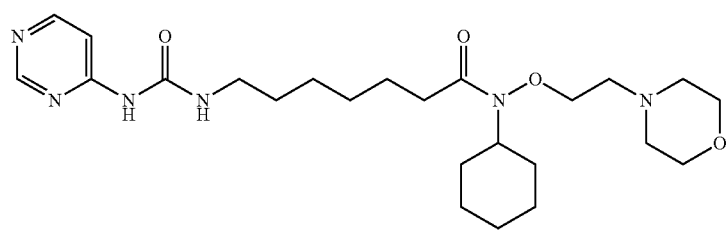 |
| 1040. 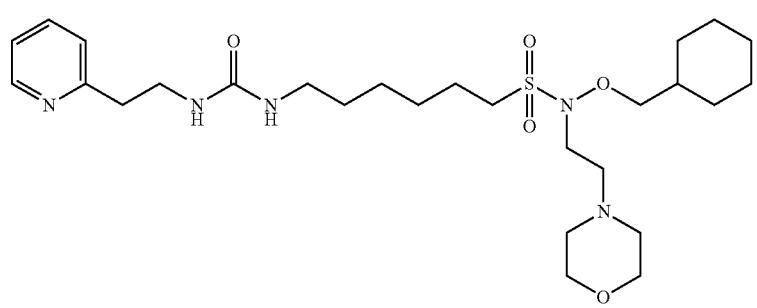 [SMILES: O=C(NCCCCCCS(=O)(=O)N(CCN1CCOCC1)OCC1CCCCC1)NCCc1ccccn1] |
| 1041. 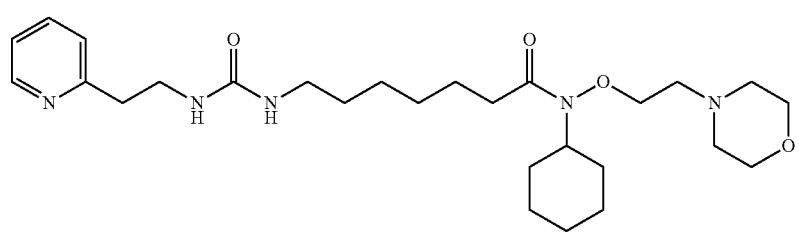 [SMILES: O=C(NCCCCCCC(=O)N(OCCN1CCOCC1)C1CCCCC1)NCCc1ccccn1] |
| 1042. 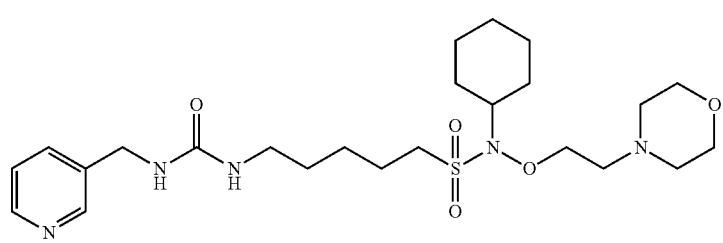 [SMILES: O=C(NCCCCCS(=O)(=O)N(OCCN1CCOCC1)C1CCCCC1)NCc1cccnc1] |
| 1043. 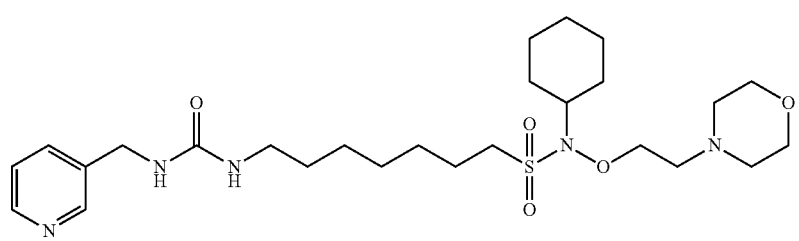 [SMILES: O=C(NCCCCCCCS(=O)(=O)N(OCCN1CCOCC1)C1CCCCC1)NCc1cccnc1] |

| Compound | Structure |
|---|---|
| 1044. | 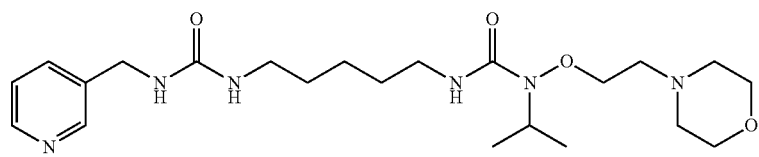 [SMILES: CC(C)N(OCCN1CCOCC1)C(=O)NCCCCCNC(=O)NCc1cccnc1] |
| 1045. | 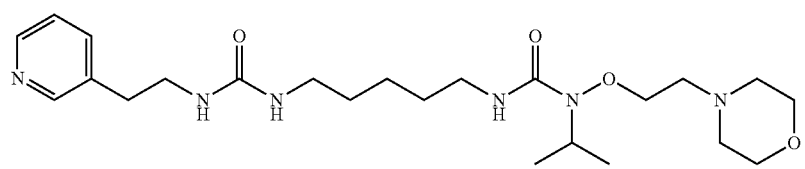 [SMILES: CC(C)N(OCCN1CCOCC1)C(=O)NCCCCCNC(=O)NCCc1cccnc1] |
| 1046. | 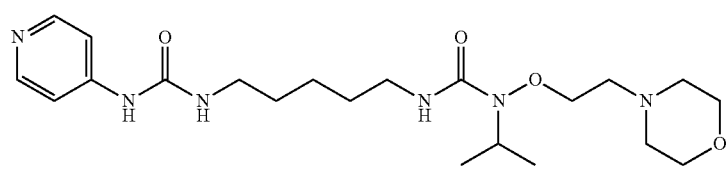 [SMILES: CC(C)N(OCCN1CCOCC1)C(=O)NCCCCCNC(=O)Nc1ccncc1] |
| 1047. | 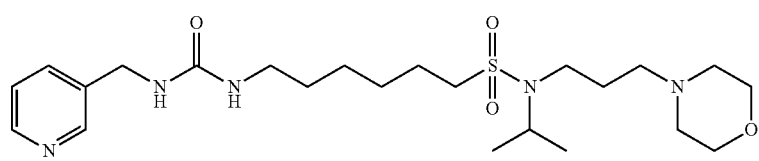 |
| 1048. | 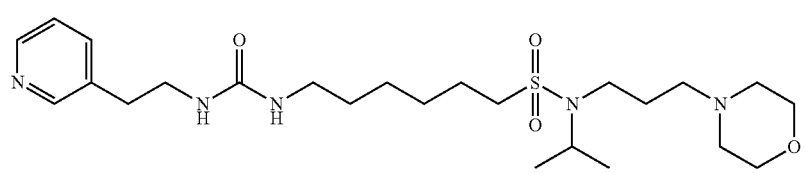 [SMILES: CC(C)N(CCCN1CCOCC1)S(=O)(=O)CCCCCCNC(=O)NCCc1cccnc1] |
| 1049. | 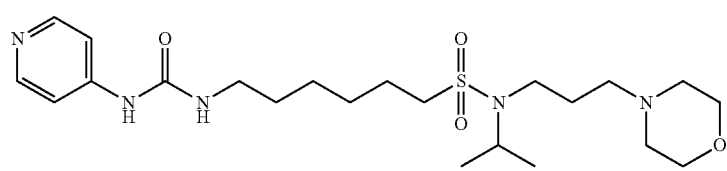 [SMILES: CC(C)N(CCCN1CCOCC1)S(=O)(=O)CCCCCCNC(=O)Nc1ccncc1] |
| 1050. | 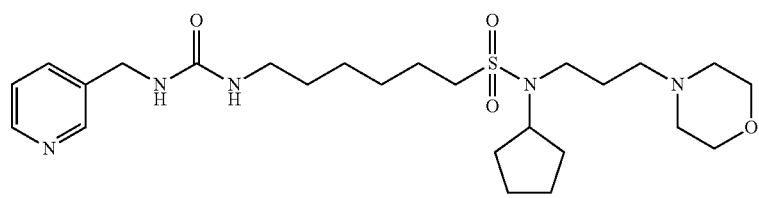 [SMILES: O=C(NCCCCCCS(=O)(=O)N(CCCN1CCOCC1)C1CCCC1)NCc1cccnc1] |
| 1051. | 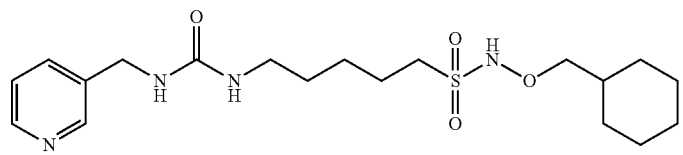 [SMILES: O=C(NCCCCCS(=O)(=O)NOCC1CCCCC1)NCc1cccnc1] |
| 1052. | 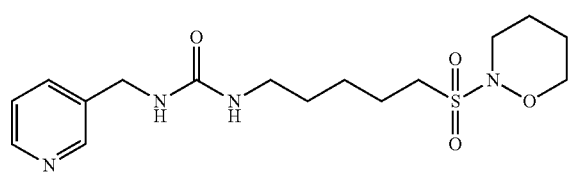 [SMILES: O=C(NCCCCCS(=O)(=O)N1CCCCO1)NCc1cccnc1] |

| Compound | Structure |
|---|---|
| 1053. | 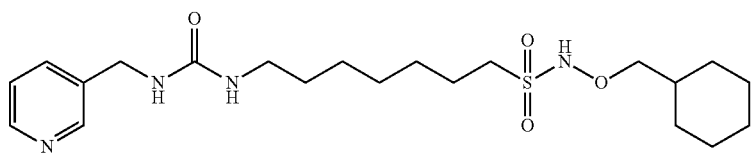 [SMILES: O=C(NCCCCCCCS(=O)(=O)NOCC1CCCCC1)NCc1cccnc1] |
| 1054. | 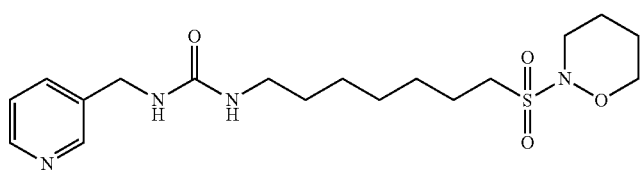 [SMILES: O=C(NCCCCCCCS(=O)(=O)N1CCCCO1)NCc1cccnc1] |
| 1055. | 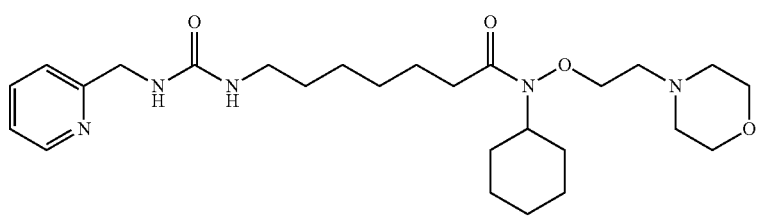 [SMILES: O=C(NCCCCCCC(=O)N(OCCN1CCOCC1)C1CCCCC1)NCc1ccccn1] |
| 1056. | 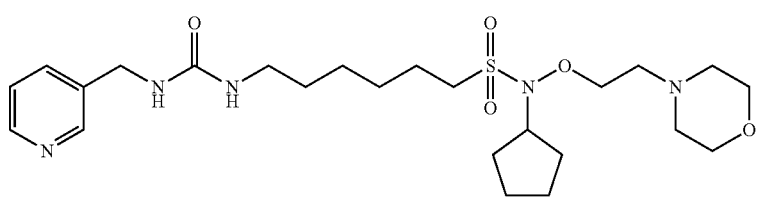 [SMILES: O=C(NCCCCCCS(=O)(=O)N(OCCN1CCOCC1)C1CCCC1)NCc1cccnc1] |
| 1057. | 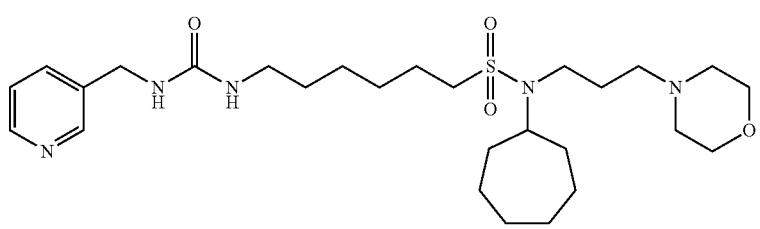 |
| 1058. | 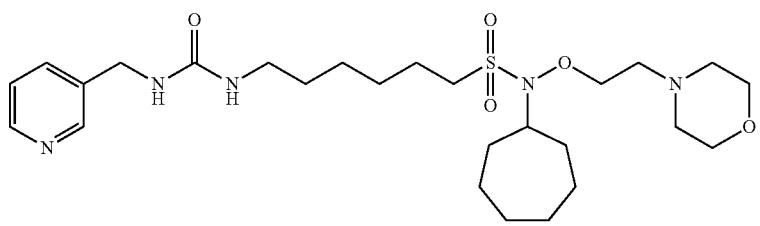 |
| 1059. | 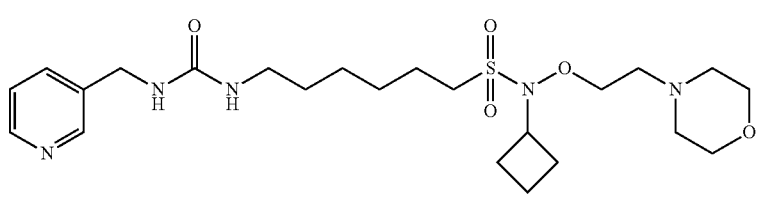 [SMILES: O=C(NCCCCCCS(=O)(=O)N(OCCN1CCOCC1)C1CCC1)NCc1cccnc1] |
| 1060. | 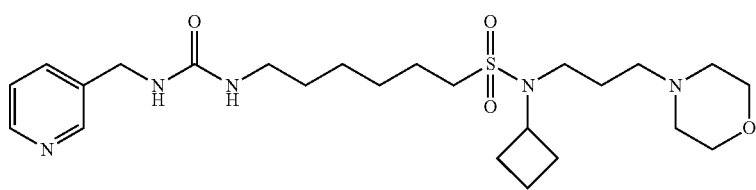 [SMILES: O=C(NCCCCCCS(=O)(=O)N(CCCN1CCOCC1)C1CCC1)NCc1cccnc1] |

| Compound | Structure |
|---|---|
| 1061. | 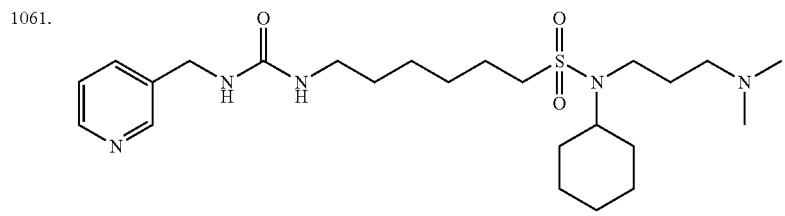 |
| 1062. | 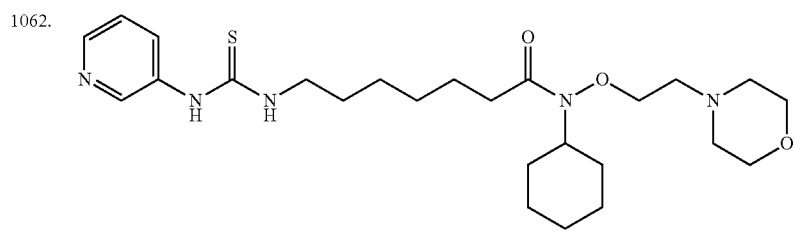 |
| 1063. | 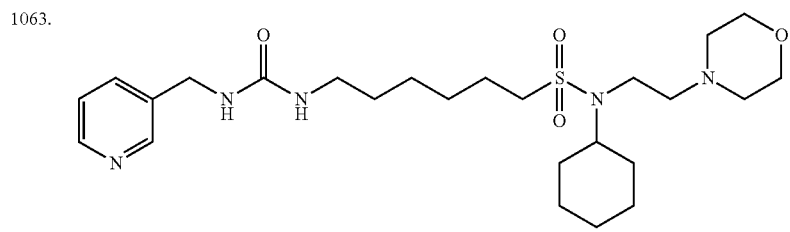 |
| 1064. | 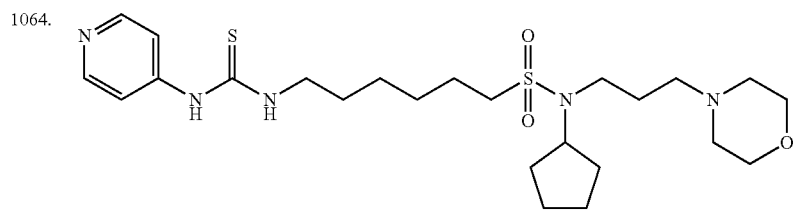 |
| 1065. | 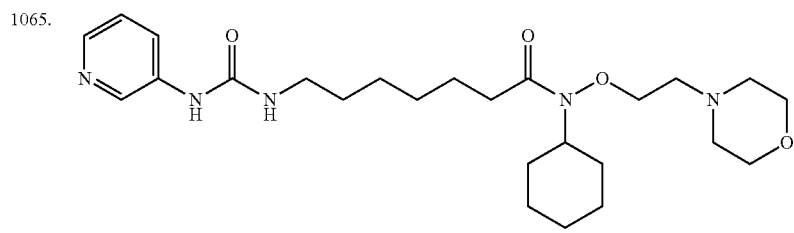 |
| 1066. | 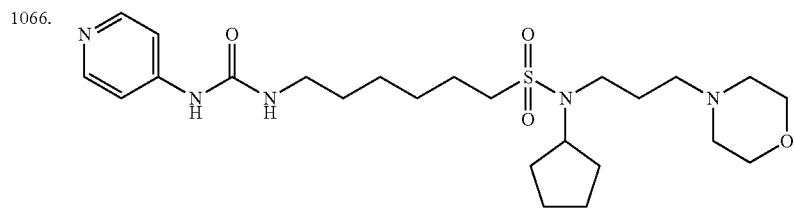 |
| 1067. | 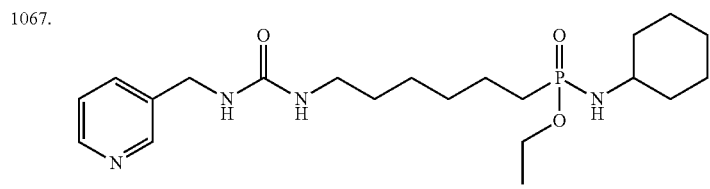 |

| Compound | Structure |
|---|---|
| 1068. | 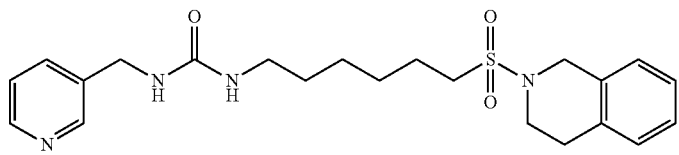 [SMILES: O=C(NCCCCCCS(=O)(=O)N1CCc2ccccc2C1)NCc1cccnc1] |
| 1069. | 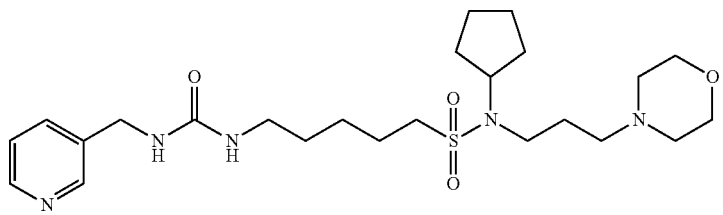 [SMILES: O=C(NCCCCCS(=O)(=O)N(CCCN1CCOCC1)C1CCCC1)NCc1cccnc1] |
| 1070. | 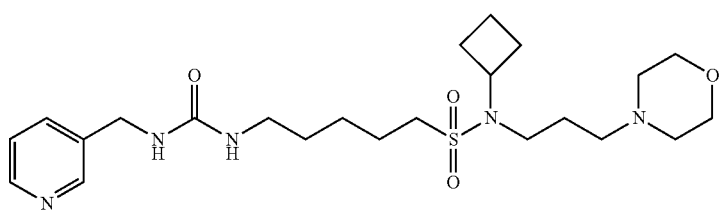 [SMILES: O=C(NCCCCCS(=O)(=O)N(CCCN1CCOCC1)C1CCC1)NCc1cccnc1] |
| 1071. | 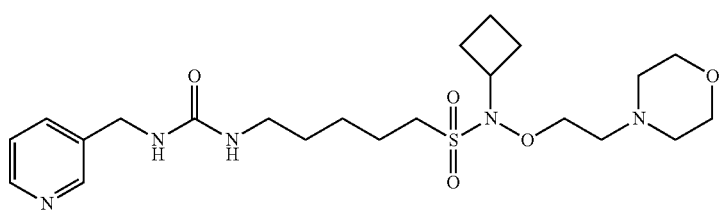 |
| 1072. | 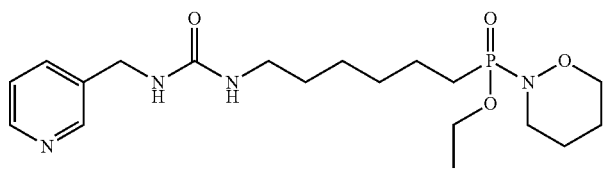 [SMILES: CCOP(=O)(CCCCCCNC(=O)NCc1cccnc1)N1CCCCO1] |
| 1073. | 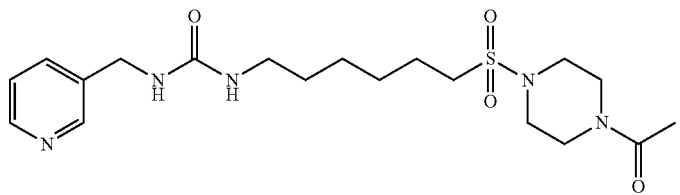 [SMILES: CC(=O)N1CCN(S(=O)(=O)CCCCCCNC(=O)NCc2cccnc2)CC1] |
| 1074. | 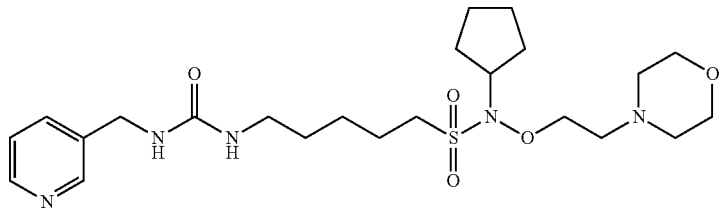 [SMILES: O=C(NCCCCCS(=O)(=O)N(OCCN1CCOCC1)C1CCCC1)NCc1cccnc1] |

| Compound | Structure |
|---|---|
| 1075. | 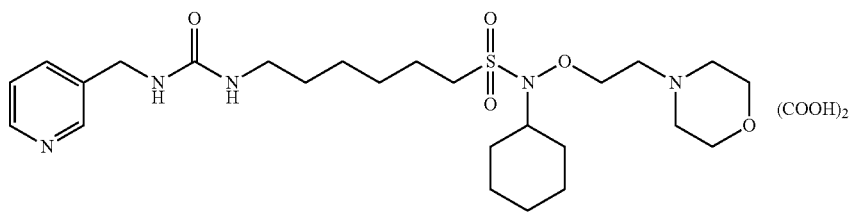 (COOH)₂ |
| 1076. | 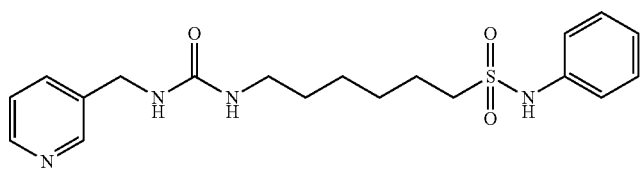 [SMILES: O=C(NCCCCCCS(=O)(=O)Nc1ccccc1)NCc1cccnc1] |
| 1077. | 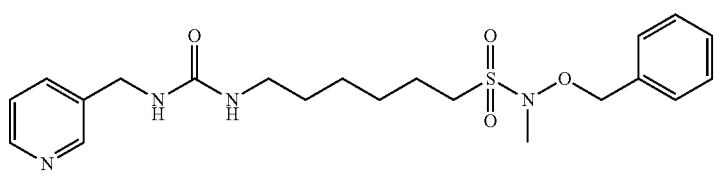 [SMILES: CN(OCc1ccccc1)S(=O)(=O)CCCCCCNC(=O)NCc1cccnc1] |
| 1078. | 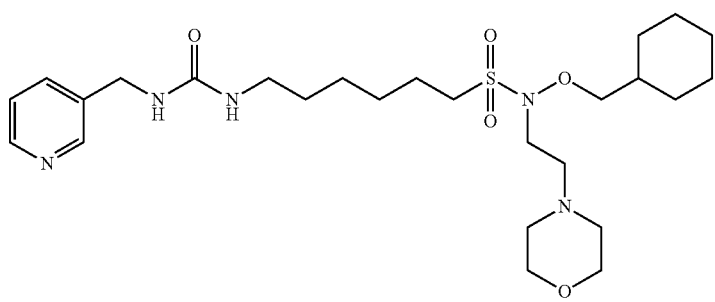 [SMILES: O=C(NCCCCCCS(=O)(=O)N(CCN1CCOCC1)OCC1CCCCC1)NCc1cccnc1] |
| 1079. | 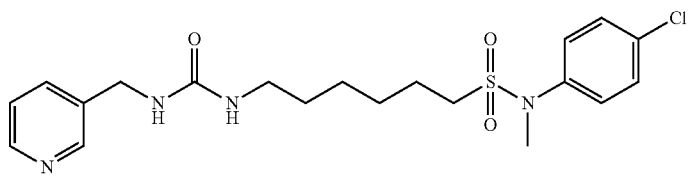 [SMILES: CN(c1ccc(Cl)cc1)S(=O)(=O)CCCCCCNC(=O)NCc1cccnc1] |
| 1080. | 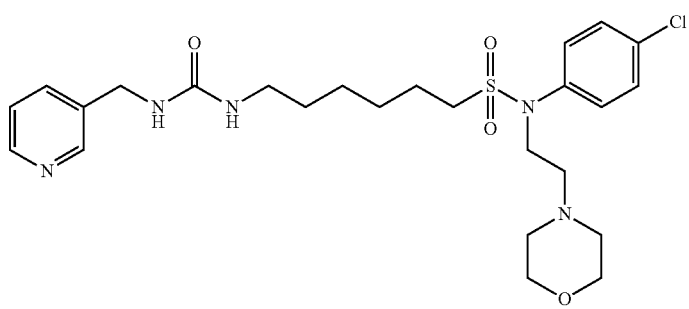 [SMILES: O=C(NCCCCCCS(=O)(=O)N(CCN1CCOCC1)c1ccc(Cl)cc1)NCc1cccnc1] |
| 1081. | 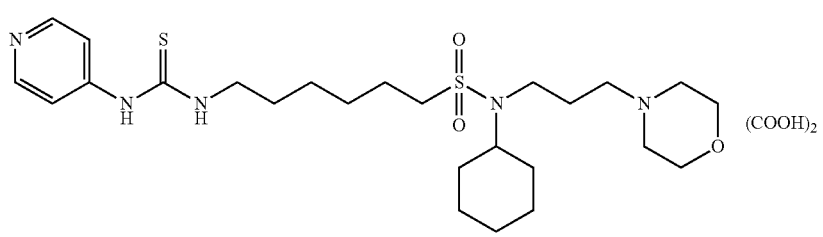 (COOH)₂ |

| Compound | Structure |
|---|---|
| 1082. | 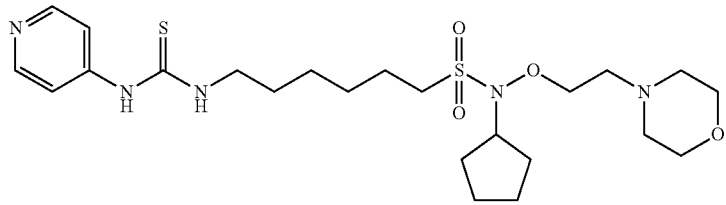 |
| 1083. | 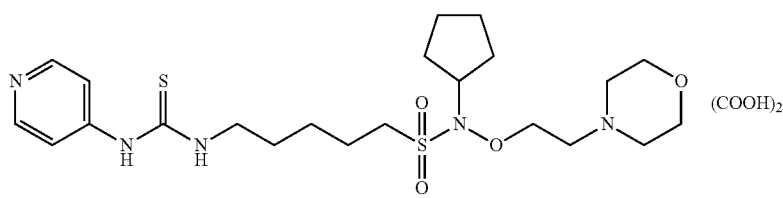 (COOH)$_2$ |
| 1084. | 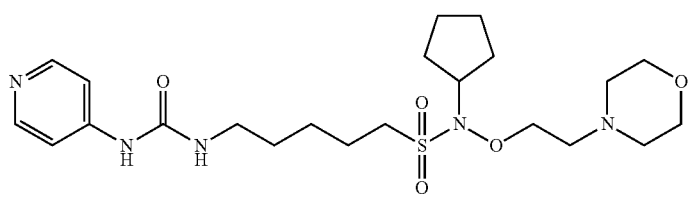 [SMILES: O=C(NCCCCCS(=O)(=O)N(OCCN1CCOCC1)C1CCCC1)Nc1ccncc1] |
| 1085. | 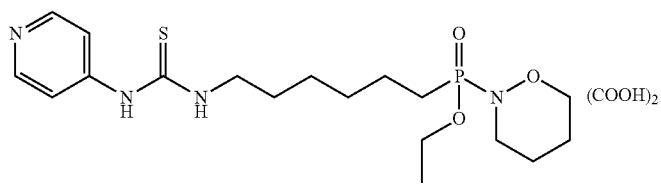 (COOH)$_2$ |
| 1086. | 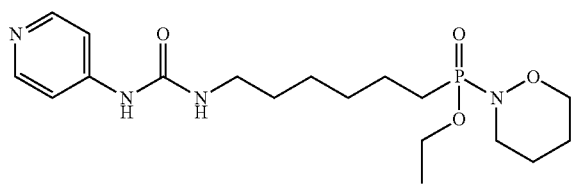 [SMILES: CCOP(=O)(CCCCCCNC(=O)Nc1ccncc1)N1CCCCO1] |
| 1087. | 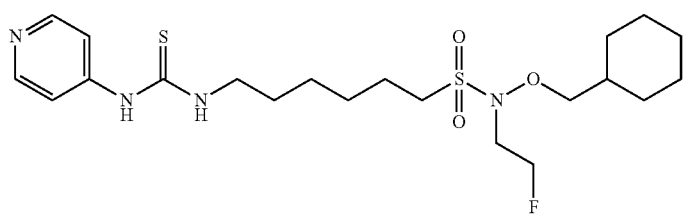 |
| 1088. | 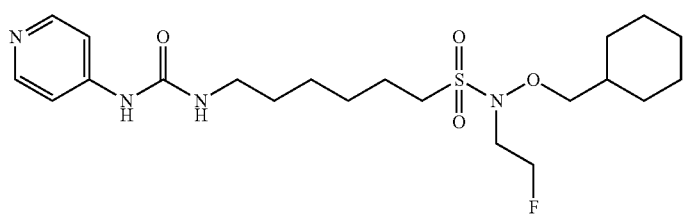 |

| Compound Structure |
|---|
| 1089. 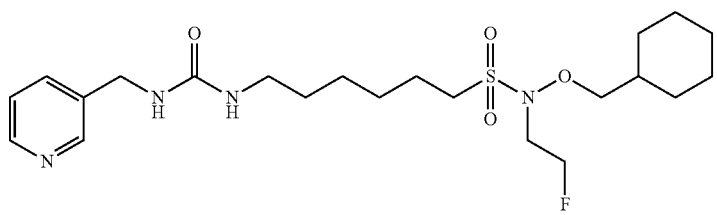 [SMILES: O=C(NCCCCCCS(=O)(=O)N(CCF)OCC1CCCCC1)NCc1cccnc1] |
| 1090. 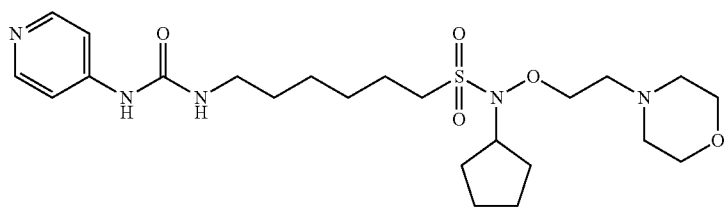 |
| 1091. 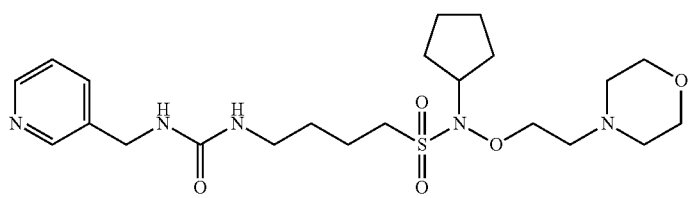 |
| 1092. 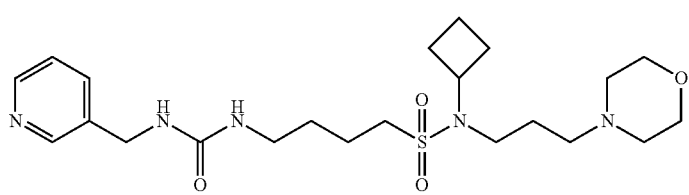 [SMILES: O=C(NCCCCS(=O)(=O)N(CCCN1CCOCC1)C1CCC1)NCc1cccnc1] |
| 1093. 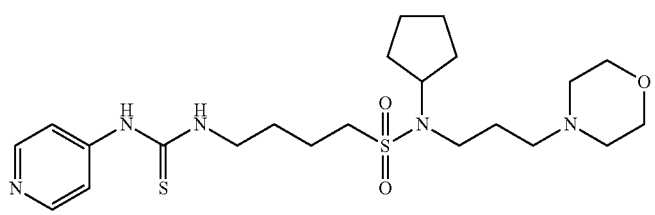 [SMILES: O=S(=O)(CCCCNC(=S)Nc1ccncc1)N(CCCN1CCOCC1)C1CCCC1] |
| 1094. 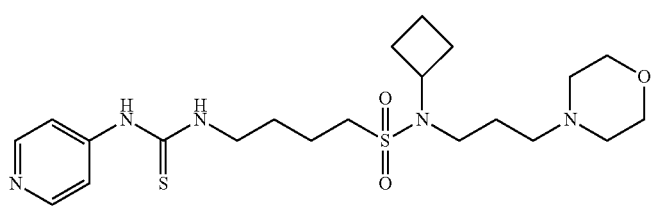 [SMILES: O=S(=O)(CCCCNC(=S)Nc1ccncc1)N(CCCN1CCOCC1)C1CCC1] |
| 1095. 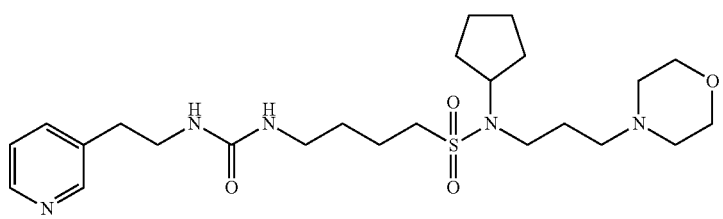 [SMILES: O=C(NCCCCS(=O)(=O)N(CCCN1CCOCC1)C1CCCC1)NCCc1cccnc1] |

| Compound | Structure |
|---|---|
| 1096. | 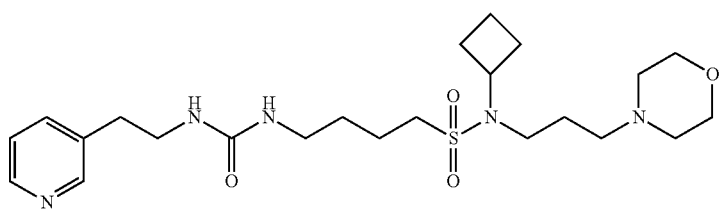 [SMILES: O=C(NCCCCS(=O)(=O)N(CCCN1CCOCC1)C1CCC1)NCCc1cccnc1] |
| 1097. | 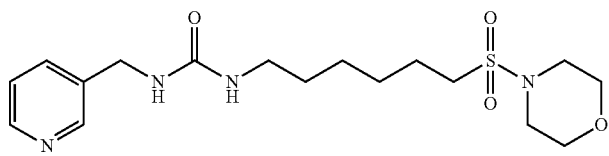 [SMILES: O=C(NCCCCCCS(=O)(=O)N1CCOCC1)NCc1cccnc1] |
| 1098. | 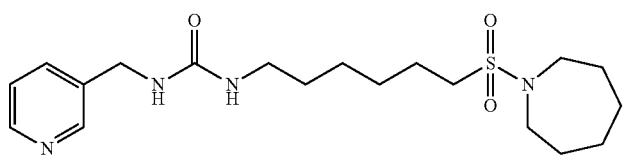 [SMILES: O=C(NCCCCCCS(=O)(=O)N1CCCCCC1)NCc1cccnc1] |
| 1099. | 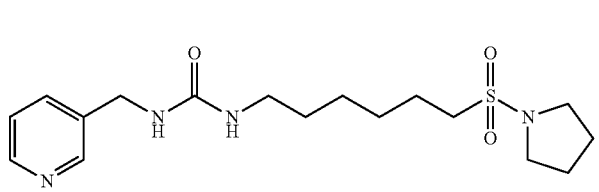 [SMILES: O=C(NCCCCCCS(=O)(=O)N1CCCC1)NCc1cccnc1] |
| 1100. | 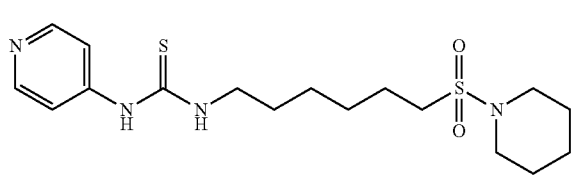 |
| 1101. | 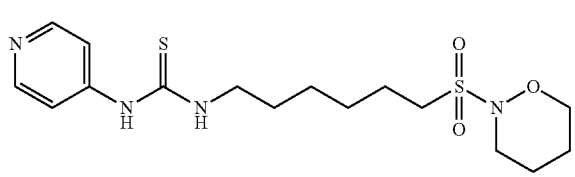 |

General Procedures

The compounds of the present invention can be synthesized using the methods outlined below, together with methods known in the art of organic synthetic organic chemistry, or variations thereof as appreciated by those skilled in the art. Preferred methods include, but are not limited to, those described below.

The novel compounds of formula (I) may be prepared using the reactions and techniques described in this section. The reactions are performed in solvents appropriate to the reagents and materials employed and suitable for the transformations being effected. Also, in the synthetic methods described below, it is to be understood that all proposed reaction conditions, including choice of solvent, reaction atmosphere, reaction temperature duration of experiment and work-up procedures, are chosen to be conditions of standard for that reaction, which should be readily recognized by one skilled in the art. It is understood by one skilled in the art of organic synthesis that the functionality present on various portions of the educt molecule must be compatible with the reagents and reactions proposed. Not all molecules of formula (I) falling into a given class may be compatible with some of the reaction conditions required in some of the methods described. Such restrictions to the substituents which are compatible with the reaction conditions will be readily apparent to one skilled in the art and alternative methods can be used.

Compounds (I) according to the present invention which are ureas (Ia) can be prepared in several ways, e.g. by reaction of amines of general formula (II) with 1,1'-carbonyldiimidazole (CDI) or 4-nitrophenyl chloroformate followed by reaction with amines of general formula (III).

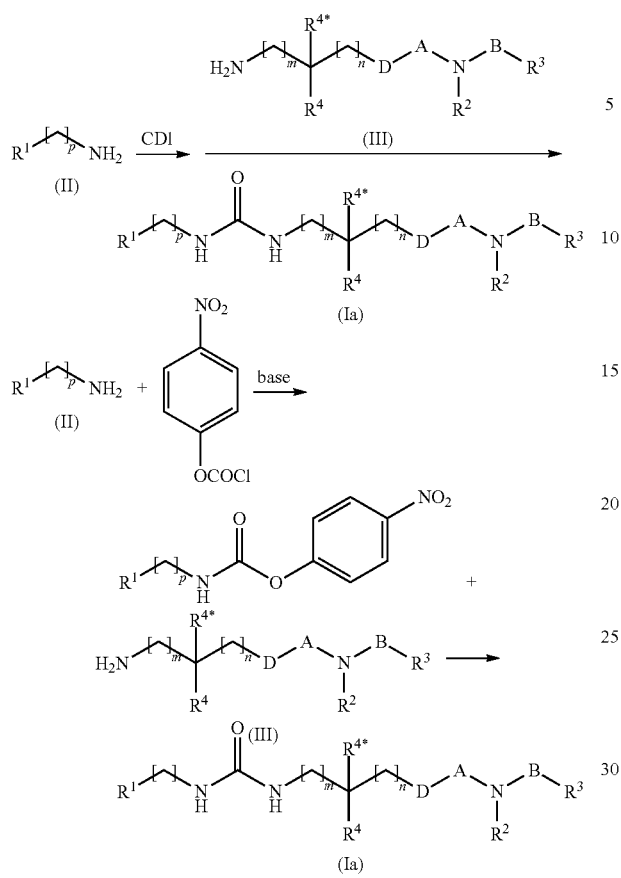

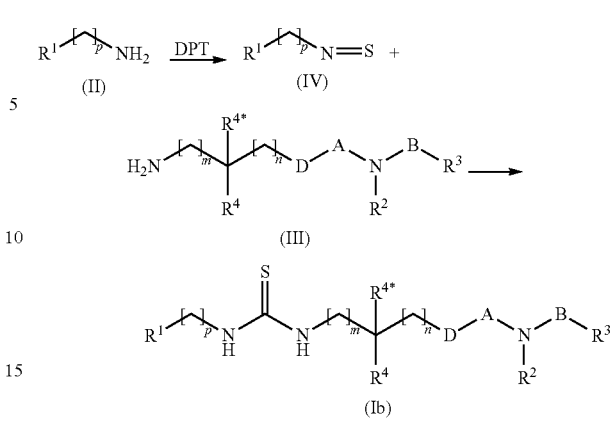

Compounds (I) according to the present invention which are alkoxyguanidines (Ic) can be prepared by conversion of thioureas (Ib) into the corresponding carbodiimide (V), e.g. by reaction with a carbodiimide (e.g. EDC or DCCl) or HgO, followed by reaction with O-alkoxyhydroxylamine. In a similar manner, compounds (I) according to the present invention which are hydroxyguanidines (Id) or guanidines (Ie) may be prepared, substituting O-alkoxyhydroxylamine with hydroxylamine or a protected hydroxylamine, or ammonia or an ammonia equivalent, respectively. If a protected hydroxylamine or ammonia equivalent is employed, a deprotection step is necessary. The protecting group may e.g. be tetrahydropyranyl (THP), t-butyl, benzyl or a silyl-based protecting group.

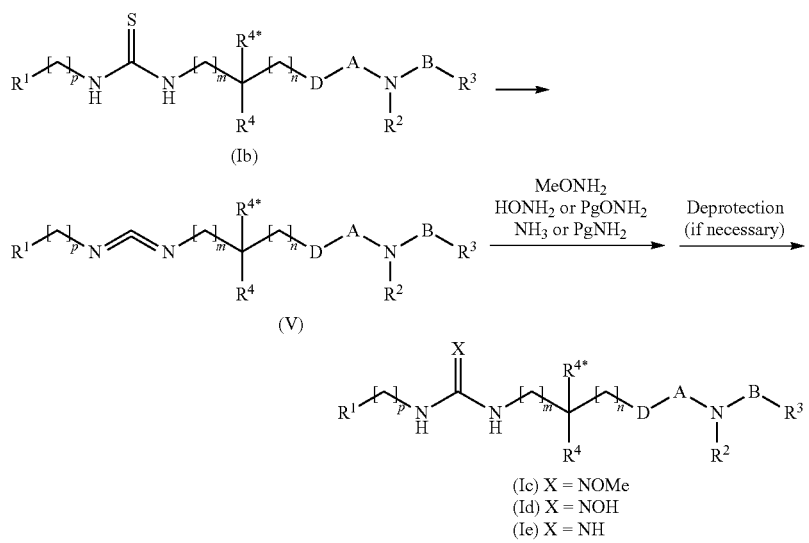

Compounds (I) according to the present invention which are thioureas (Ib) can be prepared in several ways, e.g. by reaction of amines (III) with isothiocyanates of general formula (IV). Isothiocyanates (IV) are either commercially available or can be prepared from amines of general formula (II) by reaction with di(2-pyridyl) thionocarbonate (DPT).

Alternatively, thioureas of general formula (Ib) may be methylated and subsequently allowed to react with O-methoxyhydroxylamine, hydroxylamine or a protected hydroxylamine, or ammonia or an ammonia equivalent, respectively. If a protected hydroxylamine or ammonia equivalent is employed, a deprotection step is necessary.

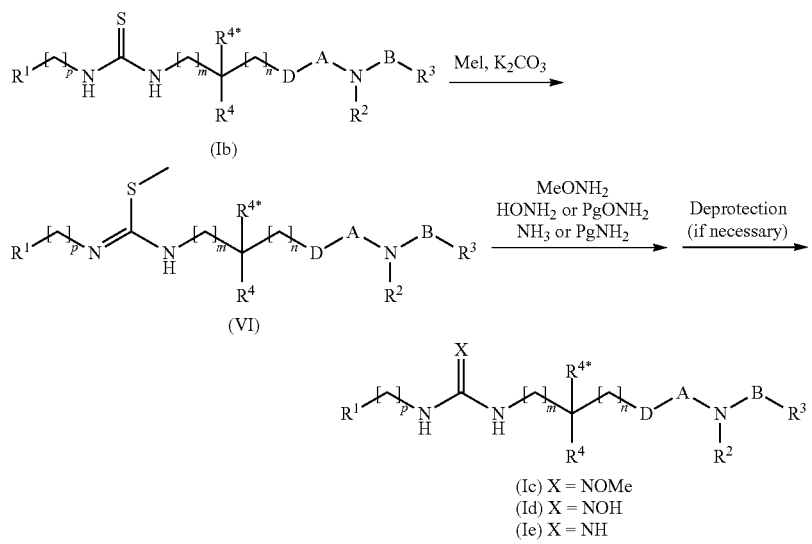

Compounds (I) according to the present invention which are methoxyguanidines (Ic), hydroxyguanidines (Id) or guanidines (Ie) may e.g. also be prepared from N-arylsulfonyl-S-methylisothioureas, cyanamides, pyrazole-1-carboximidamides, triflate guanidines, and benzotriazole and imidazole-containing reagents (see e.g. A. R. Katritzky et al.: *J. Org. Chem.* (2006) 71, 6753-6778 and references cited herein).

Amines of general formula (III), which are hydroxamic acid esters, N-alkyl- or N-arylhydrazides, N,N'-dialkyl- or N,N'-diarylhydrazides (IIIa) can be prepared from protected amino acids of general formula (VII) (protecting group Pg e.g. Boc or phtalimido) by coupling with hydroxylamines or hydrazines of general formula (VIII) using a peptide coupling reagent (e.g. EDC or HATU), and subsequent removal of the protecting group.

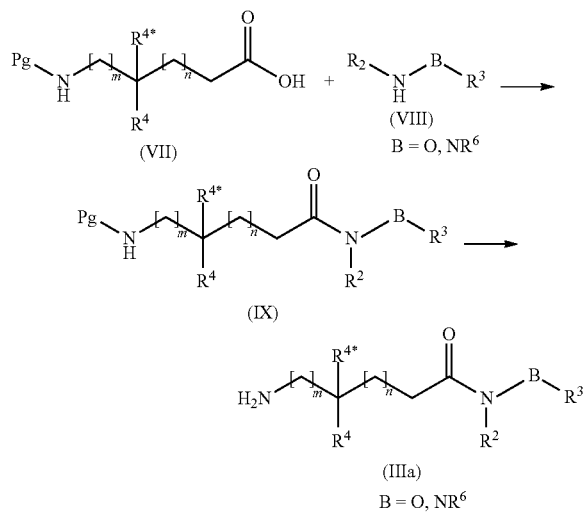

In the special case where amines of general formula (IIIa) contain a substituent alpha to the carbonyl group they can be prepared from amino acids of general formula (X) or their enantiomers (obtained as described in the literature e.g K. S. Orwig et al.: *Tet. Lett.* (2005) 46 7007-7009), followed by protection of the amino group (e.g. with Boc, phtalimido or other) and subsequent coupling with hydroxylamines or hydrazines followed by deprotection as described above.

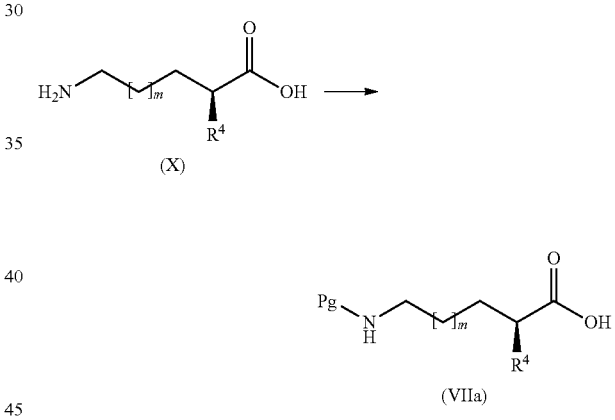

Hydroxylamines (VIII, B=O)) are either commercially available or can be prepared from N-hydroxyphtalimide (or alternatively tert-butylhydroxycarbamate) by alkylation with a halogenide and a base (e.g. DBU) or a Mitsunobu reaction with an alcohol (using e.g. DEAD), followed by deprotection with hydrazine or methylhydrazine, resulting in hydroxylamine (VIIIa). When $R^2$ is not hydrogen, the resulting hydroxylamine (VIIIa) may be submitted to reductive amination with an aldehyde or ketone followed by reduction with e.g. sodium cyanoborohydride as described in the literature (e.g. B. J. Mavunkel et al.: *Eur. J. Med. Chem.* (1994) 29, 659-666; T. Ishikawa et. al.: *J. Antibiotics* (2000), 53 (10), 1071-1085; J. Ishwara Bhat et al.: *J. Chem. Soc., Perkin Trans.* 2 (2000), 1435-1446). Alternatively, alkylation of the hydroxylamine (VIIIa) can be achieved by a Mitsunobu reaction or alkylation after protection with e.g. 2-nitrophenylsulfonylchloride and subsequent removal of the protecting group (using e.g. thiophenol and cesium carbonate).

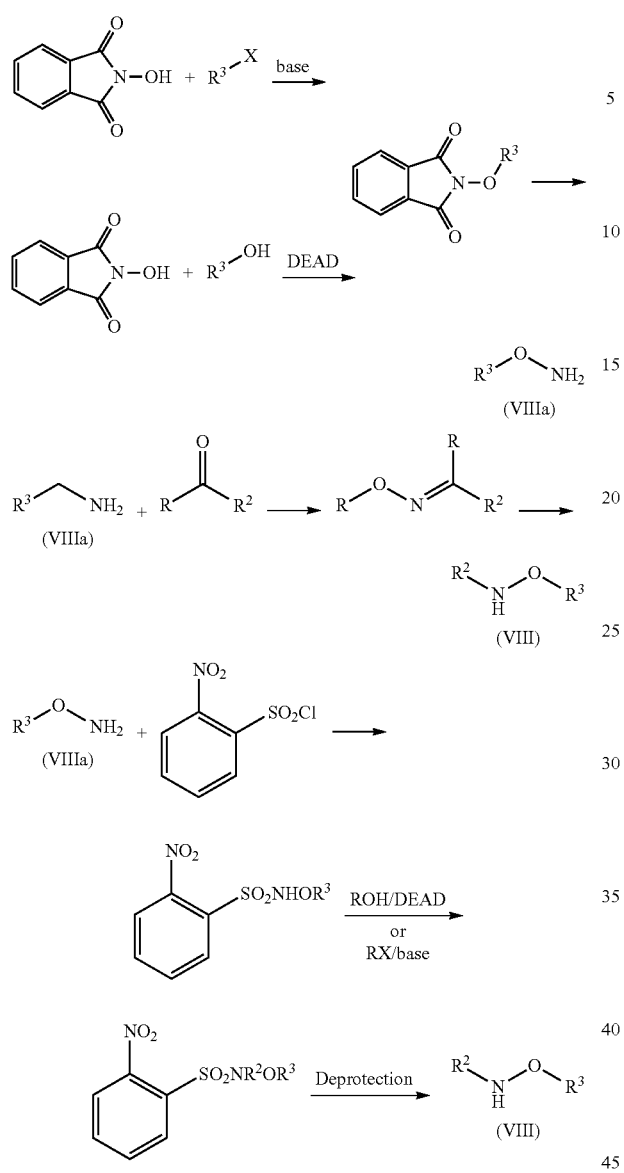

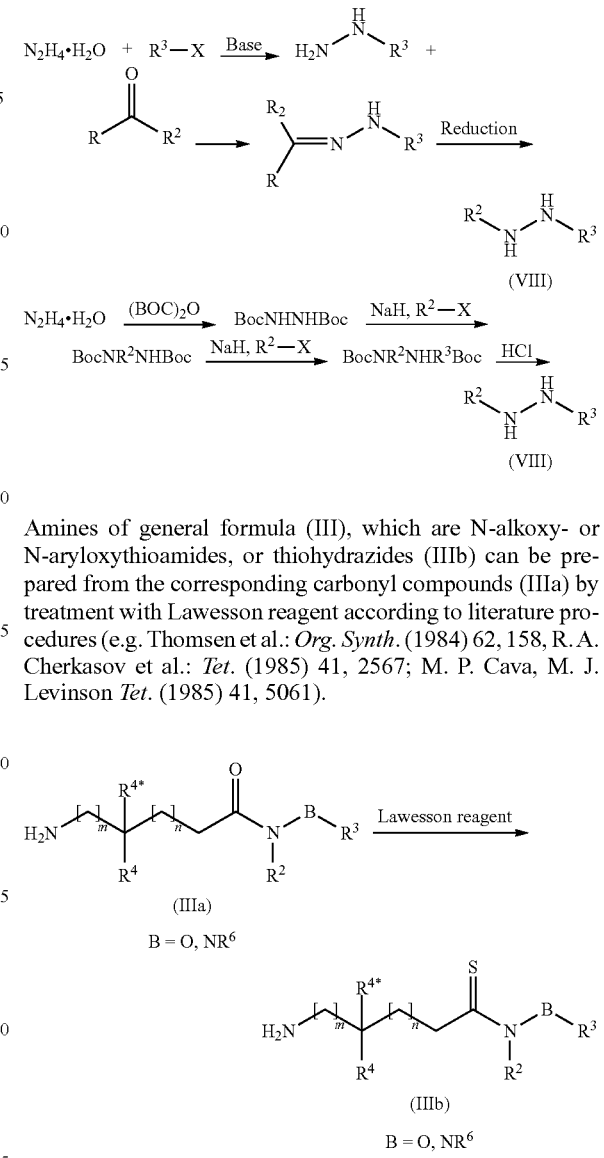

Amines of general formula (III), which are N-alkoxy- or N-aryloxythioamides, or thiohydrazides (IIIb) can be prepared from the corresponding carbonyl compounds (IIIa) by treatment with Lawesson reagent according to literature procedures (e.g. Thomsen et al.: *Org. Synth.* (1984) 62, 158, R. A. Cherkasov et al.: *Tet.* (1985) 41, 2567; M. P. Cava, M. J. Levinson *Tet.* (1985) 41, 5061).

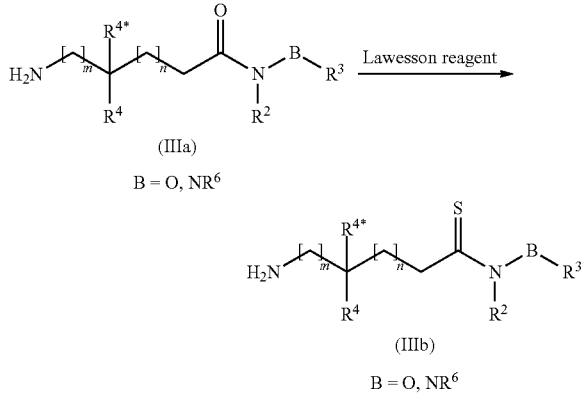

Hydrazines (VIII, B=O) are either commercially available or can—in the case where $R_2$ is H—be prepared from hydrazine hydrate by alkylation in the presence of a base according to literature procedures (e.g. D. J. Drain et al.: *J. Med. Chem.* (1963) 6 63-9; G. B. Marini-Bettolo et al.: *Rend. Ist. Super. Sanita* (1960) 23 1110-27). N,N'-Disubstituted hydrazines can be obtained from monosubstituted hydrazines (VIIIa) by reaction with an aldehyde or ketone followed by redcuction with e.g. hydrogen, LiAlH$_4$, or borane according to literature procedures (e.g. H. Dorn et. al.: *Zeitschrift für Chemie* (1972) 12(4) 129-30; R. L. Hinman: *JACS* (1957) 79 414-417; J. A. Blair: *JCS (Section) C: Organic* (1970) (12) 1714-17) or alternatively by Boc-protection of hydrazine hydrate, alkylation with an alkylhalogenide in the presence of sodium hydride, followed by a second alkylation with another alkylhalogenide in the presence of sodium hydride and finally removal of the Boc-protecting groups (L. Ling et al.: *Bioorg. Med. Chem. Lett.* (2001) (11) 2715-2717).

Alternatively, protected amino acids of general formula (VII) (protecting group e.g. Boc or phtalimido) can be converted into an activated species of general formula (XI) according to literature procedures (M. A. Shalaby et al.: *J. Org. Chem.* (1996) 61 9045-48) and subsequently allowed to react with hydroxylamines or hydrazines of general formula (VIII) followed by deprotection to yield amines of general formula (IIIb).

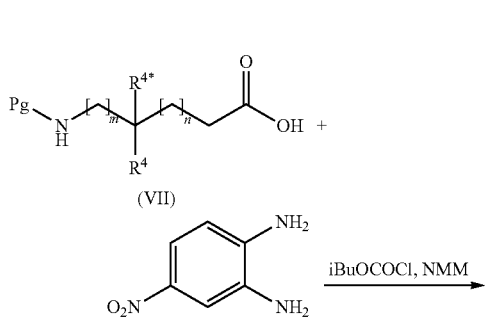

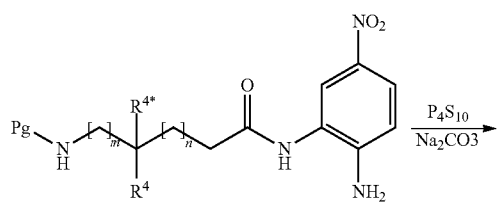

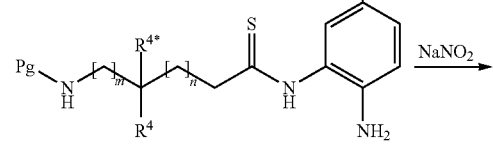

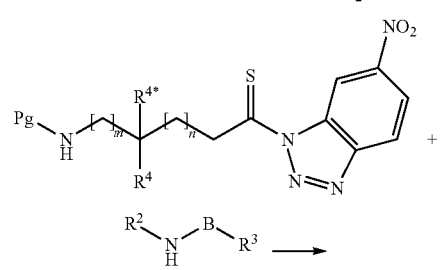

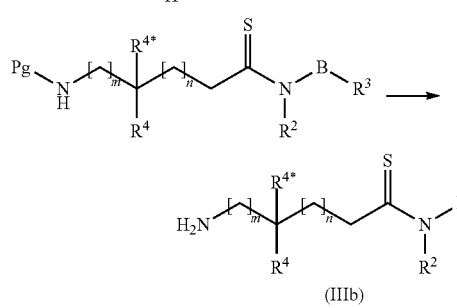

Amines of general formula (III), which are N-alkoxy or N-aryloxy sulfonamides, sulfonamides or sulfonylhydrazides (IIIc) can be obtained by reaction of phtalimidoalkanesulfonylchlorides (XII) (prepared as described in the literature, e.g. G. J. Atwell et al.: *J. Med. Chem.* (1977) 20(9) 1128-134; J. Humljan et al.: *Tet. Letters,* 46 4069-4072) with hydroxylamines, amines or hydrazines (VIII), respectively, in the presence of a base (e.g. triethyamine or N-methylmorpholine) followed by deprotection with hydrazine hydrate. Other protecting groups than phtalimido may be used.

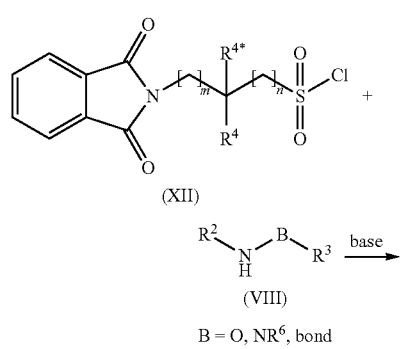

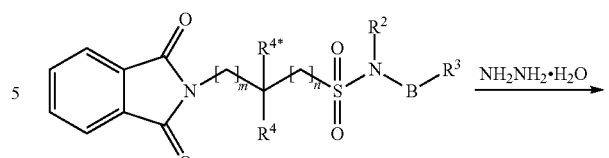

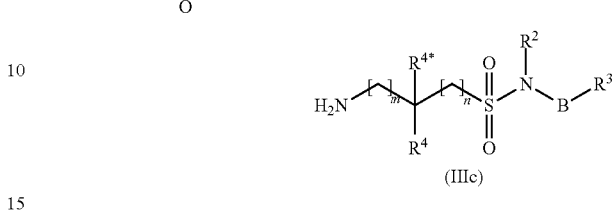

Amines of general formula (III) which are N-alkoxy-P-alkylphosphonamidates or N-aryloxy-P-alkylphosphonamidates, P-alkylphosphonamidates or P-alkylphosphonohydrazidates (IIId) can be obtained by reaction of the phtalimido protected phosphonochloridates (XIII) (prepared as described in the literature, e.g. S. Gobec et al.: *Tet. Lett.* (2002) 43 167-170; U. Urleb et al.: *Lett. In Peptide Science* (1995) 2 193-197) with hydroxylamines, amines or hydrazines (VIII), respectively, in the presence of a base followed by deprotection with hydrazine hydrate. Other protecting groups than phtalimido may be used.

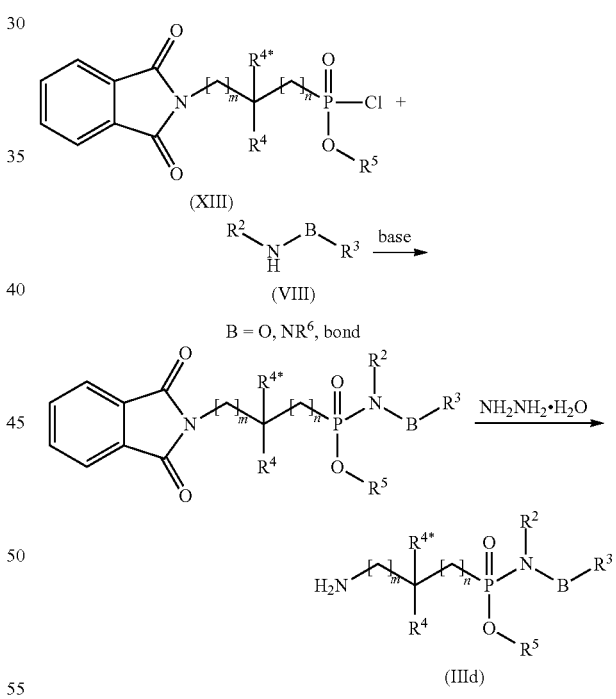

Amines of general formula (III) which are N-alkoxy-P-alkylphosphinic amides or N-aryloxy-P-alkylphosphinic amides, P-alkylphosphinic amides or P-alkylphosphinic hydrazides (IIIe) can be obtained by reaction of the phtalimido protected alkylphosphinic chlorides (XIV) (e.g. S. Gobec et al.: *Lett. In Peptide Science* (1998) 5 109-114) with hydroxylamines, amines or hydrazines (VIII), respectively, in the presence of a base followed by deprotection with hydrazine hydrate. Other protecting groups than phtalimido may be employed.

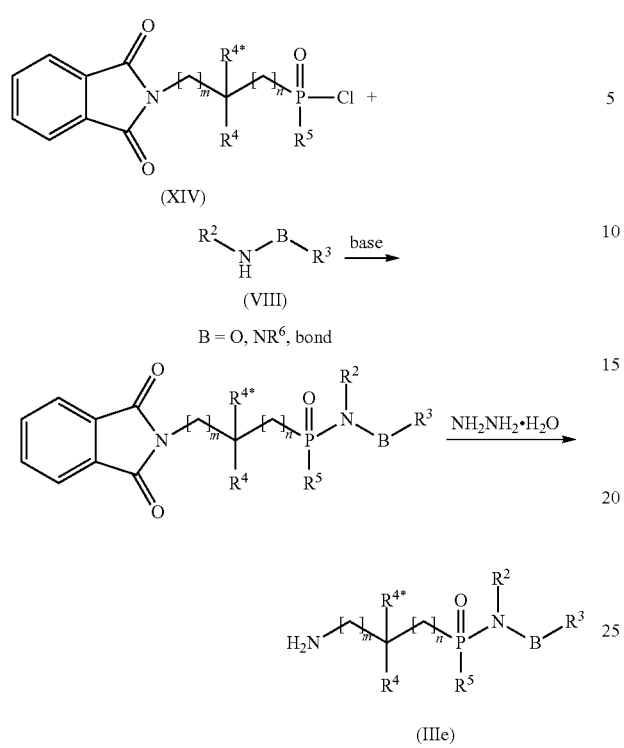

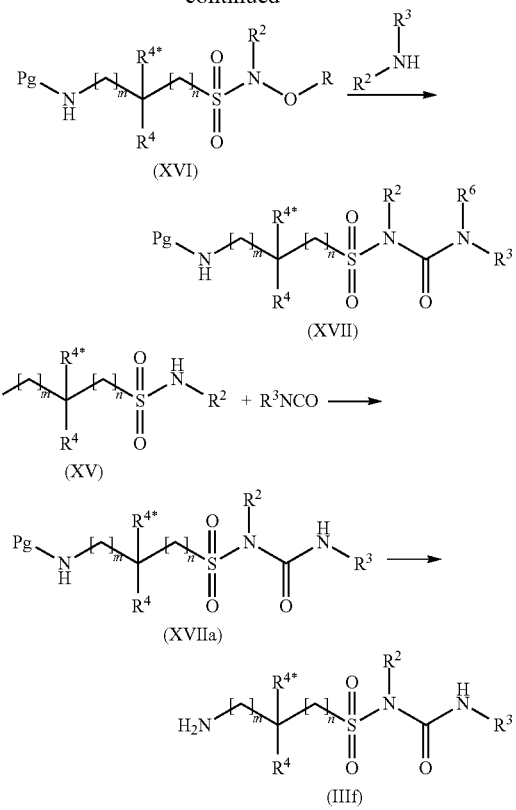

Amines of general formula (III) which are sulfonylureas (IIIf) can be prepared from known literature procedures (e.g. B. Hökfelt et al.: *J. Med. & Pharm. Chem.* (1962) 5 231-9; R. Tull et al. *JCS Section C: Organic* (1967) (8) 701-2; B. Loev: *J. Med. Chem.* (1963) 6(5) 506-8; D. R. Cassady et al.: *J. Org. Chem.* (1958) 23 923-6; D. Freitag: *Tetrahedron* (2005) 61 5615-21; Y. Kanbe et. al.: *Bioorg. Med. Chem. Lett.* (2006) 16 4090-94; I. Ubarretxena-Belandia et. al.: *Eur. J. Biochem.* (1999) 260 794-800; B. D. Roth et al.: *Bioorg. Med. Chem. Lett.* (1995) 5(20) 2367-70), for instance by reaction of suitably protected aminoalkanesulfonylchlorides (XII) with an ammonia equivalent or amine, followed by reaction with an alkyl chloroformate in the presence of a base to yield carbamates of general formula (XVI), which are subsequently allowed to react with amines $R^3R^6NH_2$ to yield sulfonylureas of general formula (XVII). Alternatively, sulfonamides of general formula (XV) can react directly with isocyanates to yield protected sulfonylureas (XVIIa). The protecting group (e.g phtalimido, Boc or other) is subsequently removed.

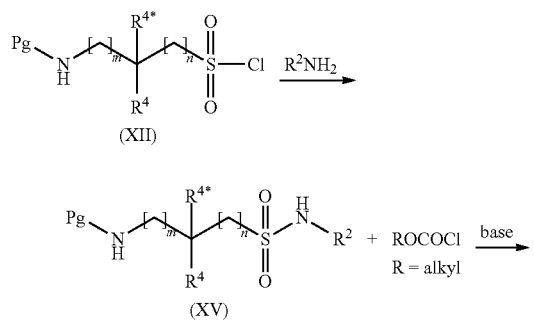

Amines of general formula (III) which are N-alkoxy- or N-aryloxy carbamates or alkyl- or arylhydrazinecarboxylates (Ig) can be obtained by reaction of protected aminoalkyl 4-nitrophenyl carbonates (XVIII) (protecting group e.g. Boc or phtalimido) with hydroxylamines or hydrazines (VIII) followed by deprotection as depicted below.

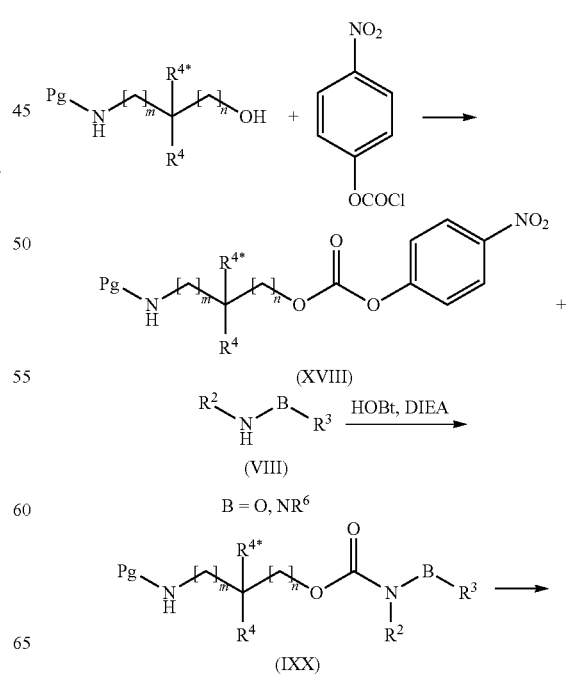

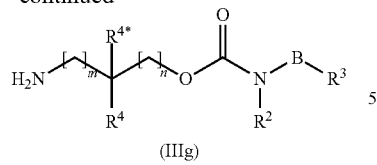

(IIIg)

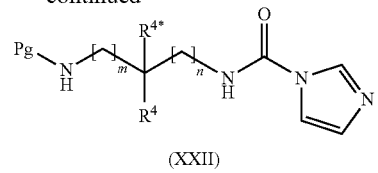

(XXII)

Amines of general formula (III) which are N-alkoxy- or N-aryloxy ureas or alkyl- or arylhydrazinecarboxamides (IIIh) can be prepared by methods known to one skilled in the art for preparing ureas. One such method is reaction of protected 4-nitrophenyl aminoalkyl carbamates (XX) (protecting group e.g. Boc or phtalimido) with hydroxylamines or hydrazines (VIII) followed by deprotection as depicted below.

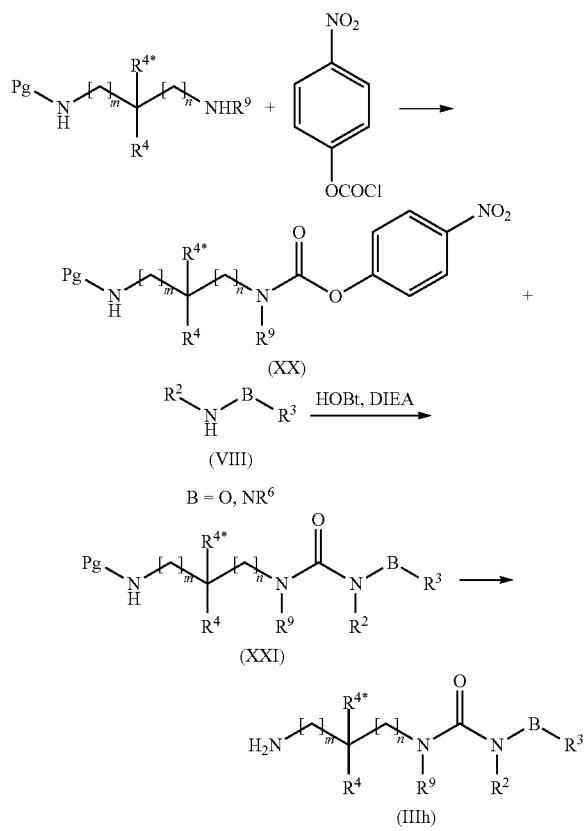

As an alternative to 4-nitrophenyl aminoalkyl carbamates (XX), N-(aminoalkyl)-1H-imidazole-1-carboxamides (XXII) may be employed.

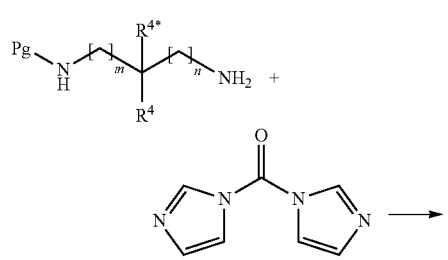

Medical Uses

The compounds of the invention is believed to be particularly useful for down-regulating NAD via inhibition of NAM-PRT, and such compounds are therefore particularly useful for treating diseases in which activation of NF-κB is implicated. Such methods are useful in the treatment of a variety of diseases including inflammatory and tissue repair disorders; particularly rheumatoid arthritis, inflammatory bowel disease, asthma and CPOD (chronic obstructive pulmonary disease), osteoarthritis, osteoporosis and fibrotic diseases; dermatosis, including psoriasis, atopic dermatitis and ultraviolet induced skin damage; autoimmune diseases including systemic lupus erythematosis, multiple sclerosis, psoriatic arthritis, ankylosing spondylitis, tissue and organ rejection, Alzheimer's disease, stroke, athersclerosis, restenosis, diabetes, glomerulonephritis, cancer, particularly wherein the cancer is selected from breast, prostate, lung, colon, cervix, ovary, skin, CNS, bladder, pancreas, leukaemia, lymphoma or Hodgkin's disease, cachexia, inflammation associated with infection and certain viral infections, including Acquired Immune Deficiency Syndrome (AIDS), adult respiratory distress syndrome, ataxia telengiectasia.

Hence, the present invention provides a compound of the formula (I) for use as a medicament; more particular for use as a medicament for the treatment of a disease or a condition caused by an elevated level of nicotinamide phosphoribosyltransferase (NAMPRT), especially for the treatment of the above-mentioned diseases and conditions.

Moreover, the invention also provides a method of inhibiting the enzymatic activity of nicotinamide phosphoribosyltransferase (NAMPRT) in a mammal, said method comprising the step of administering to said mammal a pharmaceutically relevant amount of a compound of the general formula (I).

Further, the invention provides a method of treating a disease or condition (in particular the diseases and conditions mentioned above) caused by an elevated level of nicotinamide phosphoribosyltransferase (NAMPRT) in a mammal, said method comprising the step of administering to said mammal a pharmaceutically relevant amount of a compound of the general formula (I).

In such methods, the compound may be administered in combination with a DNA damaging agent.

Formulation of Pharmaceutical Compositions

The compounds of the general formula (I) are suitably formulated in a pharmaceutical composition so as to suit the desirable route of administration.

The administration route of the compounds may be any suitable route which leads to a concentration in the blood or tissue corresponding to a therapeutic effective concentration. Thus, e.g., the following administration routes may be applicable although the invention is not limited thereto: the oral route, the parenteral route, the cutaneous route, the nasal route, the rectal route, the vaginal route and the ocular route. It should be clear to a person skilled in the art that the administration route is dependent on the particular compound in question; particularly the choice of administration route depends on the physico-chemical properties of the compound together with the age and weight of the patient and on the particular disease or condition and the severity of the same.

The compounds may be contained in any appropriate amount in a pharmaceutical composition, and are generally contained in an amount of about 1-95%, e.g. 1-10%, by weight of the total weight of the composition. The composition may be presented in a dosage form which is suitable for the oral, parenteral, rectal, cutaneous, nasal, vaginal and/or ocular administration route. Thus, the composition may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, aerosols and in other suitable form.

The pharmaceutical compositions may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988. Typically, the compounds defined herein are formulated with (at least) a pharmaceutically acceptable carrier or excipient. Pharmaceutically acceptable carriers or excipients are those known by the person skilled in the art. Formation of suitable salts of the compounds of the Formula (I) will also be evident in view of the before-mentioned.

Thus, the present invention provides in a further aspect a pharmaceutical composition comprising a compound of the general Formula (I) in combination with a pharmaceutically acceptable carrier.

Pharmaceutical compositions according to the present invention may be formulated to release the active compound substantially immediately upon administration or at any substantially predetermined time or time period after administration. The latter type of compositions is generally known as controlled release formulations.

In the present context, the term "controlled release formulation" embraces i) formulations which create a substantially constant concentration of the drug within the body over an extended period of time, ii) formulations which after a predetermined lag time create a substantially constant concentration of the drug within the body over an extended period of time, iii) formulations which sustain drug action during a predetermined time period by maintaining a relatively, constant, effective drug level in the body with concomitant minimization of undesirable side effects associated with fluctuations in the plasma level of the active drug substance (sawtooth kinetic pattern), iv) formulations which attempt to localize drug action by, e.g., spatial placement of a controlled release composition adjacent to or in the diseased tissue or organ, v) formulations which attempt to target drug action by using carriers or chemical derivatives to deliver the drug to a particular target cell type.

Controlled release formulations may also be denoted "sustained release", "prolonged release", "programmed release", "time release", "rate-controlled" and/or "targeted release" formulations.

Controlled release pharmaceutical compositions may be presented in any suitable dosage forms, especially in dosage forms intended for oral, parenteral, cutaneous nasal, rectal, vaginal and/or ocular administration. Examples include single or multiple unit tablet or capsule compositions, oil solutions, suspensions, emulsions, microcapsules, microspheres, nanoparticles, liposomes, delivery devices such as those intended for oral, parenteral, cutaneous, nasal, vaginal or ocular use.

Preparation of Solid Dosage Forms for Oral Use, Controlled Release Oral Dosage Forms, Fluid liquid compositions, parenteral compositions, controlled release parenteral compositions, rectal compositions, nasal compositions, percutaneous and topical compositions, controlled release percutaneous and topical compositions, and compositions for administration to the eye will be well-known to those skilled in the art of pharmaceutical formulation. Specific formulations can be found in "Remington's Pharmaceutical Sciences".

Capsules, tablets and pills etc. may contain for example the following compounds: microcrystalline cellulose, gum or gelatin as binders; starch or lactose as excipients; stearates as lubricants; various sweetening or flavouring agents. For capsules the dosage unit may contain a liquid carrier like fatty oils. Likewise coatings of sugar or enteric agents may be part of the dosage unit. The pharmaceutical compositions may also be emulsions of the compound(s) and a lipid forming a micellular emulsion.

For parenteral, subcutaneous, intradermal or topical administration the pharmaceutical composition may include a sterile diluent, buffers, regulators of tonicity and antibacterials. The active compound may be prepared with carriers that protect against degradation or immediate elimination from the body, including implants or microcapsules with controlled release properties. For intravenous administration the preferred carriers are physiological saline or phosphate buffered saline.

Dosages

In one embodiment, the pharmaceutical composition is in unit dosage form. In such embodiments, each unit dosage form typically comprises 0.1-500 mg, such as 0.1-200 mg, e.g. 0.1-100 mg, of the compound.

More generally, the compound are preferably administered in an amount of about 0.1-250 mg per kg body weight per day, such as about 0.5-100 mg per kg body weight per day.

For compositions adapted for oral administration for systemic use, the dosage is normally 0.5 mg to 1 g per dose administered 1-4 times daily for 1 week to 12 months depending on the disease to be treated.

The dosage for oral administration of the composition in order to prevent diseases or conditions is normally 1 mg to 100 mg per kg body weight per day. The dosage may be administered once or twice daily for a period starting 1 week before the exposure to the disease until 4 weeks after the exposure.

For compositions adapted for rectal use for preventing diseases, a somewhat higher amount of the compound is usually preferred, i.e. from approximately 1 mg to 100 mg per kg body weight per day.

For parenteral administration, a dose of about 0.1 mg to about 100 mg per kg body weight per day is convenient. For intravenous administration, a dose of about 0.1 mg to about 20 mg per kg body weight per day administered for 1 day to 3 months is convenient. For intraarticular administration, a dose of about 0.1 mg to about 50 mg per kg body weight per day is usually preferable. For parenteral administration in general, a solution in an aqueous medium of 0.5-2% or more of the active ingredients may be employed.

For topical administration on the skin, a dose of about 1 mg to about 5 g administered 1-10 times daily for 1 week to 12 months is usually preferable.

EXPERIMENTALS

General Procedures, Preparations and Examples

For nuclear magnetic resonance $^1$H NMR spectra (300 MHz) and $^{13}$C NMR (75.6) chemical shift values ($\delta$) (in ppm) are quoted, unless otherwise specified, for deuteriochloroform solutions relative to tetramethylsilane (δ=0.0) or chloroform (δ=7.25) or deuteriochloroform (δ=76.81 for $^{13}C$ NMR) standards. The value of a multiplet, either defined (dublet (d), triplet (t), double dublet (dd), double triplet (dt), quartet (q)) or not (m) at the approximate mid point is given unless a range is quoted. (bs) indicates a broad singlet.

MS was performed using an LC-MS using a Bruker Esquire 3000+ ESI Iontrap with an Agilent 1200 HPLC-system.

HPLC purifications were performed using an X-Bridge Prep C18 OBD 19×150 mm column, using a gradients of Buffer A (0.1% TFA in $H_2O$) and Buffer B (0.1% TFA in acetonitrile).

The organic solvents used were anhydrous.

The following abbreviations have been used throughout:
CDI 1,1'-carbonyldiimidazole
DCCI dicyclohexylcarbodiimide
DCM dichloromethane
DCE 1,2-dichloroethane
DIEA diisopropylehylamine
DMF N,N-dimthylformamide
DMAP N,N dimethylaminopryridine
DPT di(2-pyridyl) thionocarbonate
EDC N-(dimethylaminopropyl)-N-ethylcarbodiimide hydrochloride
EtOAc ethyl acetate
HATU O-(7-Azabenzotriazol-1-yl)-N,N,N',N'-tetramethyluronium hexafluorophosphate
HOBt 1-hydroxybenzotriazole
MS mass spectroscopy
NMM N-methylmorpholine
NMR nuclear magnetic resonance
rt room temperature
THF tetrahydrofurane
TLC thin layer chromatography General Procedure 1: Reaction of Amines of General Formula (II) with CDI Followed by Reaction with Amines of General Formula (III) to Yield Ureas of General Formula (Ia).

To a solution of CDI (1.1 eq.) in THF was added amine of general formula (II) (1.0 eq.) and the mixture was stirred at rt overnight. To the reaction mixture amine of general formula (III) (1.0 eq.) was added and the reaction was stirred at rt overnight. The solvent was evaporated in vacuum and the residue was purified by chromatography (chloroform:methanol:$NH_3$ (25% aq.) 96:4:0.4 or with MeCN—$H_2O$—AcOH 3:1:1) to yield urea of general formula (Ia).

The oxalic acid salt of urea of general formula (Ia) may be obtained by dissolving compound of general formula (Ia) (1 eq.) in MeCN and adding a solution of oxalic acid (2 eq.) in MeCN. The precipitate was filtered and dried to give the oxalic acid salt of urea of general formula (Ia).

The HCl-salt of urea of general formula (Ia) may be obtained by dissolving compound of general formula (Ia) (1 eq) in 1N HCl/MeOH (2 eq.), the solvent was evaporated, the residue was washed with DCM followed by $Et_2O$ and dried to give the HCl-salt of urea of general formula (Ia).

General Procedure 2: Reaction of Amines of General Formula (II) with 4-Nitrophenyl Cholroformate Followed by Reaction with Amines of General Formula (III) to Yield Ureas of General Formula (Ia).

Amine of general formula (II) (1.0 eq.) was dissolved in EtOAc, DIEA (1.2 eq.) was added, the mixture was cooled on an icebath and 4-nitrophenyl chloroformate (1.1 eq.) was added with stirring. After 4 h (or consumption of the amine (II)) the reaction mixture was washed successively with 5% Na2CO3 (twice), H2O, brine, dried over $Mg_2SO_4$, filtered and concentrated. The resulting 4-nitrophenyl carbamate (1.0 eq.) was dissolved in DMF, amine of general formula (III) (1.0 eq.) was added followed by HOBT (2.0 eq) and DIEA (0.5 eq.) and heated at 40° C. overnight. The mixture was concentrated and purified by chromatography (chloroform: methanol:NH3 (25% aq.)98:2:0.2 to 96:4:0.4) to afford urea of general formula (Ia).

The oxalic acid salt of urea of general formula (Ia) may be obtained by dissolving compound of general formula (Ia) (1 eq.) in MeCN and adding a solution of oxalic acid (2 eq.) in MeCN. The precipitate was filtered and dried to give the oxalic acid salt of urea of general formula (Ia).

General Procedure 3: Reaction of Amines of General Formula (II) with DPT Followed by Reaction with Amines of General Formula (III) to Yield Thioureas of General Formula (Ib)

Amine of general formula (II) (1.0 eq.) was dissolved in THF, the reaction mixture was cooled on an icebath and NaH (1.1 eq.) was added with stirring. After 2 h DPT (1.0 eq.) was added and the mixture gradually allowed to reach rt. After a further 3 h (or consumption of the starting materials) the resulting isothiocyanate was either purified by chromatography (mixtures of petroleum ether and ETOAc) or used directly.

To a solution in THF of the isothiocyanate (1.0 eq.) was added amine of general formula (III) (1.0 eq.) and DIEA (1.1 eq.) and the mixture was stirred at rt overnight, concentrated and purified by chromatography (1-5% methanol in DCM) to afford thiourea of general formula (Ib).

The oxalic acid salt of thiourea of general formula (Ib) may be obtained by dissolving compound of general formula (Ib) (1 eq.) in MeCN and adding a solution of oxalic acid (2 eq.) in MeCN. The precipitate was filtered and dried to give the oxalic acid salt of urea of general formula (Ib).

General Procedure 4: Reaction of 4-Nitrophenoxycarbamates of General Formula (XX) with Hydroxylamines or Hydrazines (VIII) and Subsequent Deprotection.

4-nitrophenoxycarbamate of general formula (XX) (1.0 eq.) was dissolved in DMF, the hydroxylamine or hydrazine (2.0 eq.), HOBt (2 eq.) and DIEA (0.5 eq., or 1.5 eq. if the hydroxylamine or hydrazine is a salt) were added, and the mixture heated to 50 0° C. with stirring for 4 h or until consumption of the carbamate. The mixture was concentrated and purified by chromatography (1-5% MeOH in DCM). The resulting Boc-protected compound of general formula (XXIa) was dissolved in MeOH and 3N HCl in MeOH was added with stirring. After 2 h the mixture was concentrated and the compound used directly as the HCl-salt or purified by chromatography (chloroform:methanol:$NH_3$ (25% aq.) 95:5: 1) to afford compounds of general formula (IIIh).

General Procedure 5: Preparation of Amines of General Formula (IIIc) by Reaction of Phtalimidoalkanesulfonylchlorides (XII) with Hydroxylamines, Amines or Hydrazines (VIII) and Subsequent Deprotection.

Phtalimidoalkanesulfonylchloride (XII) (1.0 eq.) (prepared as described in the literature, e.g. G. J. Atwell et al.: *J. Med. Chem.* (1977) 20(9) 1128-134; J. Humljan et al.: *Tet. Letters,* 46 4069-4072) was added in small portions to a solution of hydroxylamine, amine or hydrazine (VIII) (1.02 eq.) and triethyamine or N-methylmorpholine (1.1 eq., or 2.2 eq. if the hydroxylamine or amine is a salt) in DCM at −20° C. with stirring. The mixture was gradually allowed to reach rt, stirred overnight, concentrated. purified by chromatography (1% methanol in DCM or mixtures of petroleum ether and EtOAc) to yield phtalimido-protected intermediates.

Deprotection: the phtalimido protected intermediate (1.0 eq.) was dissolved in ethanol, hydrazine hydrate (2.9 eq.) was added and the mixture heated in a microwave oven at 120° C.

until consumption of the starting material (typically 10-30 min). The mixture was filtered, the filter cake washed with ethanol, the filtrate was concentrated and purified by chromatography (chloroform:methanol:NH3 (25% aq.) 98:2:02 or 90:10:1) to afford amines of general formula (IIIc).

Preparation 1: tert-butyl 5-((4-nitrophenoxy)carbonylamino)pentylcarbamate (Compound 1)

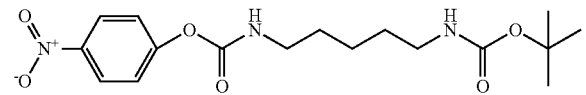

tert-Butyl 5-aminopentylcarbamate (2.02 g, 10 mmol) was dissolved in EtOAc, 4-nitrophenyl carbonochloridate (2.22 g, 11 mmol) was added, the mixture cooled on an icebath, DIEA (2.05 mL, 12 mmol) was added with stirring and the mixture gradually allowed to reach rt and stirred for 3 h. The mixture was transferred to a separatory funnel with EtOAc and $H_2O$, and shaken. The organic phase was extracted with 1N HCl, $H_2O$, 5% $NH_2CO_3$, $H_2O$ (three times), brine, dried over $Mg_2SO_4$, filtered and concentrated to yield compound 9.

1H-NMR (CDCl$_3$): δ 8.24 (m, 2H), 7.39 (m, 2H), 5.32 (bs, 1H), 4.56 (bs, 1H), 3.29 (q, 2H), 3.14 (m, 2H), 1.7-1.3 (m, 6H), 1.44 (s, 9H).

Preparation 2: N-(5-aminopentyl)morpholine-2-carboxamide hydrochloride (Compound 2)

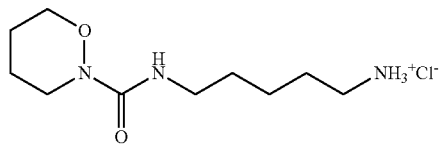

General procedure 4. Starting materials: compound 1 and tetrahydro-1,2-oxazinium (*J. Chem. Soc., Perkin Trans* 2 (2000), 1435-144).

$^1$H-NMR (CD$_3$OD): δ 3.94 (m, 2H), 3.52 (m, 2H), 3.17 (t, 2H), 2.90 (t, 2H), 1.75-1.60 (m, 6H), 1.54 (m, 2H), 1.39 (m, 2H).

Preparation 3: 3-(5-aminopentyl)-1-cyclohexyl-1-(2-morpholinoethoxy)urea dihydrochloride (Compound 3)

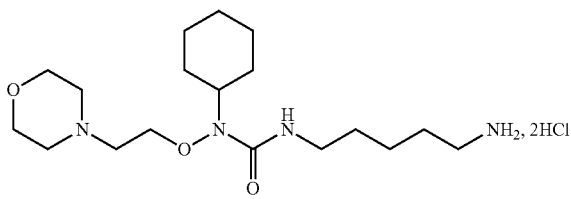

General procedure 4. Starting materials: compound 1 and N-cyclohexyl-O-(2-morpholinoethylhydroxylamine (see, e.g., WO 2009/086835).

$^1$H-NMR (DMSO-d$_6$): δ 11.44 (bs, 1H), 7.97 (bs, 3H), 4.22 (t, 2H), 4.09 (t, 2H), 3.97 (m, 2H), 3.83 (m, 2H), 3.72 (m, 1H), 3.40 (m, 4H), 3.14 (m, 2H), 2.77 (m, 2H), 1.8-1.0 (m, 16).

Preparation 4: 3-(5-aminopentyl)-1-isopropyl-1-(2-morpholinoethoxy)urea dihydrochloride (Compound 4)

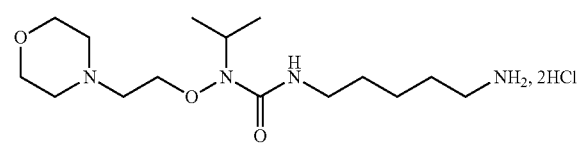

General procedure 4. Starting materials: compound 1 and N-isopropyl-O-(2-morpholinoethylhydroxylamine (see, e.g., WO 2009/086835).

$^1$H-NMR (CD$_3$OD): δ 4.28 (t, 2H), 4.20 (m, 1H), 4.09 (m, 2H), 3.95 (m, 2H), 3.56 (m, 4H), 3.26 (m, 4H), 2.95 (t, 2H), 1.71 (m, 2H), 1.63 (m, 2H), 1.45 (m, 2H), 1.23 (d, 6H).

EXAMPLES

Example 1

N-(cyclohexylmethoxy)-6-(3-pyridin-4-ylureido)hexane-1-sulfonamide (Compound 1001)

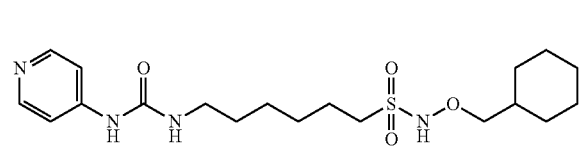

General procedure 1. Starting materials: 4-aminopyridine and 6-amino-N-(cyclohexylmethoxy)hexane-1-sulfonamide (see, e.g., WO 2009/086835).

$^1$H-NMR (CD$_3$OD): δ 8.28 (m, 2H), 7.46 (m, 2H), 3.75 (d, 2H), 3.22 (m, 4H), 1.9-1.15 (m, 17 H), 0.99 (m, 2H).

Example 2

N-Cyclohexyl-N-(2-morpholinoethoxy)-7-(3-pyridin-4-ylureido)heptanamide (Compound 1002)

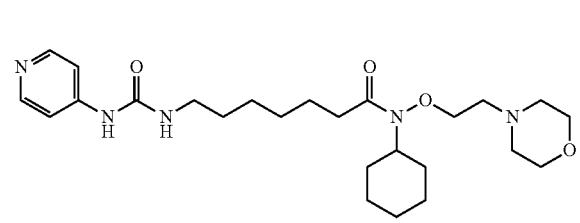 [SMILES: O=C(NCCCCCCC(=O)N(OCCN1CCOCC1)C1CCCCC1)Nc1ccncc1]

General procedure 1. Starting materials: 4-aminopyridine and 7-amino-N-cyclohexyl-N-(2-morpholinoethoxy)heptanamide (see, e.g., WO 2009/086835).

MS [M+H]⁺=476.3, [M−H]⁻=574.3.3, [M−H+HCOOH]⁻=520.5.

Example 3

N-(cyclohexylmethoxy)-6-(3-pyrimidin-4-ylthioureido)hexane-1-sulfonamide (Compound 1003)

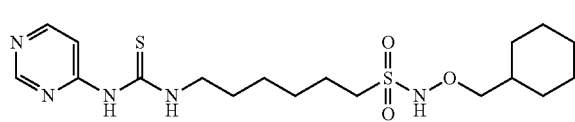 [SMILES: O=S(=O)(CCCCCCNC(=S)Nc1ccncn1)NOCC1CCCCC1]

General procedure 3. Starting materials: 4-aminopyrimidine and 6-amino-N-(cyclohexylmethoxy)hexane-1-sulfonamide (see, e.g., WO 2009/086835).
MS [M+H]⁺=430.2, [M−H]⁻=528.3.

Example 4

N-(cyclohexylmethoxy)-6-(3-(pyridin-4-ylmethyl)ureido)hexane-1-sulfonamide (Compound 1004)

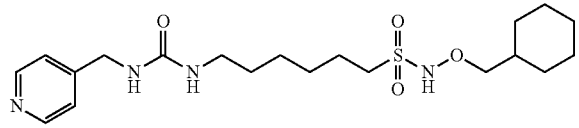 [SMILES: O=C(NCCCCCCS(=O)(=O)NOCC1CCCCC1)NCc1ccncc1]

General procedure 2. Starting materials: 4-picolylamine and 6-amino-N-(cyclohexylmethoxy)hexane-1-sulfonamide (see, e.g., WO 2009/086835).
¹H-NMR (CD₃OD): 8.47 (m, 2H), 7.36 (m, 2H), 4.39 (s, 2H), 3.75 (d, 2H), 3.16 (m, 4H), 1.9-1.15 (m, 17 H), 1.00 (m, 2H).

Example 5

N-Cyclohexyl-N-(2-morpholinethoxy)-6-(3-pyridin-4-ylthioureido)hexane-1-sulfonamide oxalate (Compound 1005)

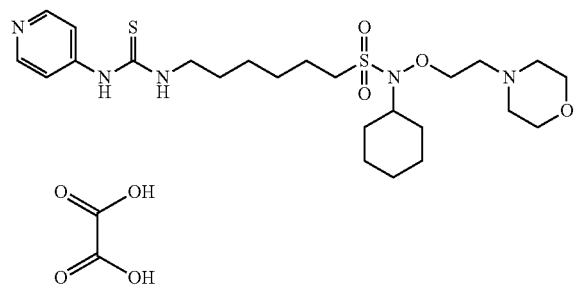

General procedure 3. Starting materials: 4-aminopyridine and 6-amino-N-cyclohexyl-N-(2-morpholinoethoxy)hexane-1-sulfonamide (see, e.g., WO 2009/086835).
¹H-NMR (200 MHz) (DMSO-d₆): 10.99 (bs, 1H), 9.21 (t, 1H), 8.44 (d, 2H), 7.88 (d, 2H), 4.11 (t, 2H), 3.74-3.60 (m, 4H), 3.58-3.39 (m, 3H), 3.42 (t, 2H), 2.90 (t, 2H), 2.83-2.67 (m, 4H), 1.96-1.65 (m, 5H), 1.90-1.65 (13 H).

Example 6

N-Cyclohexyl-N-(2-morpholinethoxy)-7-(3-pyrimidin-4-ylthioureido)heptanamide (Compound 1006)

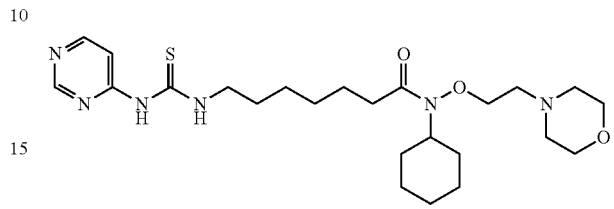

General procedure 3. Starting materials: 4-aminopyrimidine and 7-amino-N-cyclohexyl-N-(2-morpholinoethoxy)heptanamide (see, e.g., WO 2009/086835).
¹H-NMR (CD₃OD): δ 8.79 (bs, 1H), 8.48 (m, 1H), 7.01 (m, 1H), 4.10 (m, 1H), 4.08 (t, 2H), 3.71 (m, 6H), 2.67 (t, 2H), 2.56 (m, 4H), 2.51 (t, 2H), 1.95-1.05 (m, 18H).

Example 7

1-(6-(morpholinosulfonyl)hexyl)-3-(pyridin-4-yl)urea hydrochloride (Compound 1007)

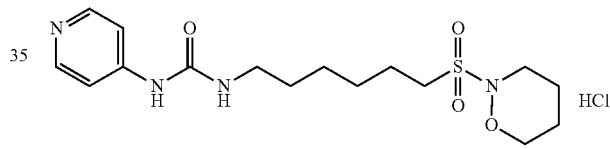

General procedure 1. Starting materials: 4-aminopyridine and 6-(morpholinosulfonyl)hexane-1-amine (see, e.g., WO 2009/086835).
¹H-NMR (200 MHz) (DMSO-d₆): δ 14.36 (bs, 1H), 10.85 (bs, 1H), 8.51 (d, 2H), 7.84 (d, 2H), 7.22 (bs, 1H), 4.03 (t, 2H), 3.02-3.44 (m, 6H), 1.90-1.54 (m, 6H), 1.54-1.21 (m, 6H).

Example 8

N-Cyclohexyl-N-(2-morpholinethoxy)-6-(3-pyridin-4-ylureido)hexane-1-sulfonamide oxalate (Compound 1008)

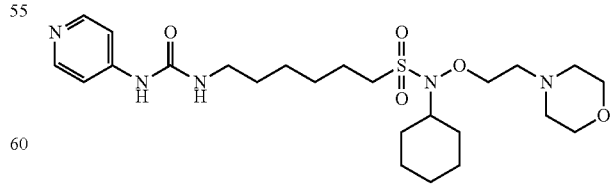

General procedure 1. Starting materials: 4-aminopyridine and 6-amino-N-cyclohexyl-N-(2-morpholinoethoxy)hexane-1-sulfonamide (see, e.g., WO 2009/086835).

$^{1}$H-NMR (200 MHz) (DMSO-$d_6$): 10.25-9.50 (bs, 1H), 8.36 bs, 2H), 7.56 (bs, 2H), 7.23-6.78 (m, 1H), 4.40-3.92 (m, 6H), 3.40-3.70 (m, 3H), 3.35-2.97 (m, 4H), 2.80-2.59 (m, 4H), 2.00-1.64 (m, 5H), 1.64-0.91 (m, 13H).

Example 9

N-cyclohexyl-N-(2-morpholinoethoxy)-7-(3-(pyridin-3-ylmethyl)ureido)heptanamide (Compound 1009)

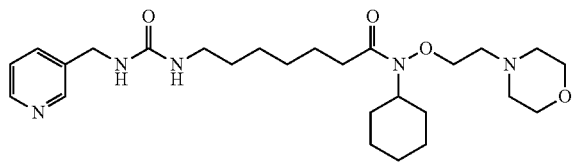 [SMILES: O=C(NCCCCCCC(=O)N(OCCN1CCOCC1)C1CCCCC1)NCc1cccnc1]

General procedure 2. Starting materials: 3-picolylamine and 7-amino-N-cyclohexyl-N-(2-morpholinoethoxy)heptanamide (see, e.g., WO 2009/086835).

$^{1}$H-NMR (CD$_3$OD): δ 8.50 (d, 1H), 8.43 (dd, 1H), 7.80 (dt, 1H), 7.41 (m, 1H), 4.37 (s, 2H), 4.14 (bs, 1H), 4.08 (t, 2H), 3.72 (m, 4H), 3.15 (t, 2H), 2.68 (t, 2H), 2.56 (m, 4H), 2.49 (t, 2H), 1.95-1.1 (18 H).

Example 10

N-cyclohexyl-N-(2-morpholinoethoxy)-7-(3-(pyridin-4-ylmethyl)ureido)heptanamide (Compound 1010)

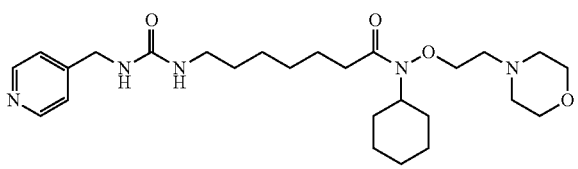 [SMILES: O=C(NCCCCCCC(=O)N(OCCN1CCOCC1)C1CCCCC1)NCc1ccncc1]

General procedure 2. Starting materials: 4-picolylamine and 7-amino-N-cyclohexyl-N-(2-morpholinoethoxy)heptanamide (see, e.g., WO 2009/086835).

$^{1}$H-NMR (CD$_3$OD)): δ 8.47 (m, 2H), 7.36 (m, mH), 4.379 (s, 2H), 4.14 (bs, 1H), 4.08 (t, 2H), 3.72 (m, 4H), 3.16 (t, 2H), 2.67 (t, 2H), 2.56 (m, 4H), 2.50 (t, 2H), 1.95-1.05 (18 H).

Example 11

6-(3-1,2,4-triazin-3-ylthioureido)-N-(cyclohexylmethoxy)hexane-1-sulfonamide (Compound 1011)

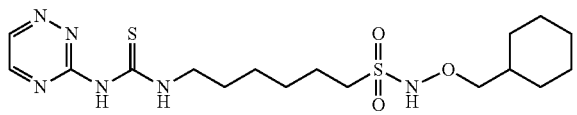 [SMILES: O=S(=O)(CCCCCCNC(=S)Nc1nccnn1)NOCC1CCCCC1]

General procedure 3. Starting materials: 1,2,4-triazin-3-amine and 6-amino-N-(cyclohexylmethoxy)hexane-1-sulfonamide (see, e.g., WO 2009/086835).

$^{1}$H-NMR (DMSO-$d_6$): δ 11.12 (bs, 1H), 10.96 (t, 1H), 9.97 (bs, 1H), 9.08 (d, 1H), 8.72 (d, 1H), 3.65 (m, 4H), 3.12 (m, 2H), 1.65 (m, 10 H), 1.41 (m, 4H), 1.16 (m, 3H), 0.90 (m, 2H).

Example 12

7-(3-1,2,4-triazin-3-ylthioureido)-N-cyclohexyl)-N-(2-morpholinoethoxy)heptanamide (Compound 1012)

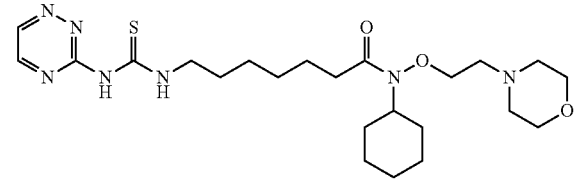 [SMILES: O=C(CCCCCCNC(=S)Nc1nccnn1)N(OCCN1CCOCC1)C1CCCCC1]

General procedure 3. Starting materials: 1,2,4-triazin-3-amine and 7-amino-N-cyclohexyl-N-(2-morpholinoethoxy)heptanamide (see, e.g., WO 2009/086835).

$^{1}$H-NMR (CD$_3$OD): δ 8.98 (d, 2H), 8.63 (d, 2H), 4.14 (bs, 1H), 3.76 (t, 2), 3.72 (m, 4H), 2.68 (t, 2H), 2.57 (m, 4H), 2.51 (m, 2H), 1.9-1.25 (m, 17H), 1.20 (m, 1H).

Example 13

N-(cyclohexylmethoxy)-N-(2-(2-(2-methoxyethoxy)ethoxy)ethyl)-6-(3-(pyridin-3-ylmethyl)ureido)hexane-1-sulfonamide (Compound 1013)

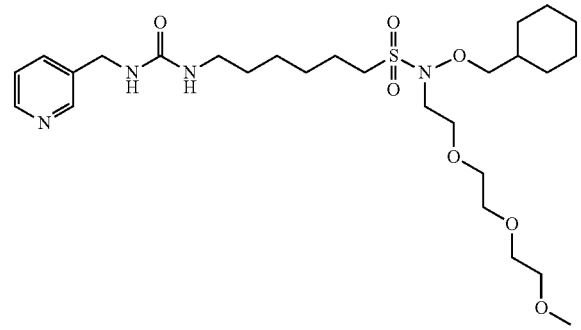 [SMILES: COCCOCCOCCN(OCC1CCCCC1)S(=O)(=O)CCCCCCNC(=O)NCc1cccnc1]

General procedure 2. Starting materials: 3-picolylamine and 6-amino-N-(cyclohexylmethoxy)-N-(2-(2-(2-methoxyethoxy)ethoxy)ethy)hexane-1-sulfonamide (see, e.g., WO 2009/086835).

$^{13}$C-NMR (CD$_3$OD): δ 160.99, 148.94, 148.38, 137.47, 125.26, 83.80, 73.00, 71.59, 71.42, 71.38, 68.74, 59.14, 53.53, 46.11, 42.18, 40.92, 38.37, 31.04, 29.29, 27.56, 27.39, 26.88, 23.53.

Example 14

N-(cyclohexylmethoxy)-6-(3-(pyridin-3-ylmethyl)ureido)hexane-1-sulfonamide (Compound 1014)

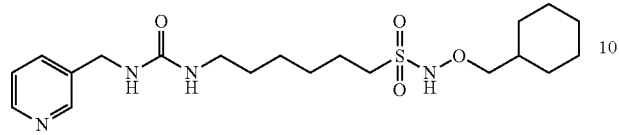

General procedure 2. Starting materials: 3-picolylamine and 6-amino-N-(cyclohexylmethoxy)hexane-1-sulfonamide (see, e.g., WO 2009/086835).

$^1$H-NMR (CD$_3$OD): δ 8.49 (bs, 1H), 8.43 (d, 1H), 7.79 (dt, 1H), 7.41 (m, 1H), 4.37 (s, 2H), 3.75 (d, 2H), 3.16 (m, 4H), 1.85-1.1 (m, 17), 1.00 (m, 2H).

Example 15

N-cyclohexyl-N-(2-morpholinoethoxy)-7-(3-(pyridin-3-ylmethyl)thioureido)heptanamide (Compound 1015)

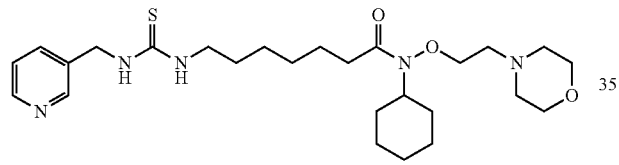

General procedure 3. Starting materials: 3-picolylamine and 7-amino-N-cyclohexyl-N-(2-morpholinoethoxy)heptanamide (see, e.g., WO 2009/086835).

$^1$H-NMR (CD$_3$OD): δ 8.52 (bs, 1H), 8.43 (d, 1H), 7.85 (m, 1H), 7.42 (m, 1H), 4.82 (s, 2H), 4.13 (bs, 1H), 4.08 (t, 2H), 3.72 (m, 4H), 3.46 (m, 2H), 2.68 (m, 2H), 2.56 (m, 4H), 2.49 (t, 2H), 1.95-1.1 (m, 18 H).

Example 16

N-(cyclohexylmethoxy)-6-(3-(3,5-dimethylisoxazol-4-yl)thioureido)hexane-1-sulfonamide (Compound 1016)

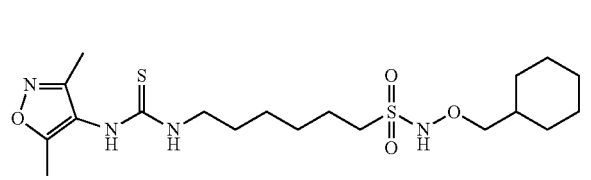 [SMILES: Cc1noc(C)c1NC(=S)NCCCCCCS(=O)(=O)NOCC1CCCCC1]

General procedure 3. Starting materials: 3,5-dimethylisoxazol-4-amine and 6-amino-N-(cyclohexylmethoxy)hexane-1-sulfonamide (see, e.g., WO 2009/086835).

$^1$H-NMR (DMSO-d$_6$): δ 9.96 (s, 1H), 8.67 (bs, 1H), 7.74 (bs, 1H), 3.66 (d, 2H), 3.42 (m, 2H), 3.11 (m, 2H), 2.21 (s, 3H), 2.06 (s, 3H), 1.80-0.8 (m, 19).

Example 17

N-Cyclohexyl-7-(3-(3,5-dimethylisoxazol-4-yl)thioureido)-N-(2-morpholinoethoxy)heptanamide (Compound 1017)

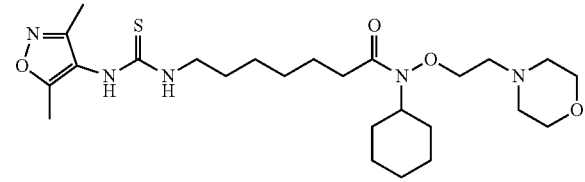 [SMILES: Cc1noc(C)c1NC(=S)NCCCCCCC(=O)N(OCCN1CCOCC1)C1CCCCC1]

General procedure 3. Starting materials: 3,5-dimethylisoxazol-4-amine and 7-amino-N-cyclohexyl-N-(2-morpholinoethoxy)heptanamide (see, e.g., WO 2009/086835).

$^1$H-NMR (DMSO-d$_6$): δ 8.65 (bs, 1H), 7.73 (bs, 1H), 4.03 (bs, 1H), 3.95 (t, 2H), 3.57 (m, 4H), 3.40 (m, 2H), 2.53 (m, 2H), 2.43 (m, 4H), 2.39 (t, 2H), 2.21 (s, 3H), 2.05 (s, 3H), 1.8-1.1 (m, 18 H).

Example 18

1-(6-morpholinosulfonyl)hexyl)-3-(pyridin-3-ylmethyl)urea hydrochloride (Compound 1018)

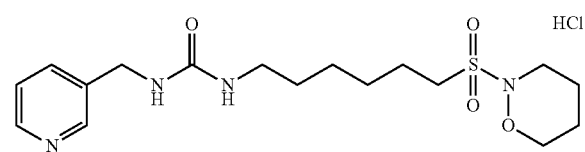 [SMILES: Cl ; O=C(NCCCCCCS(=O)(=O)N1CCCCO1)NCc1cccnc1]

General procedure 1. Starting materials: 3-picolylamine and 6-(morpholinosulfonyl)hexane-1-amine (see, e.g., WO 2009/086835).

$^1$H-NMR (400 MHz) (DMSO-d$_6$): δ 8.75-8.67 (m, 2H), 8.27 (m, 1H), 7.88 (m, 1H), 6.59 (bs, 1H), 6.22 (bs, 1H), 4.34 (s, 2H), 4.03 (t, 2H), 3.27 (m, 2H), 3.18 (m, 2H), 2.98 (t, 2H), 1.79 (m, 2H), 1.69 (m, 2H), 1.61 (m, 2H), 1.44-1.31 (m, 4H), 1.20-1.31 (m, 2H).

Example 19

N-(cyclohexylmethoxy)-6-(3-Pyrazin-2-ylthioureido)hexane-1-sulfonamide (Compound 1019)

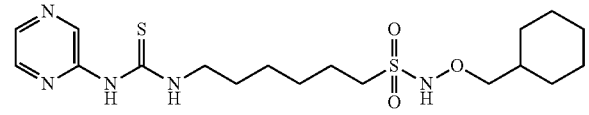 [SMILES: O=S(=O)(CCCCCCNC(=S)Nc1cnccn1)NOCC1CCCCC1]

General procedure 3. Starting materials: pyrazin-2-amine and 6-amino-N-(cyclohexylmethoxy)hexane-1-sulfonamide (see, e.g., WO 2009/086835).

$^1$H-NMR (CD$_3$OD): δ 8.38 (d, 1H), 8.24 (m, 1H), 8.19 (d, 1H), 3.74 (m, 4H), 3.20 (m, 2H), 1.9-1.4 (m, 13), 1.26 (m, 4H), 0.99 (m, 2H).

Example 20

N-cyclohexyl-N-(2-morpholinoethoxy)-7-(3-(2-pyridin-3-yl)ethyl)ureido)heptanamide (Compound 1020)

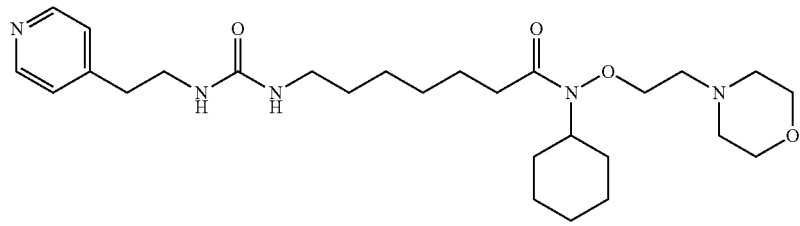

General procedure 2. Starting materials: 2-(pyridin-3-yl)ethanamine and 7-amino-N-cyclohexyl-N-(2-morpholinoethoxy)heptanamide (see, e.g., WO 2009/086835).

$^1$H-NMR (CD$_3$OD): δ 8.42 (d, 1H), 8.40 (dd, 1H), 7.75 (dt, 1H), 7.39 (m, 1H), 4.15 (bs, 1H), 4.08 (t, 2H), 3.72 (m, 4H), 3.39 (t, 2H), 3.10 (t, 2H), 2.83 (t, 2H), 2.67 (m, 2H), 2.56 (m, 4H), 2.49 (t, 2H), 1.95-1.05 (m, 18 H).

Example 21

N-cyclohexyl-N-(2-morpholinoethoxy)-7-(3-(2-pyridin-4-yl)ethyl)ureido)heptanamide (Compound 1021)

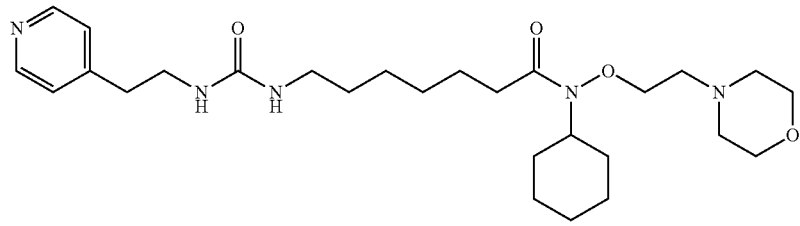

General procedure 2. Starting materials: 2-(pyridin-4-yl)ethanamine and 7-amino-N-cyclohexyl-N-(2-morpholinoethoxy)heptanamide (see, e.g., WO 2009/086835).

$^1$H-NMR (CD$_3$OD): δ 8.44 (m, 2H), 7.33 (m, 2H), 4.15 (bs, 1H), 4.08 (t, 2H), 3.72 (m, 4H), 3.42 (t, 2H), 3.10 (t, 2H), 2.85 (t, 2H), 2.67 (m, 2H), 2.56 (m, 4H), 2.49 (t, 2H), 1.95-1.25 (m, 17 H), 1.10 (m, 1H).

Example 22

N-Isopropyl-N-(2-morpholinoethoxy)-6-(3-(pyridin-3-ylmethyl)ureido)hexane-1-sulfonamide (Compound 1022)

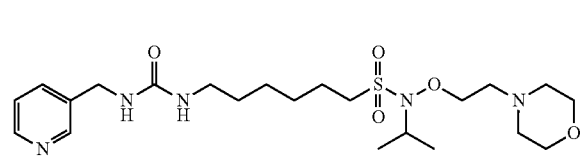 [SMILES: CC(C)N(OCCN1CCOCC1)S(=O)(=O)CCCCCCNC(=O)NCc1cccnc1]

General procedure 2. Starting materials: 3-picolylamine and 6-amino-N-isopropyl-N-(2-morpholinoethoxy)hexane-1-sulfonamide (see, e.g., WO 2009/086835).

$^1$H-NMR (CD$_3$OD): δ 8.49 (d, 1H), 8.43 (dd, 1H), 7.79 (dt, 1H), 7.41 (m, 1H), 4.37 (s, 2H), 4.18 (t, 2H), 3.98 (m, 1H), 3.71 (m, 4H), 3.22 (m, 2H), 3.16 (t, 2H), 2.66 (m, 2H), 2.55 (m, 4H), 1.87 (m, 2H), 1.51 (m, 4H), 1.41 (m, 2H), 1.29 (d, 6 H).

Example 23

N-(5-(3-(pyridin-3-ylmethyl)ureido)pentyl)morpholine-2-carboxamide (Compound 1023)

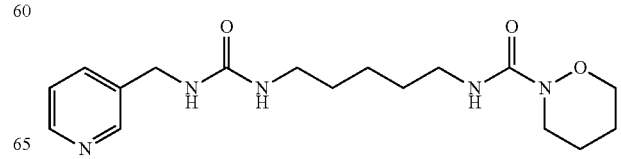

General procedure 2. Starting materials: 3-picolylamine and compound 2.

¹H-NMR (CD₃OD): δ 8.50 (d, 1H), 8.43 (dd, 1H), 7.79 (dt, 1H), 7.42 (m, 1H), 6.98 (t, 1H), 4.37 (s, 2H), 3.97 (m, 2H), 3.55 (m, 2H), 3.16 (m, 4H), 1.73 (m, 4H), 1.53 (m, 4H), 1.37 (m, 2H).

Example 24

N-(5-(3-pyridin-4-ylureido)pentyl)morpholine-2-carboxamide (Compound 1024)

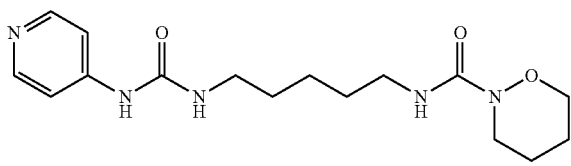 [SMILES: O=C(NCCCCCNC(=O)N1CCCCO1)Nc1ccncc1]

General procedure 1. Starting materials 4-aminopyridine and compound 2.

¹H-NMR (CD₃OD): δ 8.28 (m, 2H), 7.47 (m, 2H), 3.96 (t, 2H), 3.55 (t, 2H), 3.22 (m, 4H), 1.72 (m, 4H), 1.57 (m, 4H), (m, 2H).

Example 25

N-Cyclohexyl-N-(3-morpholinopropyl)-6-(3-(pyridin-3-ylmethyl)ureido)hexane-1-sulfonamide (Compound 1025)

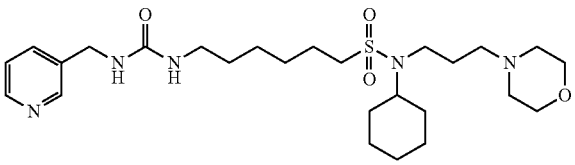 [SMILES: O=C(NCCCCCCS(=O)(=O)N(CCCN1CCOCC1)C1CCCCC1)NCc1cccnc1]

General procedure 2. Starting materials: 3-picolylamine and 6-amino-N-cyclohexyl-N-(3-morholinopropyl)hexane-1-sulfonamide (see, e.g., WO 2009/086835).

¹H-NMR (CD₃OD): δ 8.50 (d, 1H), 8.43 (dd, 1H), 7.79 (dt, 1H), 7.42 (m, 1H), 4.37 (s, 2H), 3.71 (m, 4H), 3.52 (m, 1H), 3.24 (m, 2H), 3.15 (t, 2H), 3.02 (m, 2H), 2.49 (m, 4H), 2.40 (t, 2H), 1.9-1.25 (m, 19H), 1.18 (m, 1H).

Example 26

N-Cyclohexyl-N-(3-morpholinopropyl)-6-(3-pyridin-4-ylureido)hexane-1-sulfonamide (Compound 1026)

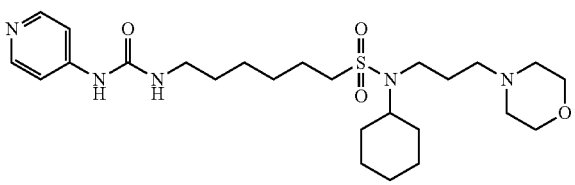 [SMILES: O=C(NCCCCCCS(=O)(=O)N(CCCN1CCOCC1)C1CCCCC1)Nc1ccncc1]

General procedure 1. Starting materials: 4-aminopyridine and 6-amino-N-cyclohexyl-N-(3-morholinopropyl)hexane-1-sulfonamide (see, e.g., WO 2009/086835).

¹H-NMR (CD₃OD): δ 8.28 (m, 2H), 7.46 (m, 2H), 3.70 (m, 4H), 3.51 (m, 1H), 3.23 (m, 4H), 3.03 (m, 2H), 2.47 (m, 4H), 2.37 (t, 2H), 1.82 (m, 8H), 1.7-1.25 (m, 11H), 1.17 (m, 1H).

Example 27

N-cyclohexyl-N-(2-morpholinoethoxy)-7-(3-Pyrazin-2-ylthioureido)heptanamide (Compound 10127)

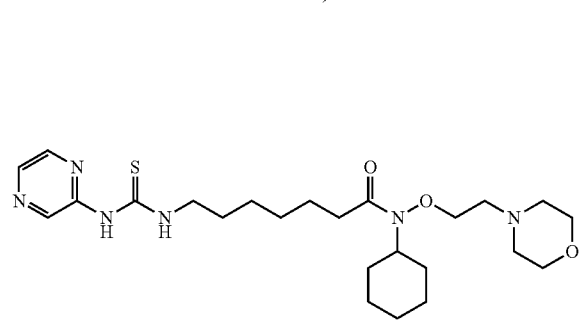

General procedure 3. Starting materials: pyrazin-2-amine and 7-amino-N-cyclohexyl-N-(2-morpholinoethoxy)heptanamide (see, e.g., WO 2009/086835).

¹H-NMR (CD₃OD): δ 8.38 (d, 1H), 8.23 (dd, 1H), 8.20 (d, 1H), 4.14 (bs, 1H), 4.07 (t, 2H), 3.71 (m, 6H), 2.67 (t, 2H), 2.55 (m, 4H), 2.51 (t, 2H), 1.9-1.25 (m, 17 H), 1.20 (m, 1H).

Example 28

N-(cyclohexylmethoxy)-N-(2-(2-(2-methoxyethoxy)ethoxy)ethyl)-6-(3-(pyridin-3-ylmethyl)thioureido)hexane-1-sulfonamide (Compound 1028)

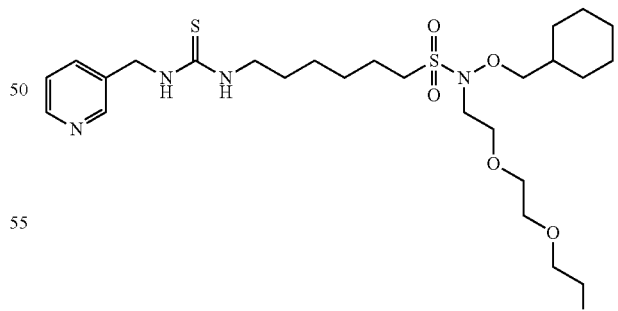

General procedure 3. Starting materials: 3-picolylamine and 6-amino-N-(cyclohexylmethoxy)-N-(2-(2-(2-methoxyethoxy)ethoxy)ethy)hexane-1-sulfonamide (see, e.g., WO 2009/086835).

¹H-NMR (CD₃OD): δ 8.53 (d, 1H), 8.44 (dd, 1H), 7.85 (dt, 1H), 7.42 (m, 1H), 4.82 (s, 2H), 3.87 (d, 2H), 3.72 (t, 2H), 3.66

(m, 6H), 3.6-3.4 (m, 6H), 3.37 (s, 3H), 3.18 (m, 2H), 1.87 (m, 2H), 1.85-1.15 (m, 15H), 1.05 (m, 2H).

Example 29

N-(cyclohexylmethoxy)-N-(2-(2-(2-methoxyethoxy)ethoxy)ethyl)-6-(3-pyridin-4-ylureido)hexane-1-sulfonamide (Compound 1029)

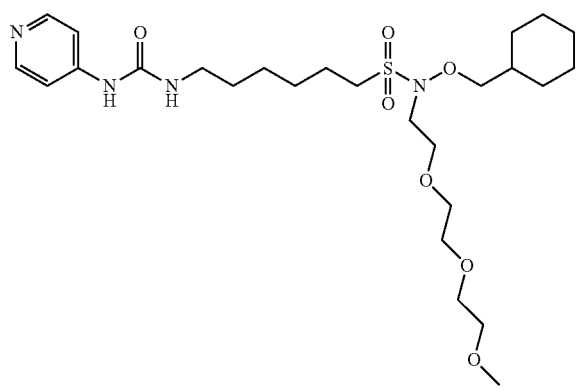 [SMILES: COCCOCCOCCN(OCC1CCCCC1)S(=O)(=O)CCCCCCNC(=O)Nc1ccncc1]

General procedure 1. Starting materials: 4-amiopyridine and 6-amino-N-(cyclohexylmethoxy)-N-(2-(2-(2-methoxyethoxy)ethoxy)ethyl)hexane-1-sulfonamide (see, e.g., WO 2009/086835).

$^1$H-NMR (CD$_3$OD): δ 8.28 (m, 2H), 7.46 (m, 2H), 3.87 (d, 2H), 3.72 (t, 2H),), 3.66 (m, 6H), 3.55 (m, 2H), 3.44 (t, 2H), 3.37 (s, 3H), 3.21 (m, 4H), 1.89 (m, 2H), 1.8-1.1 (m, 15H), 1.04 (m, 2H).

Example 30

N-(cyclohexylmethoxy)-N-(2-morpholinoethyl)-6-(3-pyridin-4-ylureido)hexane-1-sulfonamide (Compound 1030)

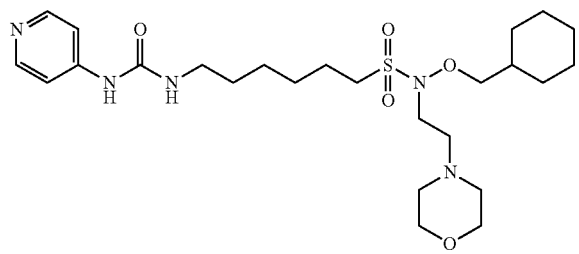 [SMILES: O=C(NCCCCCCS(=O)(=O)N(CCN1CCOCC1)OCC1CCCCC1)Nc1ccncc1]

General procedure 1. Starting materials: 4-aminopyridine and 6-amino-N-(cyclohexylmethoxy)-N-(2-morpholinoethyl)hexane-1-sulfonamide (see, e.g., WO 2009/086835).

$^1$H-NMR (CD$_3$OD): δ 8.28 (m, 2H), 7.46 (m, 2H), 3.89 (d, 2H), 3.71 (m, 4H), 3.42 (t, 2H), 3.22 (m, 4H), 2.67 (t, 2H), 2.53 (m, 4H), 1.95-1.15 (m, 17), 1.05 (m, 2H).

Example 31

N-(cyclohexylmethoxy)-N-(2-morpholinoethyl)-6-(3-(pyridin-3-ylmethyl)ureido)hexane-1-sulfonamide (Compound 1031)

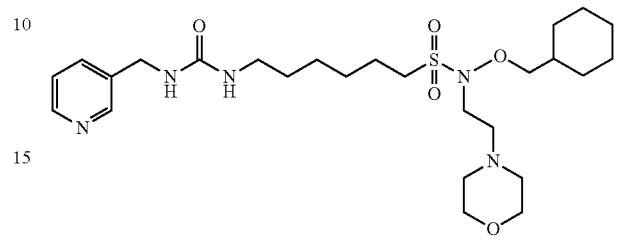

General procedure 2. Starting materials: 3-picolylamine and 6-amino-N-(cyclohexylmethoxy)-N-(2-morpholinoethyl)hexane-1-sulfonamide (see, e.g., WO 2009/086835).

$^1$H-NMR (CD$_3$OD): δ 8.49 (d, 1H), 8.43 (dd, 1H), 7.79 (dt, 1H), 7.41 (m, 1H), 4.37 (s, 2H), 3.90 (d, 2H), 3.71 (m, 4H), 3.42 (t, 2H), 3.16 (m, 4H), 2.68 (t, 2H), 2.54 (m, 4H), 1.87 (m, 2H), 1.83-1.58 (m, 6H), 1.52 (m, 4H), 1.39 (m, 2H), 1.26 (m, 3H), 1.06 (m, 2H).

Example 32

N-(cyclohexylmethoxy)-N-(2-morpholinoethyl)-6-(3-(2-(pyridin-3-yl)ethyl)ureido)hexane-1-sulfonamide (Compound 1032)

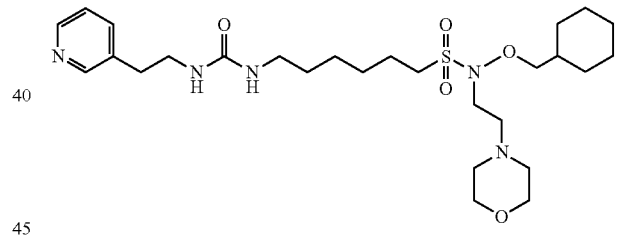

General procedure 2. Starting materials: 2-(pyridin-3-yl)ethanamine and 6-amino-N-(cyclohexylmethoxy)-N-(2-morpholinoethyl)hexane-1-sulfonamide (see, e.g., WO 2009/086835).

$^1$H-NMR (CD$_3$OD): δ 8.42 (d, 1H), 8.40 (dd, 1H), 7.75 (dt, 1H), 7.39 (m, 1H), 3.90 (d, 2H), 3.71 (m, 4H), 3.39 (m, 4H), 3.19 (m, 2H), 3.11 (t, 2H), 2.84 (t, 2H), 2.68 (t, 2H), 2.53 (m, 4H), 1.87 (m, 2H), 1.85-1.1 (m, 15H), 1.05 (m, 2H).

Example 33

N-(cyclohexylmethoxy)-6-(3-(2-(pyridin-3-yl)ethyl)ureido)hexane-1-sulfonamide (Compound 1033)

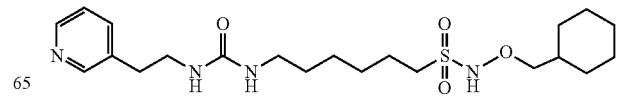

General procedure 2. Starting materials: 2-(pyridin-3-yl)ethanamine and 6-amino-N-(cyclohexylmethoxy)hexane-1-sulfonamide (see, e.g., WO 2009/086835).

$^1$H-NMR (CD$_3$OD): δ 8.41 (m, 2H), 7.75 (m, 1H), 7.39 (m, 1H), 3.75 (d, 2H), 3.39 (t, 2H), 3.18 (m, 2H), 3.10 (t, 2H), 2.84 (t, 2H), 1.85-1.1 (m, 17H), 1.0 (m, 2H).

Example 34

N-cyclohexyl-N-(2-morpholinoethoxy)-5-(3-pyridin-4-ylureido)pentane-1-sulfonamide (Compound 1034)

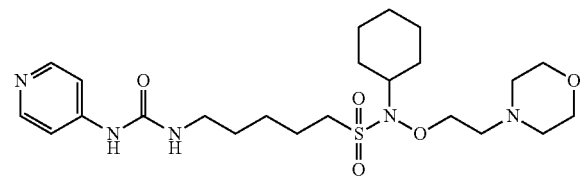 [SMILES: O=C(NCCCCCS(=O)(=O)N(OCCN1CCOCC1)C1CCCCC1)Nc1ccncc1]

General procedure 1. Starting materials: 4-aminopyridine and 5-amino-N-cyclohexyl-N-(2-morpholinoethoxy)pentane-1-sulfonamide (see, e.g., WO 2009/086835).

$^1$H-NMR (CD$_3$OD): δ 8.28 (m, 2H), 7.46 (m, 2H), 4.16 (m, 2H), 3.70 (m, 4H), 3.56 (m, 1H), 3.24 (m, 4H), 2.64 (t, 2H), 2.54 (m, 4H), 2.00-1.05 (m, 16H).

Example 35

N-cyclohexyl-N-(2-morpholinoethoxy)-7-(3-pyridin-4-ylureido)heptane-1-sulfonamide (Compound 1035)

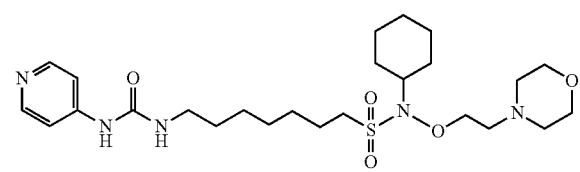 [SMILES: O=C(NCCCCCCCS(=O)(=O)N(OCCN1CCOCC1)C1CCCCC1)Nc1ccncc1]

General procedure 1. Starting materials: 4-aminopyridine and 7-amino-N-cyclohexyl-N-(2-morpholinoethoxy)heptane-1-sulfonamide (see, e.g., WO 2009/086835).

$^1$H-NMR (CD$_3$OD): δ 8.28 (m, 2H), 7.46 (m, 2H), 4.16 (m, 2H), 3.71 (m, 4H), 3.58 (m, 1H), 3.19 (m, 4H), 2.65 (t, 2H), 2.55 (m, 4H), 2.00-1.05 (m, 20H).

Example 36

N-(cyclohexylmethoxy)-6-(3-pyrimidin-4-ylureido)hexane-1-sulfonamide (Compound 1036)

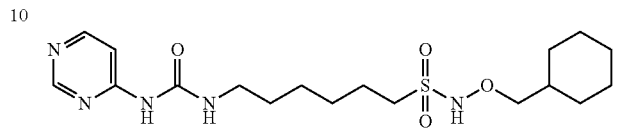

Compound 1003 (225 mg, 0.52 mmol) was dissolved in DCM, EDC (301 mg, 1.56 mmol) was added and the mixture heated with stirring at 45° C. overnight. A little water was added, the mixture was concentrated and the residue was purified by chromatography (1-5% methanol in DCM) to yield compound 1036.

$^1$H-NMR (CDCl$_3$): δ 9.55 (bs, 1H), 9.04 (t, 1H), 8.75 (m, 1H), 8.42 (d, 1H), 7.76 (s, 1H), 6.89 (m, 1H), 3.79 (d, 2H), 3.38 (m, 2H), 3.20 (m, 2H), 1.83 (m, 2H), 1.75-1.05 (m, 15H), 0.93 (m, 2H).

Example 37

1-cyclohexyl-1-(2-morphlinethoxy)-3-(5-(3-(pyridin-3-ylmethyl)ureido)pentyl)urea (Compound 1037)

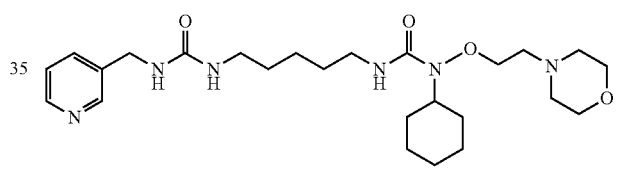

General procedure 2. Starting materials: 3-picolylamine and compound 3.

$^1$H-NMR (CD$_3$OD): δ 8.49 (d, 1H), 8.43 (dd, 1H), 7.79 (dt, 1H), 7.41 (m, 1H), 4.37 (s, 2H), 3.98 (t, 2H), 3.82 (m, 1H), 3.76 (m, 4H), 3.22 (t, 2H), 3.14 (t, 2H), 2.83 (t, 2H), 2.77 (m, 4H), 1.9-1.45 (m, 11), 1.36 (m, 4H), 1.15 (m, 1H).

Example 38

1-cyclohexyl-1-(2-morpholinethoxy)-3-(5-(3-(2-(pyridin-3-yl)ethyl)ureido)pentyl)urea (Compound 1038)

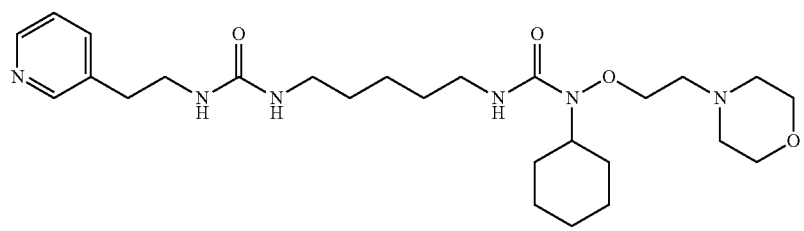 [SMILES: O=C(NCCCCCNC(=O)N(OCCN1CCOCC1)C1CCCCC1)NCCc1cccnc1]

General procedure 2. Starting materials: 2-(pyridin-3-yl)ethanamine and compound 3.

$^1$H-NMR (CD$_3$OD): δ 8.42 (d, 1H), 8.40 (dd, 1H), 7.76 (dt, 1H), 7.40 (m, 1H), 3.96 (t, 2H), 3.85 (m, 1H), 3.74 (m, 4H), 3.39 (t, 2H), 3.23 (t, 2H), 3.10 (t, 2H), 2.84 (t, 2H), 2.62 (t, 2H), 2.58 (m, 4H), 1.9-1.05 (m, 16).

Example 39

N-Cyclohexyl-N-(2-morpholinethoxy)-7-(3-pyrimidin-4-ylureido)heptanamide (Compound 1039)

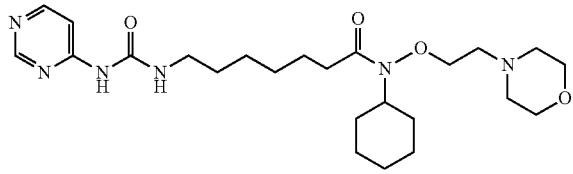 [SMILES: O=C(NCCCCCCC(=O)N(OCCN1CCOCC1)C1CCCCC1)Nc1ccncn1]

Compound 1006 (39 mg, 0.08 mmol) was dissolved in DCM, EDC (46 mg, 0.24 mmol) was added and the mixture heated with stirring at 45° C. overnight. A little water was added, the mixture was concentrated and the residue was purified by chromatography (1-5% methanol in DCM) to yield compound 1039.

$^1$H-NMR (CD$_3$OD): δ 8.73 (bs, 1H), 8.43 (d, 1H), 7.30 (m, 1H), 4.30 (m, 1H), 4.08 (m, 2H), 3.71 (m, 6H), 2.67 (t, 2H), 2.56 (m, 4H), 2.50 (t, 2H), 1.95-0.75 (m, 18H).

Example 40

N-(Cyclohexylmethoxy)-N-(2-morpholinethyl)-6-(3-(2-(pyridin-2-yl)ethyl)ureido)hexane-1-sulfonamide (Compound 1040)

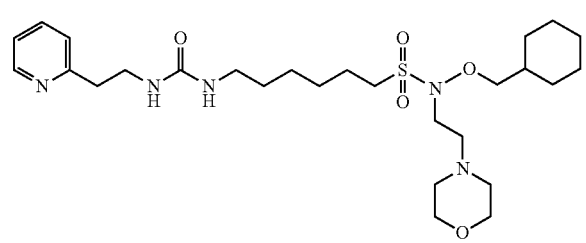 [SMILES: O=C(NCCCCCCS(=O)(=O)N(CCN1CCOCC1)OCC1CCCCC1)NCCc1ccccn1]

General procedure 2. Starting materials: 2-(pyridin-2-yl)ethanamine and 6-amino-N-(cyclohexylmethoxy)-N-(2-morpholinoethyl)hexane-1-sulfonamide (see, e.g., WO 2009/086835).

$^1$H-NMR (CD$_3$OD): δ 8.48 (dd, 1H), 7.78 (dt, 1H), 7.35 (d, 1H), 7.28 (m, 1H), 3.90 (d, 2H), 3.71 (m, 4H), 3.49 (t, 2H), 3.42 (t, 2H), 3.19 (m, 2H), 3.11 (t, 2H), 2.96 (t, 2H), 2.68 (t, 2H), 2.53 (m, 4H), 1.95-1.1 (m, 17), 1.05 (m, 2H).

Example 41

N-Cyclohexyl-N-(2-morpholinethoxy)-7-(3-(2-(pyridin-2-yl)ethyl)ureido)heptanamide (Compound 1041)

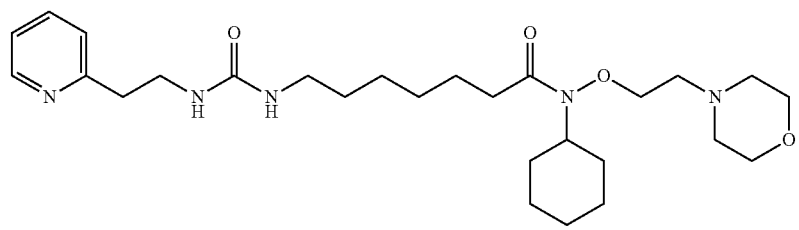 [SMILES: O=C(NCCCCCCC(=O)N(OCCN1CCOCC1)C1CCCCC1)NCCc1ccccn1]

General procedure 2. Starting materials: 2-(pyridin-2-yl)ethanamine and 7-amino-N-cyclohexyl-N-(2-morpholinoethoxy)heptanamide (see, e.g., WO 2009/086835).

$^1$H-NMR (CD$_3$OD): δ 8.48 (dd, 1H), 7.78 (dt, 1H), 7.35 (d, 1H), 7.28 (m, 1H), 4.15 (m, 1H), 4.08 (t, 2H), 3.72 (m, 4H), 3.49 (t, 2H), 3.10 (t, 2H), 2.96 (t, 2H), 2.67 (t, 2H), 2.56 (m, 4H), 2.49 (m, 2H), 1.95-1.05 (m, 18H).

Example 42

N-Cyclohexyl-N-(2-morpholinethoxy)-5-(3-(pyridin-3-yl)methyl)ureido)pentane-1-sulfonamide (Compound 1042)

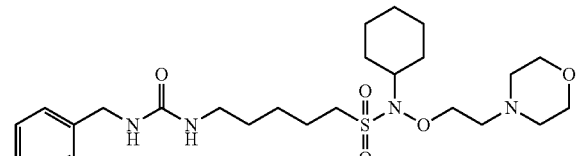

General procedure 2. Starting materials: 3-picolylamine and 5-amino-N-cyclohexyl-N-(2-morpholinoethoxy)pentane-1-sulfonamide (see, e.g., WO 2009/086835).

$^1$H-NMR (CD$_3$OD): δ 8.49 (d, 1H), 8.43 (dd, 1H), 7.80 (dt, 1H), 7.42 (m, 1H), 4.37 (s, 2H), 4.16 (t, 2H), 3.71 (m, 4H), 3.59 (m, 1H), 3.19 (m, 4H), 2.65 (t, 2H), 2.55 (m, 4H), 1.90 (m, 6H), 1.75-1.25 (m, 9), 1.19 (m, 1H).

Example 43

N-Cyclohexyl-N-(2-morpholinethoxy)-7-(3-(pyridin-3-yl)methyl)ureido)heptane-1-sulfonamide (Compound 1043)

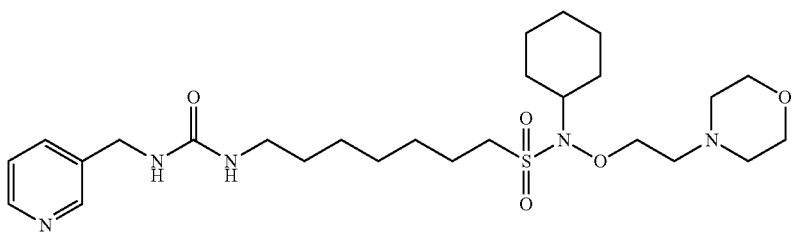 [SMILES: O=C(NCCCCCCCS(=O)(=O)N(OCCN1CCOCC1)C1CCCCC1)NCc1cccnc1]

General procedure 2. Starting materials: 3-picolylamine and 7-amino-N-cyclohexyl-N-(2-morpholinoethoxy)heptane-1-sulfonamide (see, e.g., WO 2009/086835).

$^1$H-NMR (CD$_3$OD): δ 8.49 (d, 1H), 8.43 (dd, 1H), 7.80 (dt, 1H), 7.42 (m, 1H), 4.37 (s, 2H), 4.16 (t, 2H), 3.71 (m, 4H), 3.58 (m, 1H), 3.17 (m, 4H), 2.65 (t, 2H), 2.55 (m, 4H), 2.0-1.1 (m, 20H).

Example 44

1-Isopropyl-1-(2-morpholinethoxy)-3-(5-(3-(pyridin-3-ylmethyl)ureido)pentyl)urea (Compound 1044)

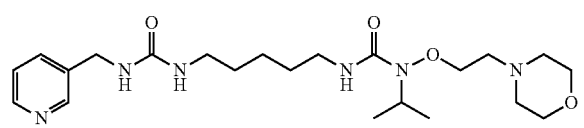 [SMILES: CC(C)N(OCCN1CCOCC1)C(=O)NCCCCCNC(=O)NCc1cccnc1]

General procedure 2. Starting materials: 3-picolylamine and compound 4.

$^1$H-NMR (CD$_3$OD): δ 8.49 (d, 1H), 8.43 (dd, 1H), 7.79 (dt, 1H), 7.41 (m, 1H), 4.37 (s, 2H), 4.22 (m, 1H), 3.99 (t, 2H), 3.72 (m, 4H), 3.22 (t, 2H), 3.13 (t, 2H), 2.63 (t, 2H), 2.58 (m, 4H), 1.52 (m, 4), 1.38 (m, 2H), 1.18 (d, 6H).

Example 45

1-Isopropyl-1-(2-morpholinethoxy)-3-(5-(3-(pyridin-3-ylethyl)ureido)pentyl)urea (Compound 1045)

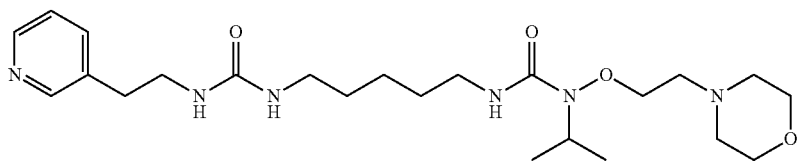 [SMILES: CC(C)N(OCCN1CCOCC1)C(=O)NCCCCCNC(=O)NCCc1cccnc1]

General procedure 2. Starting materials: 2-(pyridin-3-yl)ethanamine and compound 4.

$^1$H-NMR (CD$_3$OD): δ 8.41 (m, 2H), 7.77 (dt, 1H), 7.40 (m, 1H), 4.25 (m, 1H), 3.98 (t, 2H), 3.74 (m, 4H), 3.39 (t, 2H), 3.23 (t, 2H), 3.10 (t, 2H), 2.83 (t, 2H), 2.63 (t, 2H), 2.57 (m, 4H), 1.53 (m, 4), 1.36 (m, 2H), 1.17 (d, 6H).

Example 46

1-Isopropyl-1-(2-morpholinethoxy)-3-(5-(3-(pyridin-4-yl)ureido)pentyl)urea (Compound 1046)

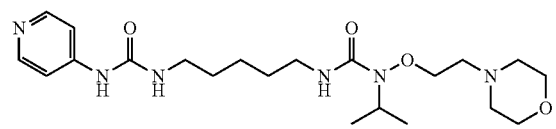 [SMILES: CC(C)N(OCCN1CCOCC1)C(=O)NCCCCCNC(=O)Nc1ccncc1]

General procedure 1. Starting materials: 4-pyridylamine and compound 4.

$^1$H-NMR (CD$_3$OD): δ 8.29 (m, 2H), 7.46 (m, 2H), 4.25 (m, 1H), 3.97 (t, 2H), 3.73 (m, 4H), 3.24 (m, 4H), 2.60 (t, 2H), 2.55 (m, 4H), 1.60 (m, 4), 1.42 (m, 2H), 1.16 (d, 6H).

Example 47

N-Isopropyl-N-(3-morpholinopropyl)-6-(3-(pyridin-3-ylmethyl)ureido)hexane-1-sulfonamide (Compound 1047)

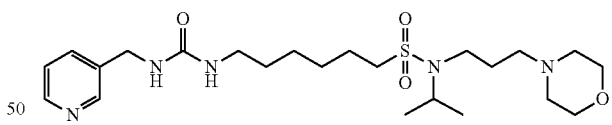

General procedure 2. Starting materials: 3-picolylamine and 6-amino-N-isopropyl-N-(3-morpholinopropyl)hexane-1-sulfonamide (see, e.g., WO 2009/086835).

¹H-NMR (CD₃OD): δ 8.49 (d, 1H), 8.43 (dd, 1H), 7.79 (dt, 1H), 7.41 (m, 1H), 4.37 (s, 2H), 4.22 (m, 1H), 3.99 (t, 2H), 3.72 (m, 4H), 3.22 (t, 2H), 3.13 (t, 2H), 2.63 (t, 2H), 2.58 (m, 4H), 1.52 (m, 4H), 1.38 (m, 2H), 1.18 (d, 6H).

Example 48

N-Isopropyl-N-(3-morpholinopropyl)-6-(3-(2-(pyridin-3-yl)ethyl)ureido)hexane-1-sulfonamide (Compound 1048)

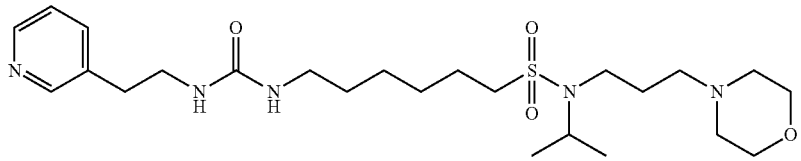 [SMILES: CC(C)N(CCCN1CCOCC1)S(=O)(=O)CCCCCCNC(=O)NCCc1cccnc1]

General procedure 2. Starting materials: 2-(pyridin-3-yl)ethanamine and 6-amino-N-isopropyl-N-(3-morpholinopropyl)hexane-1-sulfonamide (see, e.g., WO 2009/086835).

¹H-NMR (CD₃OD): δ 8.41 (m, 2H), 7.75 (dt, 1H), 7.40 (m, 1H), 3.99 (m, 1H), 3.70 (m, 4H), 3.39 (t, 2H), 3.21 (t, 2H), 3.10 (t, 2H), 3.02 (m, 2H), 2.84 (t, 2H), 2.47 (m, 4H), 2.39 (t, 2H), 1.82 (m, 4H), 1.47 (m, 4H), 1.37 (m, 2H), 1.25 (d, 6H).

Example 49

N-Isopropyl-N-(3-morpholinopropyl)-6-(3-pyridin-4-ylureido)hexane-1-sulfonamide (Compound 1049)

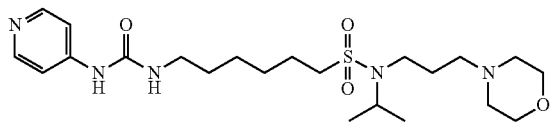 [SMILES: CC(C)N(CCCN1CCOCC1)S(=O)(=O)CCCCCCNC(=O)Nc1ccncc1]

General procedure 1. Starting materials: 4-pyridylamine and 6-amino-N-isopropyl-N-(3-morpholinopropyl)hexane-1-sulfonamide (see, e.g., WO 2009/086835).

¹H-NMR (CD₃OD): δ 8.28 (m, 2H), 7.46 (m, 2H), 3.99 (m, 1H), 3.71 (m, 4H), 3.22 (m, 4H), 3.02 (m, 2H), 2.47 (m, 4H), 2.39 (t, 2H), 1.82 (m, 4H), 1.49 (m, 6H), 1.25 (d, 6H).

Example 50

N-Cyclopentyl-N-(3-morpholinopropyl)-6-(3-(pyridin-3-ylmethyl)ureido)hexane-1-sulfonamide (Compound 1050)

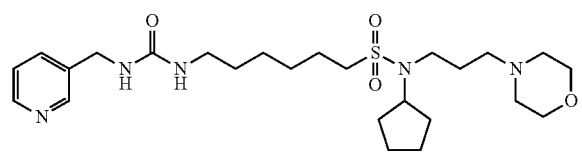 [SMILES: O=C(NCCCCCCS(=O)(=O)N(CCCN1CCOCC1)C1CCCC1)NCc1cccnc1]

General procedure 2. Starting materials: 3-picolylamine and 6-amino-N-cyclopentyl-N-(3-morpholinopropyl)hexane-1-sulfonamide (see, e.g., WO 2009/086835).

¹H-NMR (CD₃OD): δ 8.49 (d, 1H), 8.43 (dd, 1H), 7.79 (dt, 1H), 7.42 (m, 1H), 4.37 (s, 2H), 4.07 (m, 1H), 3.70 (m, 4H), 3.17 (m, 4H), 3.03 (m, 2H), 2.48 (m, 4H), 2.39 (t, 2H), 1.95-1.30 (m, 18H).

Example 51

N-(Cyclohexylmethoxy)-5-(3-(pyridin-3-ylmethyl)ureido)pentane-1-sulfonamide (Compound 1051)

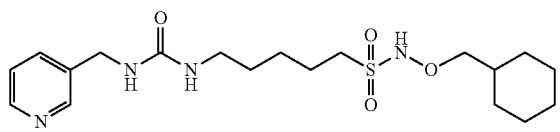 [SMILES: O=C(NCCCCCS(=O)(=O)NOCC1CCCCC1)NCc1cccnc1]

General procedure 2. Starting materials: 3-picolylamine and 5-amino-N-(cyclohexylmethoxy)pentane-1-sulfonamide (see, e.g., WO 2009/086835).

¹H-NMR (CD₃OD): δ 8.49 (d, 1H), 8.43 (dd, 1H), 7.79 (dt, 1H), 7.41 (m, 1H), 4.37 (s, 2H), 3.75 (d, 2H), 3.17 (m, 4H), 1.75 (m, 8H), 1.51 (m, 4H), 1.26 (m, 3H), 0.99 (m, 2H).

Example 52

1-(5-(morpholinosulfonyl)pentyl)-3-(3-(pyridin-3-ylmethyl)urea (Compound 1052)

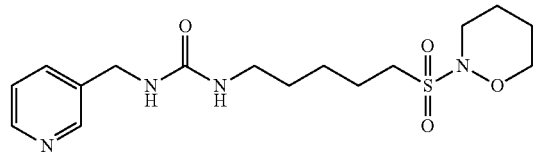 [SMILES: O=C(NCCCCCS(=O)(=O)N1CCCCO1)NCc1cccnc1]

General procedure 2. Starting materials: 3-picolylamine and 5-(morpholinosulfonyl)pentane-1-amine (see, e.g., WO 2009/086835).

¹H-NMR (CD₃OD): δ 8.49 (d, 1H), 8.43 (dd, 1H), 7.79 (dt, 1H), 7.41 (m, 1H), 4.37 (s, 2H), 4.10 (t, 2H), 3.36 (t, 2H), 3.19 (m, 4H), 1.87 (m, 4H), 1.71 (m, 2H), 1.51 (m, 4H).

Example 53

N-(Cyclohexylmethoxy)-7-(3-(pyridin-3-ylmethyl)ureido)heptane-1-sulfonamide (Compound 1053)

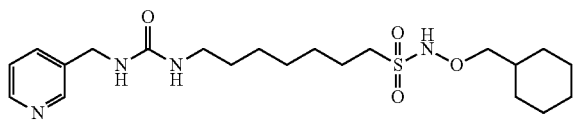 [SMILES: O=C(NCCCCCCCS(=O)(=O)NOCC1CCCCC1)NCc1cccnc1]

General procedure 2. Starting materials: 3-picolylamine and 7-amino-N-(cyclohexylmethoxy)heptane-1-sulfonamide (see, e.g., WO 2009/086835).

$^1$H-NMR (CD$_3$OD): δ 8.49 (d, 1H), 8.43 (dd, 1H), 7.79 (dt, 1H), 7.41 (m, 1H), 4.37 (s, 2H), 3.75 (d, 2H), 3.16 (m, 4H), 1.76 (m, 8H), 1.6-1.1 (m, 11H), 0.99 (m, 2H).

Example 54

1-(7-(morpholinosulfonyl)heptyl)-3-(3-(pyridin-3-ylmethyl)urea (Compound 1054)

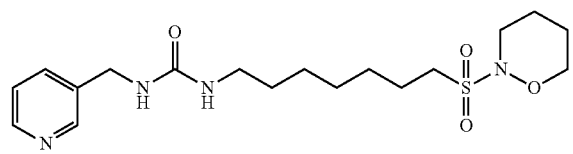 [SMILES: O=C(NCCCCCCCS(=O)(=O)N1CCCCO1)NCc1cccnc1]

General procedure 2. Starting materials: 3-picolylamine and 7-(morpholinosulfonyl)heptane-1-amine (see, e.g., WO 2009/086835).

$^1$H-NMR (CD$_3$OD): δ 8.49 (d, 1H), 8.43 (dd, 1H), 7.79 (dt, 1H), 7.41 (m, 1H), 4.37 (s, 2H), 4.11 (t, 2H), 3.36 (t, 2H), 3.17 (m, 4H), 1.86 (m, 4H), 1.71 (m, 2H), 1.49 (m, 4H), 1.37 (m, 4H).

Example 55

N-Cyclohexyl-N-(2-morpholinoethoxy)-7-(3-(pyridin-2-ylmethyl)ureido)heptanamide (Compound 1055)

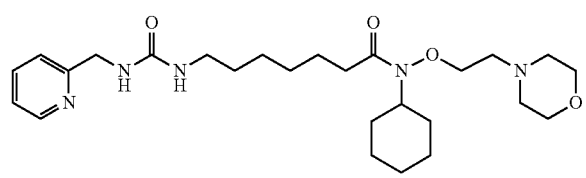 [SMILES: O=C(NCCCCCCC(=O)N(OCCN1CCOCC1)C1CCCCC1)NCc1ccccn1]

General procedure 2. Starting materials: 2-picolylamine and 7-amino-N-cyclohexyl-N-(2-morpholinoethoxy)heptanamide (see, e.g., WO 2009/086835).

$^1$H-NMR (CD$_3$OD): δ 8.48 (d, 1H), 7.82 (t, 1H), 7.42 (d, 1H), 7.30 (m, 1H), 4.44 (s, 2H), 4.17 (m, 1H), 4.10 (t, 2H), 3.73 (m, 4H), 3.16 (t, 2H), 2.8-2.4 (m, 8H), 1.9-1.25 (m, 17H), 1.21 (m, 1H).

Example 56

N-Cyclopentyl-N-(2-morpholinoethoxy)-6-(3-(pyridin-3-ylmethyl)ureido)hexane-1-sulfonamide (Compound 1056)

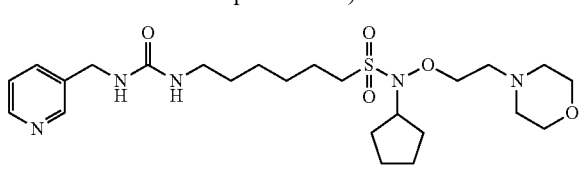

General procedure 2. Starting materials: 3-picolylamine and 6-amino-N-cyclopentyl-N-(2-morpholinoethoxy)hexane-1-sulfonamide (see, e.g., WO 2009/086835).

$^1$H-NMR (CD$_3$OD): δ 8.49 (d, 1H), 8.43 (dd, 1H), 7.79 (dt, 1H), 7.41 (m, 1H), 4.37 (s, 2H), 4.20 (bs, 2H), 4.04 (m, 1H), 3.70 (t, 4H), 3.21 (bs, 2H), 3.16 (t, 2H), 2.65 (t, 2H), 2.54 (t, 4H), 2.0-1.3 (m, 16H).

Example 57

N-Cycloheptyl-N-(3-morpholinopropyl)-6-(3-(pyridin-3-ylmethyl)ureido)hexane-1-sulfonamide (Compound 1057)

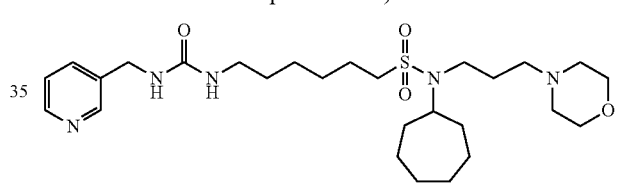

General procedure 2. Starting materials: 3-picolylamine and 6-amino-N-cycloheptyl-N-(3-morpholinopropyl)hexane-1-sulfonamide (see, e.g., WO 2009/086835).

$^1$H-NMR (CD$_3$OD): δ 8.49 (d, 1H), 8.43 (dd, 1H), 7.79 (dt, 1H), 7.42 (m, 1H), 4.37 (s, 2H), 3.71 (m, 4H), 3.65 (m, 1H), 3.23 (m, 2H), 3.15 (t, 2H), 3.01 (m, 2H), 2.47 (m, 4H), 2.38 (t, 4H), 2.0-1.3 (m, 22H).

Example 58

N-Cycloheptyl-N-(2-morpholinoethoxy)-6-(3-(pyridin-3-ylmethyl)ureido)hexane-1-sulfonamide (Compound 1058)

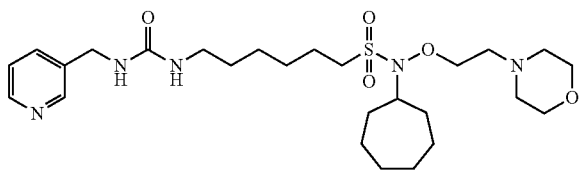 [SMILES: O=C(NCCCCCCS(=O)(=O)N(OCCN1CCOCC1)C1CCCCCC1)NCc1cccnc1]

General procedure 2. Starting materials: 3-picolylamine and 6-amino-N-cycloheptyl-N-(2-morpholinoethoxy)hexane-1-sulfonamide (see, e.g., WO 2009/086835).

MS [M+H]$^+$=540.3, [M−H+HCOOH]$^-$=584.5.

Example 59

N-Cyclobutyl-N-(2-morpholinoethoxy)-6-(3-(pyridin-3-ylmethyl)ureido)hexane-1-sulfonamide (Compound 1059)

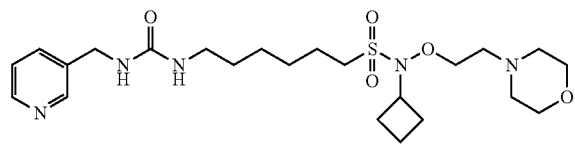 [SMILES: O=C(NCCCCCCS(=O)(=O)N(OCCN1CCOCC1)C1CCC1)NCc1cccnc1]

General procedure 2. Starting materials: 3-picolylamine and 6-amino-N-cyclobutyl-N-(2-morpholinoethoxy)hexane-1-sulfonamide (see, e.g., WO 2009/086835).

$^1$H-NMR (CD$_3$OD): 8.49 (d, 1H), 8.43 (dd, 1H), 7.79 (dt, 1H), 7.42 (m, 1H), 4.37 (s, 2H), 4.24 (m, 1H), 4.20 (m, 2H), 3.71 (t, 4H), 3.15 (t, 2H), 3.07 (t, 2H), 2.70 (t, 2H), 2.57 (t, 4H), 2.41 (m, 2H), 2.15 (m, 2H), 1.84 (m, 2H), 1.74 (m, 2H), 1.50 (m, 4H), 1.39 (m, 2H).

Example 60

N-Cyclobutyl-N-(3-morpholinopropyl)-6-(3-(pyridin-3-ylmethyl)ureido)hexane-1-sulfonamide (Compound 1060)

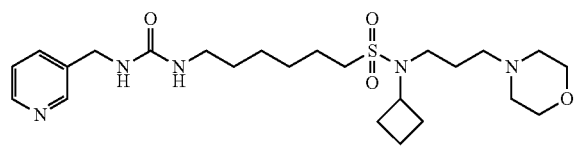 [SMILES: O=C(NCCCCCCS(=O)(=O)N(CCCN1CCOCC1)C1CCC1)NCc1cccnc1]

General procedure 2. Starting materials: 3-picolylamine and 6-amino-N-cyclobutyl-N-(3-morpholinopropyl)hexane-1-sulfonamide (see, e.g., WO 2009/086835).

$^1$H-NMR (CD$_3$OD): δ 8.49 (d, 1H), 8.43 (dd, 1H), 7.79 (dt, 1H), 7.42 (m, 1H), 4.37 (s, 2H), 4.21 (m, 1H), 3.71 (m, 4H), 3.29 (m, 2H), 3.15 (t, 2H), 2.97 (m, 2H), 2.48 (m, 4H), 2.41 (t, 2H), 2.21 (m, 4H), 1.74 (m, 6H), 1.43 (m, 6H).

Example 61

N-Cyclohexyl-N-(3-(dimethylamino)propyl)-6-(3-(pyridin-3-ylmethyl)ureido)hexane-1-sulfonamide (Compound 1061)

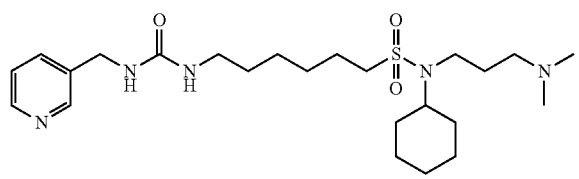 [SMILES: CN(C)CCCN(C1CCCCC1)S(=O)(=O)CCCCCCNC(=O)NCc1cccnc1]

General procedure 2. Starting materials: 3-picolylamine and 6-amino-N-cyclohexyl-N-(3-dimethylamino)propyl)hexane-1-sulfonamide (see, e.g., WO 2009/086835).

$^1$H-NMR (CD$_3$OD): δ 8.49 (d, 1H), 8.43 (dd, 1H), 7.79 (dt, 1H), 7.42 (m, 1H), 4.37 (s, 2H), 3.51 (m, 1H), 3.17 (m, 4H), 3.02 (m, 2H), 2.35 (t, 2H), 2.26 (s, 6H), 1.9-1.25 (m, 19H), 1.18 (m, 1H).

Example 62

N-Cyclohexyl-N-(2-morpholinoethoxy)-7-(3-pyridin-3-ylthioureido)heptanamide (Compound 1062)

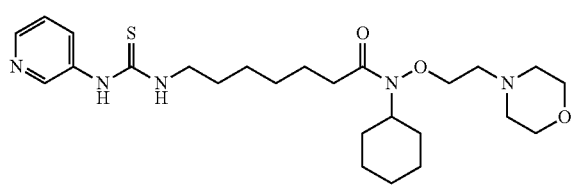

General procedure 3. Starting materials: 3-pyridylamine and 7-amino-N-cyclohexyl-N-(2-morpholinoethoxy)heptanamide (see, e.g., WO 2009/086835).

$^1$H-NMR (CD$_3$OD): δ 8.59 (d, 1H), 8.30 (d, 1H), 8.04 (bd, 1H), 7.42 (m, 1H), 4.15 (m, 1H), 4.10 (t, 2H), 3.73 (m, 4H), 3.60 (m, 2H), 2.8-2.4 (m, 8H), 1.9-1.25 (m, 17H), 1.20 (m, 1H).

Example 63

N-Cyclohexyl-N-(2-morpholinoethyl)-6-(3-(pyridin-3-ylmethyl)ureido)hexane-1-sulfonamide (Compound 1063)

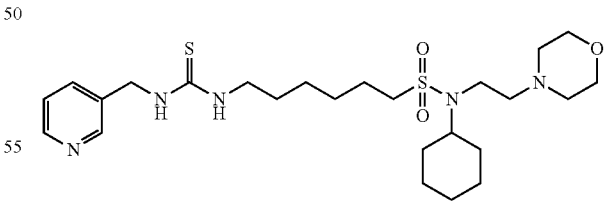

General procedure 2. Starting materials: 3-picolylamine and 6-amino-N-cyclohexyl-N-(2-morpholinoethyl)hexane-1-sulfonamide (see, e.g., WO 2009/086835).

$^1$H-NMR (CD$_3$OD): δ 8.49 (d, 1H), 8.43 (dd, 1H), 7.79 (dt, 1H), 7.42 (m, 1H), 4.37 (s, 2H), 3.70 (m, 4H), 3.51 (m, 1H), 3.34 (t, 2H), 3.14 (m, 4H), 2.54 (m, 6H), 1.9-1.25 (m, 17H), 1.18 (m, 1H).

Example 64

N-Cyclopentyl-N-(3-morpholinopropyl)-6-(3-pyridin-4-ylthioureido)hexane-1-sulfonamide (Compound 1064)

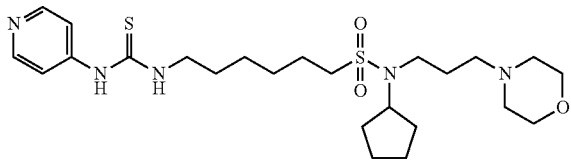 [SMILES: O=S(=O)(CCCCCCNC(=S)Nc1ccncc1)N(CCCN1CCOCC1)C1CCCC1]

General procedure 3. Starting materials: 4-pyridylamine and 6-amino-N-cyclopentyl-N-(3-morpholinopropyl)hexane-1-sulfonamide (see, e.g., WO 2009/086835).

$^1$H-NMR (CD$_3$OD): δ 8.35 (m, 2H), 7.74 (m, 2H), 4.07 (m, 1H), 3.70 (m, 4H), 3.62 (t, 2H), 3.18 (m, 2H), 3.05 (m, 2H), 2.47 (m, 4H), 2.38 (t, 2H), 1.95-1.35 (m, 18H).

Example 65

N-Cyclohexyl-N-(2-morpholinoethoxy)-7-(3-pyridin-3-ylureido)heptanamide (Compound 1065)

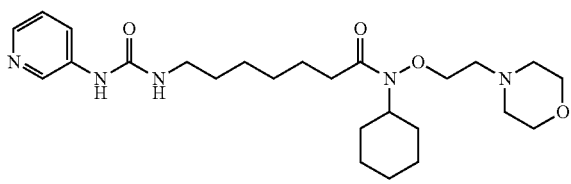 [SMILES: O=C(NCCCCCCC(=O)N(OCCN1CCOCC1)C1CCCCC1)Nc1cccnc1]

General procedure 1. Starting materials: 3-pyridylamine and 7-amino-N-cyclohexyl-N-(2-morpholinoethoxy)heptanamide (see, e.g., WO 2009/086835).

$^1$H-NMR (CD$_3$OD): δ 8.55 (d, 1H), 8.14 (dd, 1H), 7.96 (dt, 1H), 7.35 (m, 1H), 4.15 (m, 1H), 4.09 (t, 2H), 3.72 (t, 4H), 3.23 (t, 2H), 2.67 (t, 2H), 2.56 (t, 4H), 2.51 (t, 2H), 1.9-1.1 (m, 18H).

Example 66

N-Cyclopentyl-N-(3-morpholinopropyl)-6-(3-pyridin-4-ylureido)hexane-1-sulfonamide (Compound 1066)

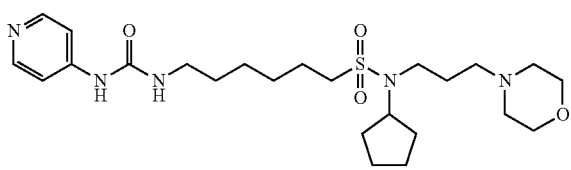

General procedure 1. Starting materials: 4-pyridylamine and 6-amino-N-cyclopentyl-N-(3-morpholinopropyl)hexane-1-sulfonamide (see, e.g., WO 2009/086835).

$^1$H-NMR (CD$_3$OD): δ 8.28 (m, 2H), 7.46 (m, 2H), 4.07 (m, 1H), 3.70 (m, 4H), 3.23 (t, 2H), 3.18 (m, 2H), 3.04 (m, 2H), 2.47 (m, 4H), 2.38 (t, 2H), 1.95-1.15 (m, 18H).

Example 67

Ethyl N-cyclohexyl-P-(6-(3-pyridin-3-ylmethyl)ureido)phosphonamidate (Compound 1067)

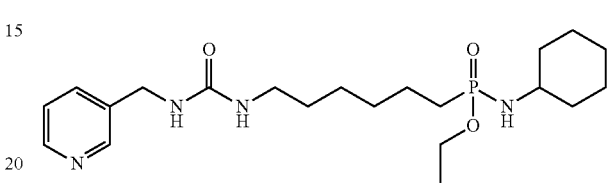

General procedure 2. Starting materials: 3-picolylamine and ethyl P-aminohexyl-N-cyclohexylphosphonamidate (see, e.g., WO 2009/086835).

$^1$H-NMR (CD$_3$OD): δ 8.49 (d, 1H), 8.43 (dd, 1H), 7.79 (dt, 1H), 7.41 (m, 1H), 4.37 (s, 2H), 3.99 (m, 2H), 3.14 (t, 2H), 2.97 (m, 1H), 1.89 (m, 2H), 1.8-1.05 (m, 21H).

Example 68

1-(6-(3,4-dihydroisoquinolin-2(1H)-ylsulfonyl)hexyl)-3-(pyridin-3-ylmethyl)urea (Compound 1068)

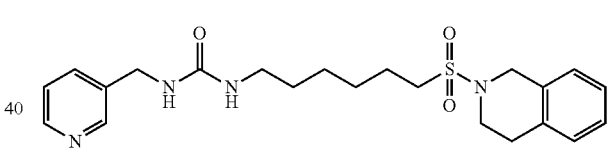

General procedure 2. Starting materials: 3-picolylamine and 6-(3,4-dihydroisoquinolin-2(1H)-ylsulfonyl)hexan-1-amine (see, e.g., WO 2009/086835).

$^1$H-NMR (DMSO-d$_6$): δ 8.45 (d, 1H), 8.42 (dd, 1H), 7.63 (dt, 1H), 7.33 (m, 1H), 7.17 (m, 4H), 6.37 (t, 1H), 5.98 (t, 1H), 4.39 (s, 2H), 4.19 (d, 2H), 3.47 (t, 2H), 3.09 (m, 2H), 2.97 (m, 2H), 2.87 (t, 2H), 1.64 (m, 2H), 1.34 (m, 4H), 1.25 (m, 2H).

Example 69

N-cyclopentyl-N-(3-morpholinopropyl)-5-(3-(pyridin-3-ylmethyl)ureido)pentane-1-sulfonamide (Compound 1069)

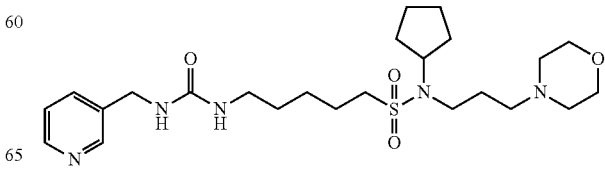

General procedure 2. Starting materials: 3-picolylamine and 5-amino-N-cyclopentyl-N-(3-morpholinopropyl)pentane-1-sulfonamide (see, e.g., WO 2009/086835).

$^1$H-NMR (CD$_3$OD): δ 8.49 (d, 1H), 8.43 (dd, 1H), 7.79 (dt, 1H), 7.41 (m, 1H), 4.37 (s, 2H), 4.07 (m, 1H), 3.70 (m, 4H), 3.17 (m, 4H), 3.03 (m, 2H), 2.47 (m, 4H), 2.38 (t, 2H), 1.95-1.40 (m, 16H).

Example 70

N-cyclobutyl-N-(3-morpholinopropyl)-5-(3-(pyridin-3-ylmethyl)ureido)pentane-1-sulfonamide (Compound 1070)

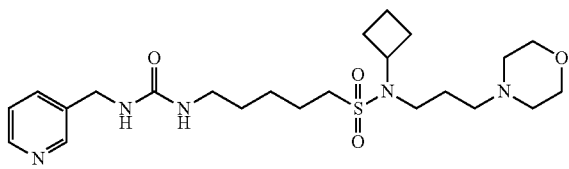 [SMILES: O=C(NCCCCCS(=O)(=O)N(CCCN1CCOCC1)C1CCC1)NCc1cccnc1]

General procedure 2. Starting materials: 3-picolylamine and 5-amino-N-cyclobutyl-N-(3-morpholinopropyl)pentane-1-sulfonamide (see, e.g., WO 2009/086835).

$^1$H-NMR (CD$_3$OD): δ 8.49 (d, 1H), 8.43 (dd, 1H), 7.79 (dt, 1H), 7.41 (m, 1H), 4.37 (s, 2H), 4.21 (m, 1H), 3.71 (t, 4H), 3.29 (m, 2H), 3.15 (t, 2H), 2.97 (m, 2H), 2.48 (t, 4H), 2.41 (t, 2H), 2.20 (m, 4H), 1.9-1.35 (m, 10H).

Example 71

N-cyclobutyl-N-(2-morpholinoethoxy)-5-(3-(pyridin-3-ylmethyl)ureido)pentane-1-sulfonamide (Compound 1071)

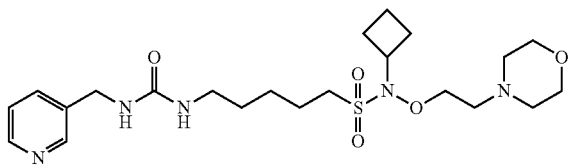 [SMILES: O=C(NCCCCCS(=O)(=O)N(OCCN1CCOCC1)C1CCC1)NCc1cccnc1]

General procedure 2. Starting materials: 3-picolylamine and 5-amino-N-cyclobutyl-N-(2-morpholinoetoxy)pentane-1-sulfonamide (see, e.g., WO 2009/086835).

$^1$H-NMR (CD$_3$OD): δ 8.49 (d, 1H), 8.43 (dd, 1H), 7.79 (dt, 1H), 7.42 (m, 1H), 4.37 (s, 2H), 4.25 (m, 1H), 4.20 (m, 2H), 3.72 (t, 4H), 3.16 (t, 2H), 3.07 (t, 2H), 2.70 (t, 2H), 2.57 (t, 4H), 2.41 (m, 2H), 2.15 (m, 2H), 1.87 (m, 2H), 1.75 (m, 2H), 1.52 (m, 4H).

Example 72

Ethyl morpholino(6-(3-pyridin-3-ylmethyl)ureido)hexyl)phosphinate (Compound 1072)

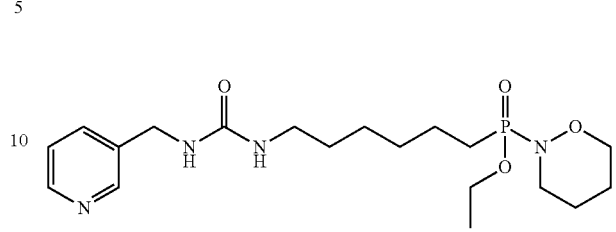

General procedure 2. Starting materials: 3-picolylamine and ethyl 6-aminohexyl(morpholino)phosphinate (see, e.g., WO 2009/086835).

$^1$H-NMR (CD$_3$OD): δ 8.49 (d, 1H), 8.43 (dd, 1H), 7.79 (dt, 1H), 7.41 (m, 1H), 4.37 (s, 2H), 4.10 (m, 2H), 3.97 (t, 2H), 3.37 (m, 2H), 3.15 (t, 2H), 1.95-1.25 (m, 17H).

Example 73

1-(6-(4-acetylpiperazin-1-ylsulfonyl)hexyl)-3-(pyridin-3-ylmethyl)urea (Compound 1073)

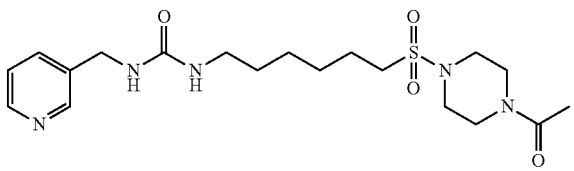 [SMILES: CC(=O)N1CCN(S(=O)(=O)CCCCCCNC(=O)NCc2cccnc2)CC1]

General procedure 2. Starting materials: 3-picolylamine and 1-(4-(6-aminohexylsulfonyl)piperazin-1-yl)ethanone (see, e.g., WO 2009/086835).

$^1$H-NMR (CD$_3$OD): δ 8.49 (d, 1H), 8.43 (dd, 1H), 7.79 (dt, 1H), 7.41 (m, 1H), 4.37 (s, 2H), 3.64 (m, 4H), 3.32 (m, 2H), 3.26 (t, 2H), 3.15 (t, 2H), 3.04 (m, 2H), 2.14 (s, 3H), 1.79 (m, 2H), 1.89 (m, 4H), 1.39 (m, 2H)

Example 74

N-Cyclopentyl-N-(2-morpholinoethoxy)-5-(3-(pyridin-3-ylmethyl)ureido)pentane-1-sulfonamide (Compound 1074)

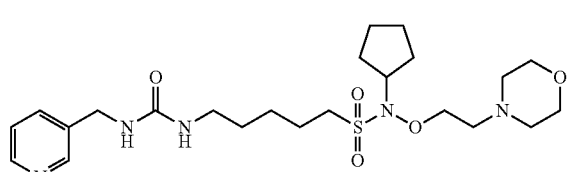

General procedure 2. Starting materials: 3-picolylamine and 5-amino-N-cyclopentyl-N-(2-morpholinoetoxy)pentane-1-sulfonamide (see, e.g., WO 2009/086835).

$^1$H-NMR (CD$_3$OD): δ 8.49 (d, 1H), 8.43 (dd, 1H), 7.80 (dt, 1H), 7.42 (m, 1H), 4.37 (s, 2H), 4.20 (bs, 2H), 4.04 (m, 1H), 3.70 (t, 4H), 3.17 (m, 4H), 2.65 (t, 2H), 2.54 (t, 4H), 2.0-1.45 (m, 14H).

Example 75

N-Cyclohexyl-N-(2-morpholinoethoxy)-6-(3-(pyridin-3-ylmethyl)ureido)hexane-1-sulfonamide oxalate (Compound 1075)

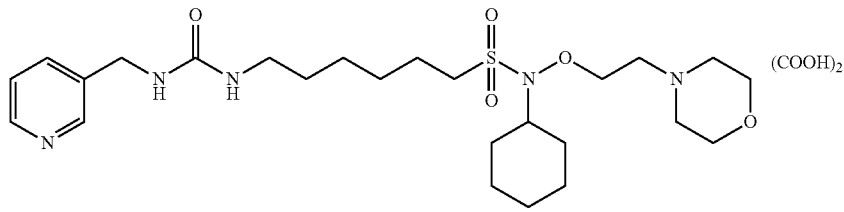

(COOH)$_2$

General procedure 2. Starting materials: 3-picolylamine and 6-amino-N-cyclohexyl-N-(2-morpholinoetoxy)hexane-1-sulfonamide (see, e.g., WO 2009/086835).

$^1$H-NMR (400 MHz, DMSO-d$_6$): δ 8.46 (d, 1H), 8.43 (dd, 1H), 7.63 (dt, 1H), 7.33 (m, 1H), 6.36 (t, 1H), 5.99 (t, 1H), 4.21 (d, 2H), 4.09 (t, 2H), 3.69-3.61 (m, 4H), 3.50 (m, 1H), 3.22 (t, 2H), 2.99 (m, 2H), 2.88-2.78 (m, 2H), 2.76-2.64 (m, 4H), 1.92-1.81 (m, 2H), 1.80-1.65 (m, 4H), 1.63-1.32 (m, 7H), 1.32-1.19 (m, 4H), 1.16-1.00 (m, 1H).

Example 76

N-Phenyl-6-(3-(pyridin-3-ylmethyl)ureido)hexane-1-sulfonamide (Compound 1076)

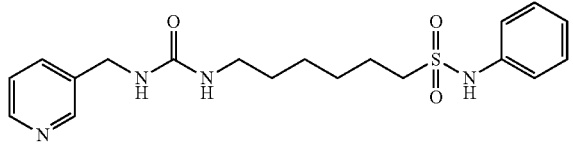 [SMILES: O=C(NCCCCCCS(=O)(=O)Nc1ccccc1)NCc1cccnc1]

General procedure 2. Starting materials: 3-picolylamine and 6-amino-N-phenylhexane-1-sulfonamide (see, e.g., WO 2009/086835).

$^1$H-NMR (CD$_3$OD): δ 8.48 (d, 1H), 8.42 (dd, 1H), 7.78 (dt, 1H), 7.41 (m, 1H), 7.33 (m, 2H), 7.25 (m, 2H), 7.12 (m, 1H), 4.36 (s, 2H), 3.08 (m, 4H), 1.77 (m, 2H), 1.5-1.2 (m, 6H).

Example 77

N-(Benzyloxy)-N-methyl-6-(3-(pyridin-3-ylmethyl)ureido)hexane-1-sulfonamide (Compound 1077)

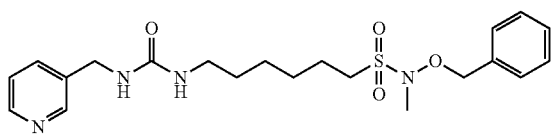 [SMILES: CN(OCc1ccccc1)S(=O)(=O)CCCCCCNC(=O)NCc1cccnc1]

General procedure 2. Starting materials: 3-picolylamine and 6-amino-N-(benzyloxy)-N-methylhexane-1-sulfonamide (see, e.g., WO 2009/086835).

$^1$H-NMR (CD$_3$OD): δ 8.49 (d, 1H), 8.42 (dd, 1H), 7.79 (dt, 1H), 7.40 (m, 6H), 4.94 (s, 2H), 4.36 (s, 2H), 3.15 (m, 4H), 2.92 (s, 3H), 1.86 (m, 2H), 1.49 (m, 4H), 1.37 (m, 2H).

Example 78

N-(Benzyloxy)-N-(2-morpholinoethyl)-6-(3-(pyridin-3-ylmethyl)ureido)hexane-1-sulfonamide (Compound 1078)

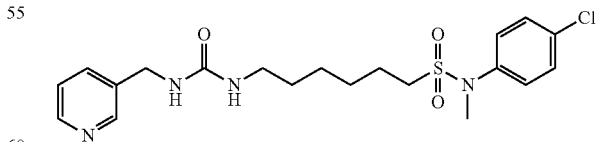

General procedure 2. Starting materials: 3-picolylamine and 6-amino-N-(benzyloxy)-N-(2-morpholinoethyl)hexane-1-sulfonamide (see, e.g., WO 2009/086835).

$^1$H-NMR (CD$_3$OD): δ 8.49 (d, 1H), 8.42 (dd, 1H), 7.79 (dt, 1H), 7.40 (m, 6H), 5.06 (s, 2H), 4.36 (s, 2H), 3.68 (m, 4H), 3.40 (t, 2H), 3.22 (t, 2H), 3.14 (t, 2H), 2.53 (t, 2H), 2.46 (t, 4H), 1.88 (m, 2H), 1.51 (m, 4H), 1.39 (m, 2H).

Example 79

N-(4-Chlorophenyl)-N-methyl-6-(3-(pyridin-3-ylmethyl)ureido)hexane-1-sulfonamide (Compound 1079)

General procedure 2. Starting materials: 3-picolylamine and 6-amino-N-(4-chlorophenyl)-N-methylhexane-1-sulfonamide (see, e.g., WO 2009/086835).

$^1$H-NMR (CD$_3$OD): δ 8.49 (d, 1H), 8.42 (dd, 1H), 7.78 (dt, 1H), 7.42 (m, 5H), 4.36 (s, 2H), 3.32 (s, 3H), 3.11 (m, 4H), 1.76 (m, 2H), 1.46 (m, 4H), 1.35 (m, 2H).

Example 80

N-(4-Chlorophenyl)-N-(2-morpholinoethyl)-6-(3-(pyridin-3-ylmethyl)ureido)hexane-1-sulfonamide (Compound 1080)

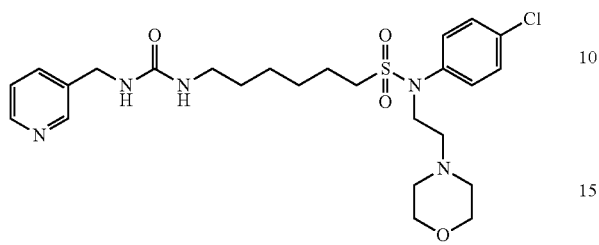

$^1$H-NMR (CD$_3$OD): δ 8.49 (d, 1H), 8.42 (dd, 1H), 7.78 (dt, 1H), 7.42 (m, 5H), 4.36 (s, 2H), 3.32 (s, 3H), 3.11 (m, 4H), 1.76 (m, 2H), 1.46 (m, 4H), 1.35 (m, 2H).

General procedure 2. Starting materials: 3-picolylamine and 6-amino-N-(4-chlorophenyl)-N-(2-morpholinoethyl)hexane-1-sulfonamide (see, e.g., WO 2009/086835).

$^1$H-NMR (CD$_3$OD): δ 8.49 (d, 1H), 8.42 (dd, 1H), 7.77 (m, 1H), 7.44 (m, 5H), 4.36 (s, 2H), 3.85 (m, 2H), 3.63 (m, 4H), 3.14 (m, 4H), 2.44 (m, 6H), 1.79 (m, 2H), 1.47 (m, 4H), 1.36 (m, 2H).

Example 81

N-Cyclohexyl-N-(3-morpholinopropyl)-6-(3-(pyridin-4-ylthioureido)hexane-1-sulfonamide oxalate (Compound 1081)

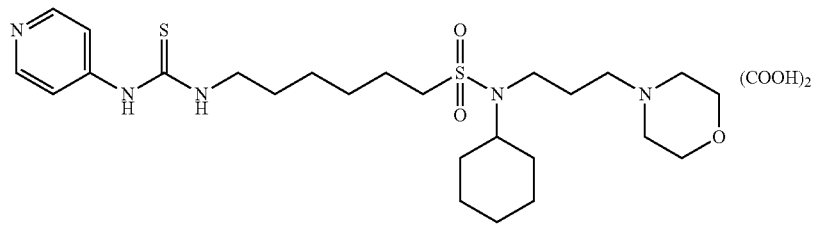

General procedure 3. Starting materials: 4-pyridylamine and 6-amino-N-cyclohexyl-N-(3-morpholinopropyl)hexane-1-sulfonamide (see, e.g., WO 2009/086835).

$^1$H-NMR (400 MHz, DMSO-d$_6$): δ 10.16 (bs, 1H), 8.53 (bs, 1H), 8.38 (d, 2H), 7.67 (d, 2H), 3.70 (bs, 4H), 3.51-3.36 (m, 3H), 3.13 (t, 2H), 3.02 (t, 2H), 2.85 (bs, 4H), 2.73 (t, 2H), 1.86-1.20 (m, 19H), 1.15-1.00 (m, 1H).

Example 82

N-Cyclopentyl-N-(2-morpholinoethoxy)-6-(3-(pyridin-4-ylthioureido)hexane-1-sulfonamide (Compound 1082)

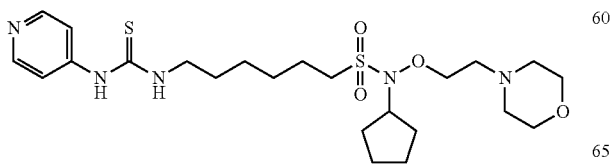

General procedure 3. Starting materials: 4-pyridylamine and 6-amino-N-cyclopentyl-N-(2-morpholinoethoxy)hexane-1-sulfonamide (see, e.g., WO 2009/086835).

$^1$H-NMR (400 MHz, DMSO-d$_6$): δ 10.29 (bs, 1H), 8.63 (bs, 1H), 8.41 (d, 2H), 7.75-7.70 (m, 2H), 4.12 (t, 2H), 3.94 (m, 1H), 3.66-3.60 (m, 4H), 3.48 (m, 2H), 3.19 (t, 2H), 2.78 (t, 2H), 2.65 (bs, 4H), 1.91-1.80 (m, 2H), 1.80-1.68 (m, 4H), 1.68-1.61 (m, 2H), 1.57 (m, 2H), 1.52-1.40 (m, 4H), 1.40-1.29 (m, 2H).

Example 83

N-Cyclopentyl-N-(2-morpholinoethoxy)-5-(3-(pyridin-4-ylthioureido)pentane-1-sulfonamide oxalate (Compound 1083)

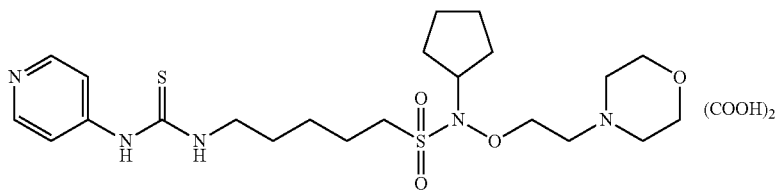

General procedure 3. Starting materials: 4-pyridylamine and 5-amino-N-cyclopentyl-N-(2-morpholinoethoxy)pentane-1-sulfonamide (see, e.g., WO 2009/086835).

$^1$H-NMR (400 MHz, DMSO-d$_6$): δ 10.52 (bs, 1H), 8.81 (bs, 1H), 8.44-8.38 (m, 2H), 7.76 (d, 2H), 4.13 (t, 2H), 3.94 (m, 1H), 3.66-3.60 (m, 4H), 3.49 (m, 2H), 3.21 (t, 2H), 2.80 (t, 2H), 2.71-2.62 (m, 4H), 1.92-1.69 (m, 6H), 1.69-1.55 (m, 4H), 1.55-1.40 (m, 4H).

Example 84

N-Cyclopentyl-N-(2-morpholinoethoxy)-5-(3-(pyridin-4-ylureido)pentane-1-sulfonamide (Compound 1084)

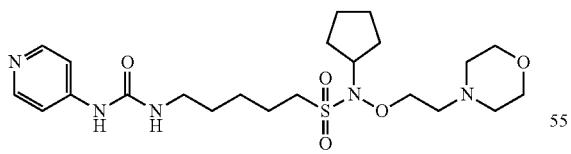

General procedure 1. Starting materials: 4-pyridylamine and 5-amino-N-cyclopentyl-N-(2-morpholinoethoxy)pentane-1-sulfonamide (see, e.g., WO 2009/086835).

$^1$H-NMR (400 MHz, CDCl$_3$): δ 8.37 (d, 2H), 7.46 (s, 1H), 7.34 (d, 2H), 5.33 (t, 1H), 4.19 (bs, 2H), 4.01 (m, 1H), 3.71 (t, 4H), 3.28 (m, 2H), 3.09 (bs, 2H), 2.63 (t, 2H), 2.52 (t, 4H), 1.99-1.63 (m, 8H), 1.63-1.46 (m, 6H).

Example 85

Ethyl morpholino(6-(3-(pyridin-4-ylthioureido) hexyl)phosphinate oxalate (Compound 1085)

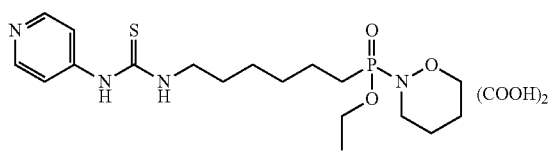

General procedure 3. Starting materials: 4-pyridylamine and ethyl 6-aminohexyl(morpholino)phosphinate (see, e.g., WO 2009/086835).

$^1$H-NMR (400 MHz, DMSO-d$_6$): δ 10.32 (bs, 1H), 8.65 (bs, 1H), 8.41 (d, 2H), 7.77-7.72 (m, 2H), 3.81-4.05 (m, 4H), 3.47 (m, 2H), 3.29-3.19 (m, 2H), 1.82-1.43 (m, 10H), 1.43-1.27 (m, 4H), 1.22 (t, 3H).

Example 86

Ethyl morpholino(6-(3-(pyridin-4-ylureido)hexyl) phosphinate (Compound 1086)

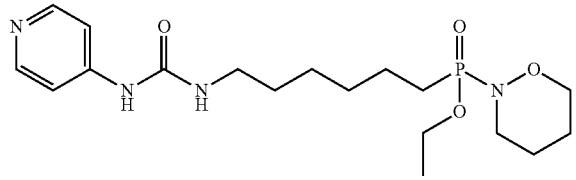 [SMILES: CCOP(=O)(CCCCCCNC(=O)Nc1ccncc1)N1CCCCO1]

General procedure 1. Starting materials: 4-pyridylamine and ethyl 6-aminohexyl(morpholino)phosphinate (see, e.g., WO 2009/086835).

¹H-NMR (400 MHz, DMSO-d₆): δ 9.76 (bs, 1H), 8.36 (d, 2H), 7.57 (d, 2H), 6.93 (t, 1H), 4.04-3.88 (m, 2H), 3.88-3.81 (m, 2H), 3.29-3.16 (m, 2H), 3.09 (m, 2H), 1.81-1.16 (m, 14H), 1.21 (t, 3H).

Example 87

N-(cyclohexylmethoxy)-N-(2-fluoroethyl)-6-(3-pyridin-4-ylthioureido)hexane-1-sulfonamide (Compound 1087)

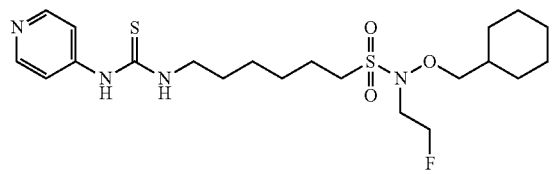 [SMILES: O=C(NCCCCCCS(=O)(=O)N(CCF)OCC1CCCCC1)Nc1ccncc1]

General procedure 3. Starting materials: 4-pyridylamine and 6-amino-N-(cyclohexylmethoxy)-N-(2-fluoroethyl)hexane-1-sulfonamide (see, e.g., WO 2009/086835).

¹H-NMR (CD₃OD): δ 8.35 (m, 2H), 7.72 (m, 2H), 4.62 (dt, 2H), 3.88 (d, 2H), 3.60 (m, 3H), 3.51 (t, 1H), 3.21 (m, 2H), 1.91 (m, 2H), 1.8-1.1 (m, 15H), 1.05 (m, 2H).

Example 88

N-(cyclohexylmethoxy)-N-(2-fluoroethyl)-6-(3-pyridin-4-ylureido)hexane-1-sulfonamide (Compound 1088)

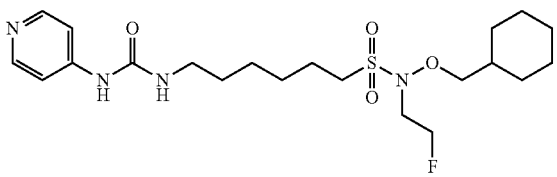

General procedure 1. Starting materials: 4-pyridylamine and 6-amino-N-(cyclohexylmethoxy)-N-(2-fluoroethyl)hexane-1-sulfonamide (see, e.g., WO 2009/086835).

¹H-NMR (CD₃OD): δ 8.27 (m, 2H), 7.46 (m, 2H), 4.61 (dt, 2H), 3.88 (d, 2H), 3.55 (dt, 2H), 3.21 (m, 4H), 1.89 (m, 2H), 1.8-1.1 (m, 15H), 1.03 (m, 2H).

Example 89

N-(cyclohexylmethoxy)-N-(2-fluoroethyl)-6-(3-(pyridin-3-ylmethyl)ureido)hexane-1-sulfonamide (Compound 1089)

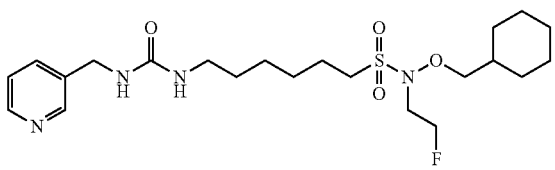 [SMILES: O=C(NCCCCCCS(=O)(=O)N(CCF)OCC1CCCCC1)NCc1cccnc1]

General procedure 2. Starting materials: 3-picolylamine and 6-amino-N-(cyclohexylmethoxy)-N-(2-fluoroethyl)hexane-1-sulfonamide (see, e.g., WO 2009/086835).

¹H-NMR (CD₃OD): δ 8.49 (d, 1H), 8.42 (dd, 1H), 7.79 (dt, 1H), 7.42 (m, 1H), 4.62 (dt, 2H), 4.37 (s, 2H), 3.88 (d, 2H), 3.55 (dt, 2H), 3.17 (m, 4H), 1.95-1.05 (m, 19H).

Example 90

N-Cyclopentyl-N-(2-morpholinoethoxy)-6-(3-(pyridin-4-ylureido)hexane-1-sulfonamide (Compound 1090)

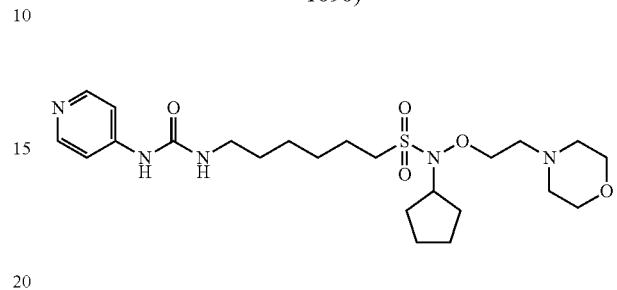

General procedure 1. Starting materials: 4-pyridylamine and 6-amino-N-cyclopentyl-N-(2-morpholinoethoxy)hexane-1-sulfonamide (see, e.g., WO 2009/086835).

¹H-NMR (400 MHz, CDCl₃): δ 8.38 (m, 2H), 7.34 (m, 2H), 7.24 (s, 1H), 5.11 (t, 1H), 4.19 (bs, 2H), 4.01 (m, 1H), 3.71 (t, 4H), 3.28 (m, 2H), 3.09 (bs, 2H), 2.62 (t, 2H), 2.51 (t, 4H), 1.96-1.66 (m, 8H), 1.60-1.46 (m, 6H), 1.39 (m, 2H).

Example 91

N-Cyclopentyl-N-(3-morpholinopropyl)-4-(3-(pyridin-3-ylmethyl)ureido)butane-1-sulfonamide (Compound 1091)

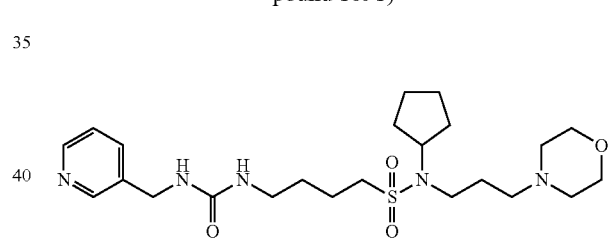

General procedure 2. Starting materials: 3-picolylamine and 4-amino-N-cyclopentyl-N-(3-morpholinopropyl)butane-1-sulfonamide (see, e.g., WO 2009/086835).

¹H-NMR (CD₃OD): δ 8.49 (d, 1H), 8.43 (dd, 1H), 7.79 (dt, 1H), 7.42 (m, 1H), 4.37 (s, 2H), 4.06 (m, 1H), 3.70 (t, 4H), 3.19 (m, 4H), 3.06 (m, 2H), 2.47 (t, 4H), 2.38 (t, 2H), 2.0-1.5 (m, 14H).

Example 92

N-Cyclobutyl-N-(3-morpholinopropyl)-4-(3-(pyridin-3-ylmethyl)ureido)butane-1-sulfonamide (Compound 1092)

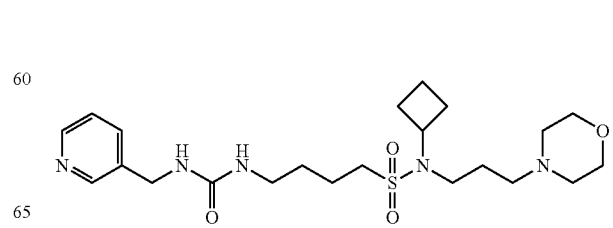

General procedure 2. Starting materials: 3-picolylamine and 4-amino-N-cyclobutyl-N-(3-morpholinopropyl)butane-1-sulfonamide (see, e.g., WO 2009/086835).

¹H-NMR (CD₃OD): δ 8.49 (d, 1H), 8.43 (dd, 1H), 7.79 (dt, 1H), 7.41 (m, 1H), 4.37 (s, 2H), 4.19 (m, 1H), 3.71 (t, 4H), 3.28 (m, 2H), 3.18 (m, 2H), 3.00 (m, 2H), 2.48 (t, 4H), 2.40 (t, 2H), 2.19 (m, 4H), 1.9-1.5 (m, 8H).

Example 93

N-Cyclopentyl-N-(3-morpholinopropyl)-4-(3-pyridin-4-ylthioureido)butane-1-sulfonamide (Compound 1093)

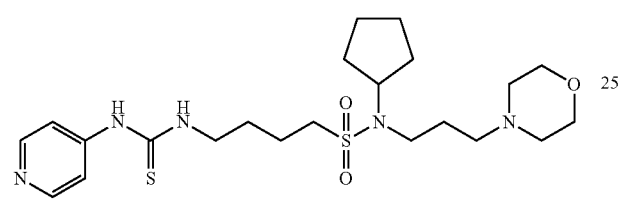

General procedure 3. Starting materials: 4-aminopyridine and 4-amino-N-cyclopentyl-N-(3-morpholinopropyl)butane-1-sulfonamide (see, e.g., WO 2009/086835).

¹H-NMR (CD₃OD): δ 8.37 (m, 2H), 7.73 (m, 2H), 4.08 (m, 1H), 3.70 (m, 6H), 3.17 (m, 4H), 2.47 (t, 4H), 2.39 (t, 2H), 2.0-1.5 (m, 14H).

Example 94

N-Cyclobutyl-N-(3-morpholinopropyl)-4-(3-pyridin-4-ylthioureido)butane-1-sulfonamide (Compound 1094)

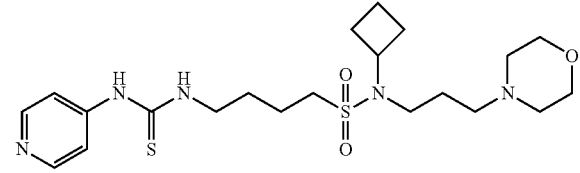 [SMILES: O=S(=O)(CCCCNC(=S)Nc1ccncc1)N(CCCN1CCOCC1)C1CCC1]

General procedure 3. Starting materials: 4-aminopyridine and 4-amino-N-cyclobutyl-N-(3-morpholinopropyl)butane-1-sulfonamide (see, e.g., WO 2009/086835).

¹H-NMR (CD₃OD): δ 8.36 (m, 2H), 7.72 (m, 2H), 4.21 (m, 1H), 3.70 (m, 6H), 3.30 (t, 2H), 3.08 (m, 2H), 2.48 (t, 4H), 2.40 (t, 2H), 2.20 (m, 4H), 1.82 (m, 6H), 1.66 (m, 2H).

Example 95

N-Cyclopentyl-N-(3-morpholinopropyl)-4-(3-(2-(pyridin-3-yl)ethylureido)butane-1-sulfonamide (Compound 1095)

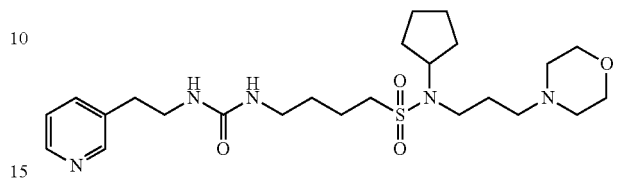

General procedure 2. Starting materials: 2-(pyridin-3-yl)ethanamine and 4-amino-N-cyclopentyl-N-(3-morpholinopropyl)butane-1-sulfonamide (see, e.g., WO 2009/086835).

¹H-NMR (CD₃OD): δ 8.43 (d, 1H), 8.40 (dd, 1H), 7.75 (dt, 1H), 7.40 (m, 1H), 4.07 (m, 1H), 3.69 (m, 4H), 3.39 (t, 2H), 3.17 (m, 4H), 3.06 (m, 2H), 2.84 (t, 2H), 2.46 (t, 4H), 2.38 (t, 2H), 2.0-1.5 (m, 14H).

Example 96

N-Cyclobutyl-N-(3-morpholinopropyl)-4-(3-(2-(pyridin-3-yl)ethylureido)butane-1-sulfonamide (Compound 1096)

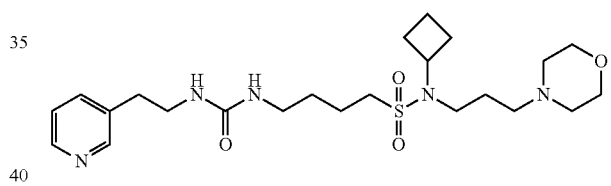

General procedure 2. Starting materials: 2-(pyridin-3-yl)ethanamine and 4-amino-N-cyclobutyl-N-(2-morpholinopropyl)butane-1-sulfonamide (see, e.g., WO 2009/086835).

¹H-NMR (CD₃OD): δ 8.43 (d, 1H), 8.40 (dd, 1H), 7.76 (dt, 1H), 7.40 (m, 1H), 4.21 (m, 1H), 3.70 (m, 4H), 3.40 (t, 2H), 3.30 (t, 2H), 3.14 (t, 2H), 3.00 (m, 2H), 2.84 (t, 2H), 2.47 (t, 4H), 2.41 (t, 2H), 2.21 (m, 4H), 1.9-1.5 (m, 8H).

Example 97

1-(6-(morpholinosulfonyl)hexyl)-3-(pyridin-3-ylmethyl)urea (Compound 1097)

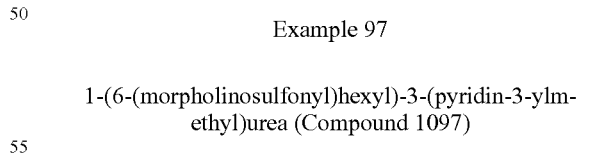

General procedure 2. Starting materials: 3-picolylamine and 6-(morpholinosulfonyl)hexan-1-amine (see, e.g., WO 2009/086835).

¹H-NMR (CD₃OD): δ 8.49 (d, 1H), 8.43 (dd, 1H), 7.79 (dt, 1H), 7.40 (m, 1H), 4.37 (s, 2H), 3.73 (t, 4H), 3.25 (t, 4H), 3.15 (t, 2H), 3.03 (m, 2H), 1.80 (m, 2H), 1.55-1.25 (m, 6H).

Example 98

1-(6-(azepan-1-ylsulfonyl)hexyl)-3-(pyridin-3-ylmethyl)urea (Compound 1098)

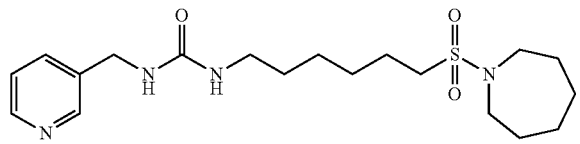 [SMILES: O=C(NCCCCCCS(=O)(=O)N1CCCCCC1)NCc1cccnc1]

General procedure 2. Starting materials: 3-picolylamine and 6-(azepan-1-ylsulfonyl)hexan-1-amine (see, e.g., WO 2009/086835).

¹H-NMR (CD₃OD): δ 8.49 (d, 1H), 8.43 (dd, 1H), 7.79 (dt, 1H), 7.42 (m, 1H), 4.37 (s, 2H), 3.37 (m, 4H), 3.15 (t, 4H), 3.03 (m, 2H), 1.76 (m, 6H), 1.66 (m, 4H), 1.6-1.25 (m, 6H).

Example 99

1-(pyridin-3-ylmethyl)-3-(6-(pyrrolidin-1-ylsulfonyl)hexyl)urea (Compound 1099)

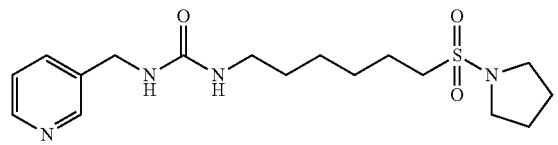 [SMILES: O=C(NCCCCCCS(=O)(=O)N1CCCC1)NCc1cccnc1]

General procedure 2. Starting materials: 3-picolylamine and 6-(pyrrolidin-1-ylsulfonyl)hexan-1-amine (see, e.g., WO 2009/086835).

¹H-NMR (CD₃OD): δ 8.49 (d, 1H), 8.43 (dd, 1H), 7.79 (dt, 1H), 7.42 (m, 1H), 4.37 (s, 2H), 3.34 (m, 4H), 3.15 (t, 4H), 3.06 (m, 2H), 1.95 (m, 4H), 1.79 (m, 2H), 1.6-1.25 (m, 6H).

Example 100

1-(6-(piperidin-1-ylsulfonyl)hexyl)-3-(pyridin-4-yl)thiourea (Compound 1100)

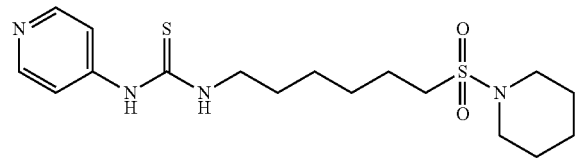 [SMILES: O=S(=O)(CCCCCCNC(=S)Nc1ccncc1)N1CCCCC1]

General procedure 3. Starting materials: 4-aminopyridine and 6-(piperidin-1-ylsulfonyl)hexan-1-amine (see, e.g., WO 2009/086835).

¹H-NMR (CD₃OD): δ 8.35 (m, 2H), 7.73 (m, 2H), 3.62 (t, 2H), 3.24 (m, 4H), 3.01 (m, 2H), 1.82 (m, 2H), 1.8-1.35 (m, 12H).

Example 101

1-(6-(morpholinosulfonyl)hexyl)-3-(pyridin-4-yl)thiourea (Compound 1101)

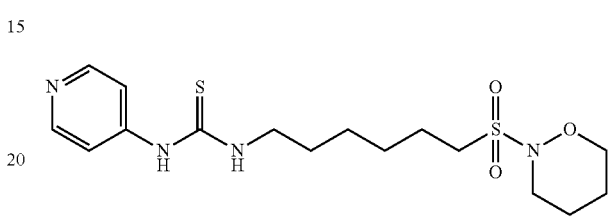

General procedure 3. Starting materials: 4-aminopyridine and 6-(morpholinosulfonyl)hexan-1-amine (see, e.g., WO 2009/086835).

¹H-NMR (CD₃OD): δ 8.35 (m, 2H), 7.72 (m, 2H), 4.11 (t, 2H), 3.62 (t, 2H), 3.37 (t, 2H), 3.22 (m, 2H), 1.88 (m, 4H), 1.71 (m, 4H), 1.52 (m, 4H).

Example 102

In vitro Cell Proliferation Assay (WST-1 Assay)

A2780 cells were seeded in 96-well plates at $3 \times 10^3$ cells/well in 100 μL of culture medium, 8 wells were left empty for media only controls.

After 24 h the compound titrations were performed, in a separate dilution plate, by serially diluting the compounds of general formula (I) in culture medium. A 100 μL of each dilution was added to the plated cells, this was done in triplicate, and controls (e.g. DMSO and blanks) were included. The plates were incubated for 24 h at 37° C. in a $CO_2$ incubator. The compound titrations were repeated in a separate dilution plate after 24 h. The media plus compound from the assay plates were then aspirated. A 100 μL of media was then added to all wells, followed by 100 μL of each compound dilution. The plates were incubated for a further 48 h at 37° C. in a $CO_2$ incubator (total incubation time 72 h). The number of viable cells was then assessed using Cell Proliferation Reagent WST-1. 10 μL of WST-1 reagent added to each well and incubated for one to four hours at 37° C. in $CO_2$ incubator. The absorbance was measured (450 nm/690 nm).

The activity of compounds of general formula (I) in reducing the number of viable cells was calculated as:

$$\% \text{ activity} = [(S^C - B)/(S^O - B)] \times 100$$

$S^C$ denotes signal measured in the presence of test compound, $S^O$ denotes signal detected in the absence of compound, and B denotes background signal, measured in blank wells containing medium only. Analyse data using GraphPad Prism.

Results can be seen in Table 1.

TABLE 1

In vitro cell proliferation assay (WST-1 assay as described in Example 102)

| Compound No. | IC$_{50}$ (nM) for A2780 |
| --- | --- |
| FK866: (APO866, (E)-N-(5-(1-benzoyl-piperidin-4-yl)pentyl)-3-(pyridine-3-yl)-acrylamide) (WO 97/48695) | 0.1 |
| Compound 1001 | 13.5 |
| Compound 1002 | 1.49 |
| Compound 1005 | 0.34 |
| Compound 1007 | 0.98 |
| Compound 1008 | 0.23 |
| Compound 1009 | 0.33 |
| Compound 1013 | 0.11 |
| Compound 1015 | 0.89 |
| Compound 1018 | 14.0 |
| Compound 1020 | 1.34 |
| Compound 1022 | 2.23 |
| Compound 1026 | 0.23 |
| Compound 1031 | 0.13 |
| Compound 1032 | 14.14 |
| Compound 1042 | 6.64 |
| Compound 1043 | 0.37 |
| Compound 1049 | 0.60 |
| Compound 1056 | 0.58 |
| Compound 1058 | 0.63 |
| Compound 1063 | 1.55 |
| Compound 1064 | 0.55 |
| Compound 1065 | 0.22 |
| Compound 1066 | 0.27 |
| Compound 1067 | 0.79 |
| Compound 1069 | 3.04 |
| Compound 1072 | 2.40 |
| Compound 1075 | 1.64 |
| Compound 1076 | 5.40 |
| Compound 1078 | 0.46 |
| Compound 1081 | 0.83 |
| Compound 1082 | 0.053 |
| Compound 1083 | 3.92 |
| Compound 1085 | 6.18 |
| Compound 1087 | 1.36 |
| Compound 1088 | 0.13 |
| Compound 1089 | 2.04 |
| Compound 1090 | 0.15 |

The invention claimed is:

1. A compound of the formula (I)

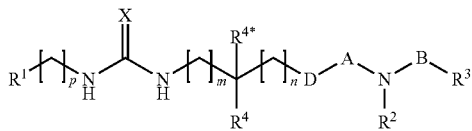

wherein

X is selected from =O and =S;

A is selected from —C(=O)— and —S(=O)$_2$—;

B is selected from —(CH$_2$)$_{3-6}$—, —O—, and —O—(CH$_2$)$_{2-5}$—;

D is selected from a single bond —O—, and —NR$^9$, wherein R$^9$ is selected from hydrogen, optionally substituted C$_{1-12}$-alkyl, optionally substituted C$_{1-12}$-alkenyl, optionally substituted aryl, optionally substituted heterocyclyl, and optionally substituted heteroaryl;

m is an integer of 2-8 and n is 0;

p is an integer of 0-2;

R$^1$ is selected from optionally substituted heteroaryl;

R$^2$ is selected from hydrogen, optionally substituted C$_{3-12}$-cycloalkyl, —[CH$_2$CH$_2$O]$_{1-10}$-(optionally substituted C$_{1-6}$-alkyl), CH$_2$)$_{0-2}$-(optionally substituted aryl), —(CH$_2$)$_{0-2}$-(optionally substituted heteroaryl) and —(CH$_2$)$_{0-2}$-(optionally substituted heterocyclyl); and R$^3$ is selected from optionally substituted C$_{3-12}$-cycloalkyl, —[CH$_2$CH$_2$O]$_{1-10}$-(optionally substituted C$_{1-6}$-alkyl), optionally substituted C$_{1-12}$-alkenyl, optionally substituted aryl, optionally substituted heterocyclyl, and optionally substituted heteroaryl;

R$^4$ is independently selected from hydrogen, optionally substituted C$_{3-12}$-cycloalkyl, —(CH$_2$)$_{0-2}$-(optionally substituted aryl), —(CH$_2$)$_{0-2}$-(optionally substituted heteroaryl) and —(CH$_2$)$_{0-2}$-(optionally substituted heterocyclyl); and R$^{4*}$ is hydrogen;

with the provisos that R$^1$ is not optionally substituted thiazol-2-yl when p is 0;

and with the proviso that the compound is not phenyl-NH—C(=O)—(CH$_2$)$_5$—NH—C(=S)—NH-(4-pyridyl);

and pharmaceutically acceptable salts thereof, and prodrugs thereof.

2. The compound according to claim 1, wherein B is —O—.

3. The compound according to claim 1, wherein D is a single bond.

4. The compound according to claim 1, wherein B is selected from —(CH$_2$)$_{3-6}$— and —O—(CH$_2$)$_{2-5}$—.

5. The compound according to claim 4, wherein A is —S(=O)$_2$—.

6. The compound according to claim 1, wherein R$^1$ is selected from optionally substituted pyridin-4-yl, optionally substituted pyrimidin-4-yl, optionally substituted 1,2,4-triazin-3-yl, optionally substituted isoxazol-4-yl, optionally substituted pyrazin-2-yl, and optionally substituted picolyl.

7. The compound according to claim 1, wherein p is 0 and R$^1$ is pyridine-4-yl.

8. The compound according to claim 1, which is selected from compounds 1001-1101:

| Compound | Structure |
| --- | --- |
| 1001. | 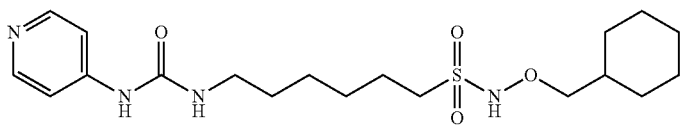 [SMILES: O=C(NCCCCCCS(=O)(=O)NOCC1CCCCC1)Nc1ccncc1] |

| Compound | Structure |
|---|---|
| 1002. | 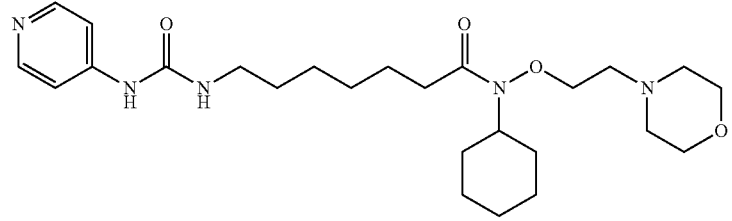 [SMILES: O=C(NCCCCCCC(=O)N(OCCN1CCOCC1)C1CCCCC1)Nc1ccncc1] |
| 1003. | 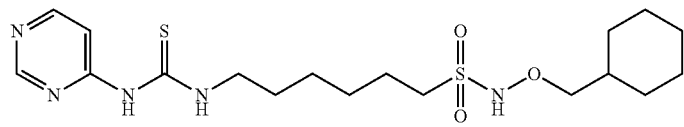 |
| 1004. | 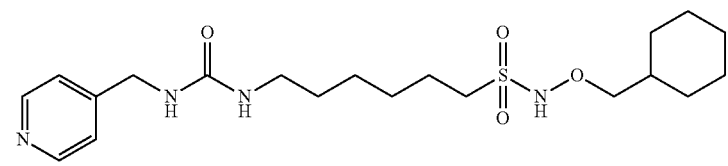 [SMILES: O=C(NCCCCCCS(=O)(=O)NOCC1CCCCC1)NCc1ccncc1] |
| 1005. | 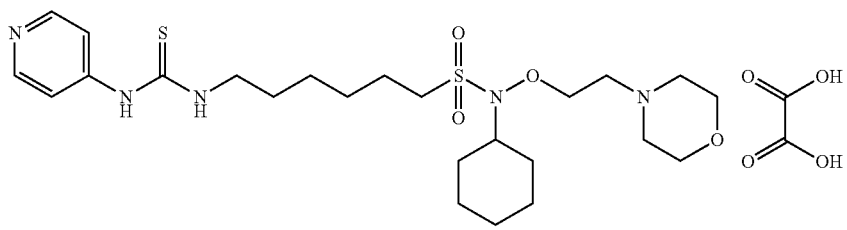 |
| 1006. | 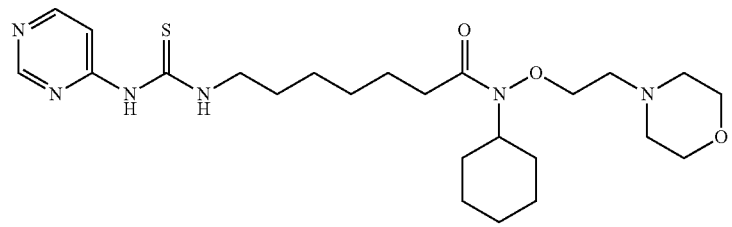 |
| 1007. | 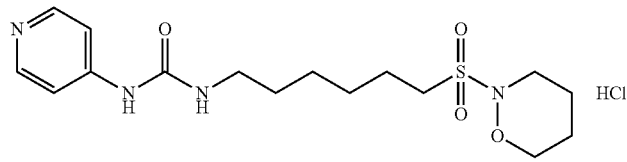 [SMILES: O=C(NCCCCCCS(=O)(=O)N1CCCCO1)Nc1ccncc1 ; Cl] |
| 1008. | 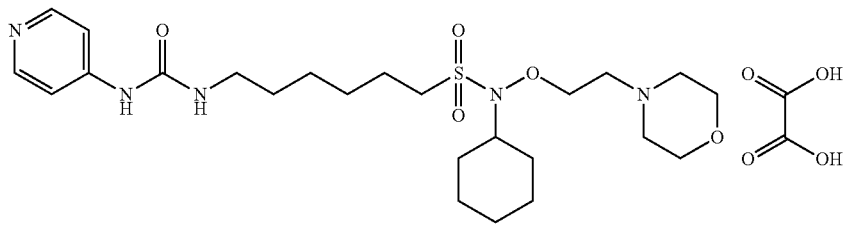 |

-continued
| Compound | Structure |
|---|---|
| 1009. | 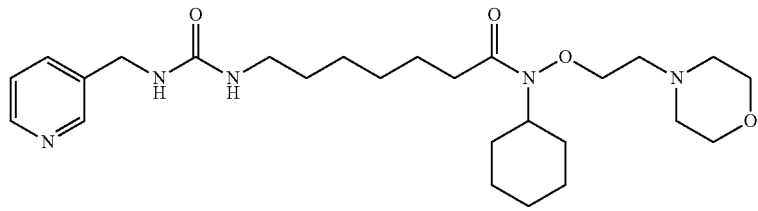 [SMILES: O=C(NCCCCCCC(=O)N(OCCN1CCOCC1)C1CCCCC1)NCc1cccnc1] |
| 1010. | 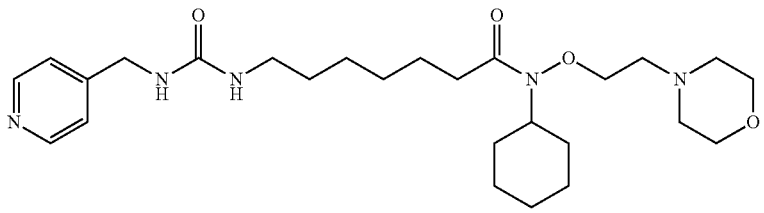 [SMILES: O=C(NCCCCCCC(=O)N(OCCN1CCOCC1)C1CCCCC1)NCc1ccncc1] |
| 1011. | 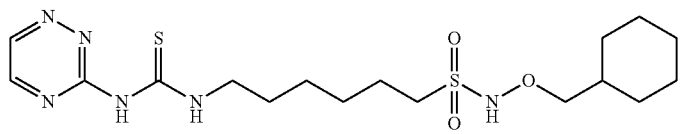 [SMILES: O=S(=O)(CCCCCCNC(=S)Nc1nccnn1)NOCC1CCCCC1] |
| 1012. | 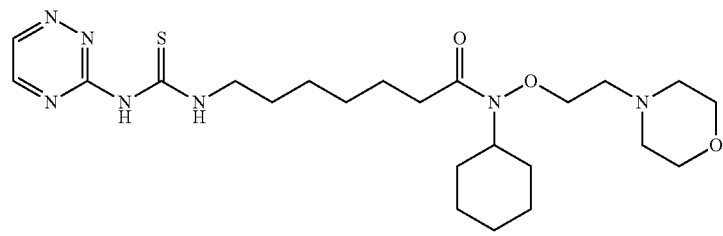 [SMILES: O=C(CCCCCCNC(=S)Nc1nccnn1)N(OCCN1CCOCC1)C1CCCCC1] |
| 1013. | 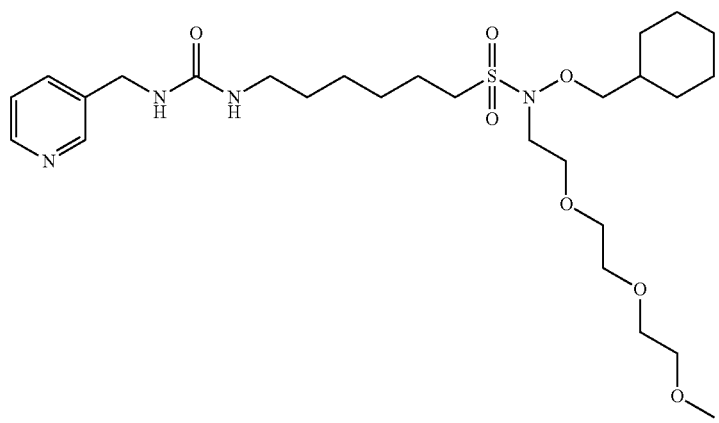 [SMILES: COCCOCCOCCN(OCC1CCCCC1)S(=O)(=O)CCCCCCNC(=O)NCc1cccnc1] |
| 1014. | 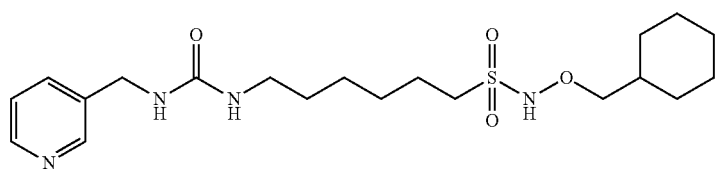 [SMILES: O=C(NCCCCCCS(=O)(=O)NOCC1CCCCC1)NCc1cccnc1] |

-continued
| Compound | Structure |
|---|---|
| 1015. | 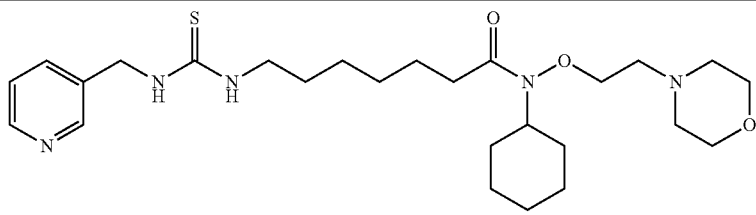 |
| 1016. | 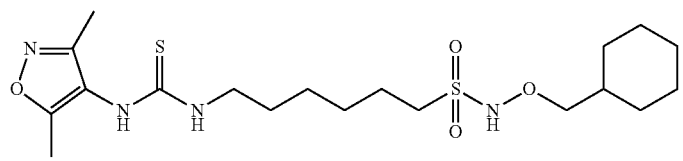 [SMILES: Cc1noc(C)c1NC(=S)NCCCCCCS(=O)(=O)NOCC1CCCCC1] |
| 1017. | 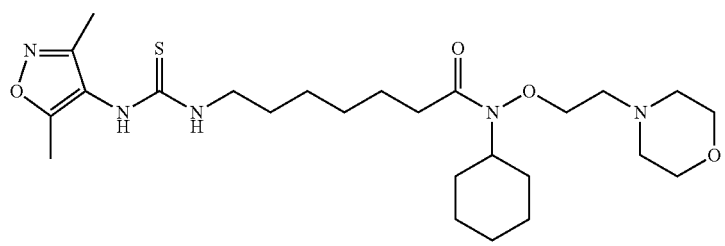 [SMILES: Cc1noc(C)c1NC(=S)NCCCCCCC(=O)N(OCCN1CCOCC1)C1CCCCC1] |
| 1018. | 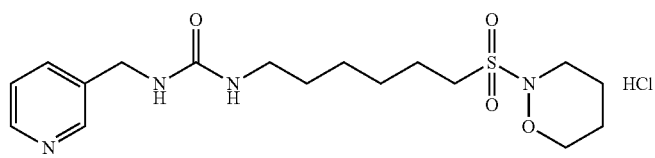 [SMILES: O=C(NCCCCCCS(=O)(=O)N1CCCCO1)NCc1cccnc1 ; Cl] HCl |
| 1019. | 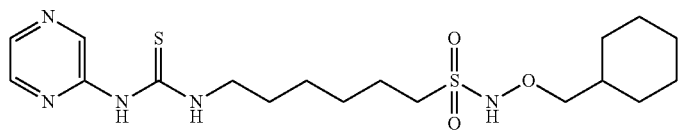 |
| 1020. | 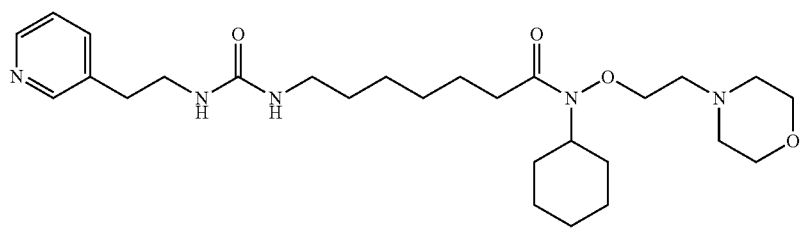 [SMILES: O=C(NCCCCCCC(=O)N(OCCN1CCOCC1)C1CCCCC1)NCCc1cccnc1] |
| 1021. | 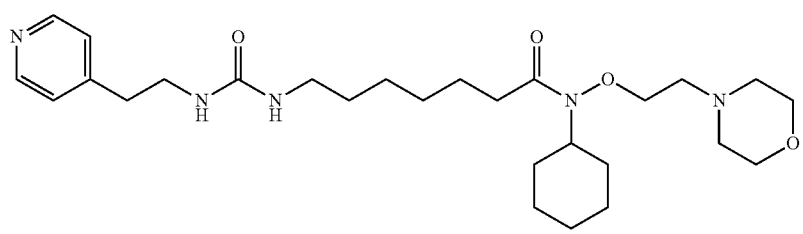 [SMILES: O=C(NCCCCCCC(=O)N(OCCN1CCOCC1)C1CCCCC1)NCCc1ccncc1] |
| 1022. | 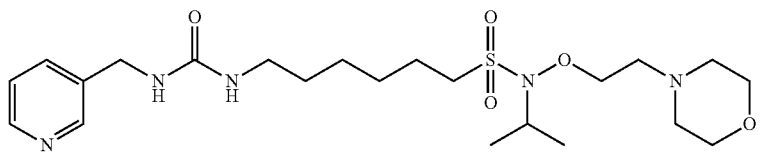 [SMILES: CC(C)N(OCCN1CCOCC1)S(=O)(=O)CCCCCCNC(=O)NCc1cccnc1] |

| Compound | Structure |
|---|---|
| 1023. | 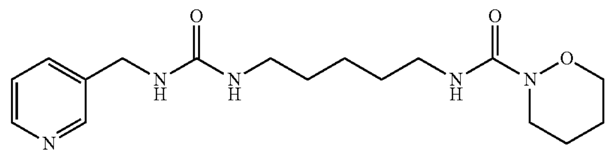 [SMILES: O=C(NCCCCCNC(=O)N1CCCCO1)NCc1cccnc1] |
| 1024. | 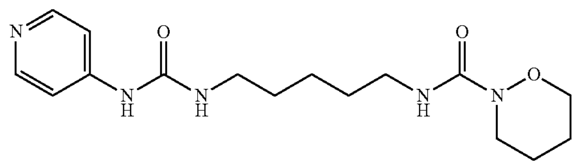 [SMILES: O=C(NCCCCCNC(=O)N1CCCCO1)Nc1ccncc1] |
| 1025. | 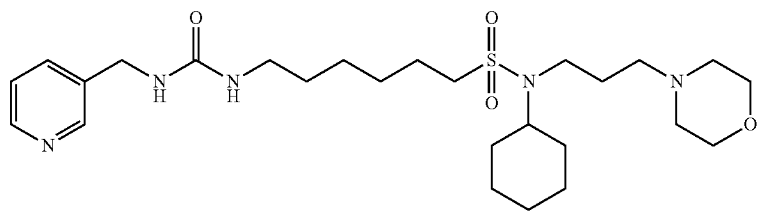 [SMILES: O=C(NCCCCCCS(=O)(=O)N(CCCN1CCOCC1)C1CCCCC1)NCc1cccnc1] |
| 1026. | 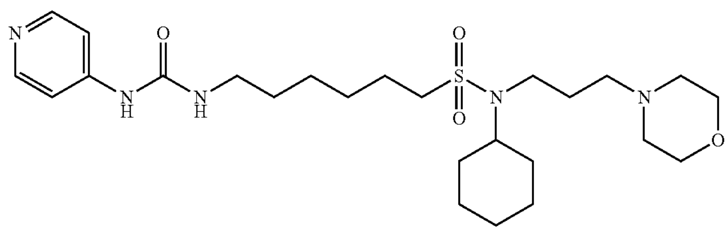 [SMILES: O=C(NCCCCCCS(=O)(=O)N(CCCN1CCOCC1)C1CCCCC1)Nc1ccncc1] |
| 1027. | 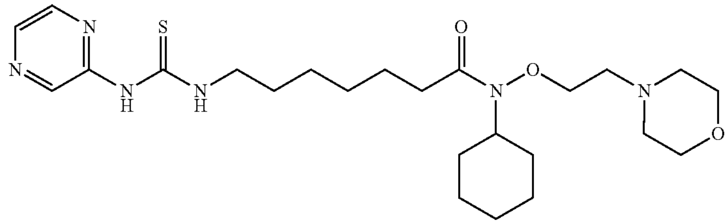 [SMILES: O=C(CCCCCCNC(=S)Nc1cnccn1)N(OCCN1CCOCC1)C1CCCCC1] |
| 1028. | 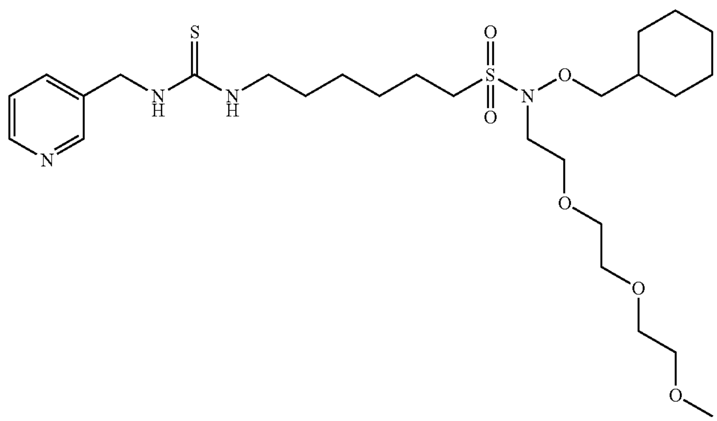 |

| Compound | Structure |
|---|---|
| 1029. | 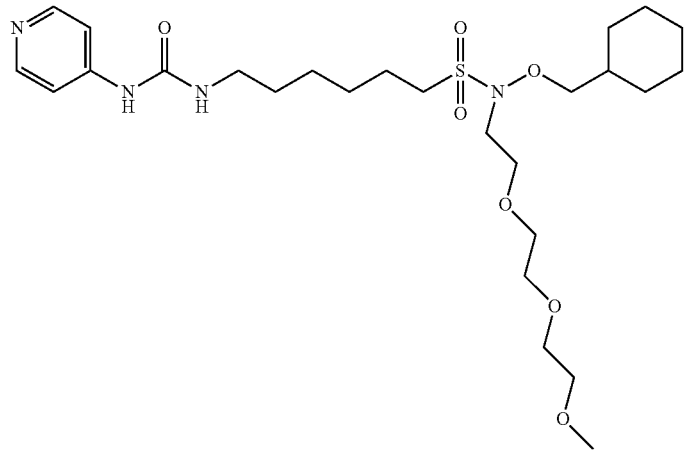 [SMILES: COCCOCCOCCN(OCC1CCCCC1)S(=O)(=O)CCCCCCNC(=O)Nc1ccncc1] |
| 1030. | 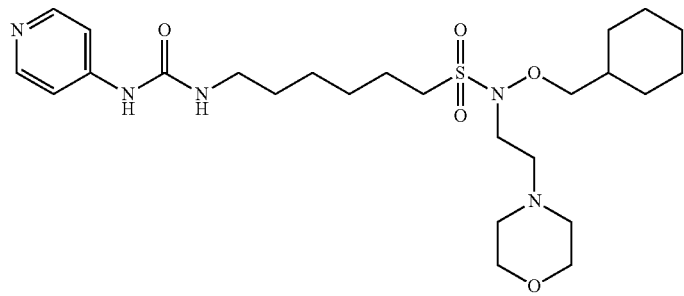 [SMILES: O=C(NCCCCCCS(=O)(=O)N(CCN1CCOCC1)OCC1CCCCC1)Nc1ccncc1] |
| 1031. | 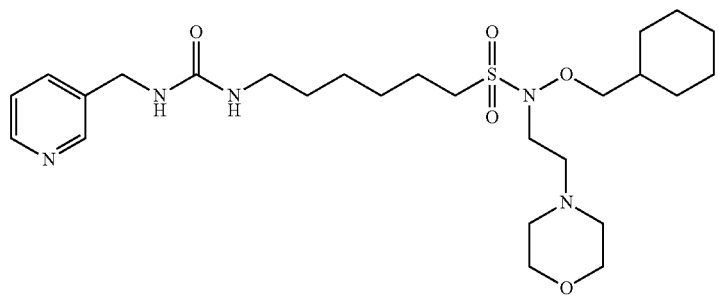 [SMILES: O=C(NCCCCCCS(=O)(=O)N(CCN1CCOCC1)OCC1CCCCC1)NCc1cccnc1] |
| 1032. | 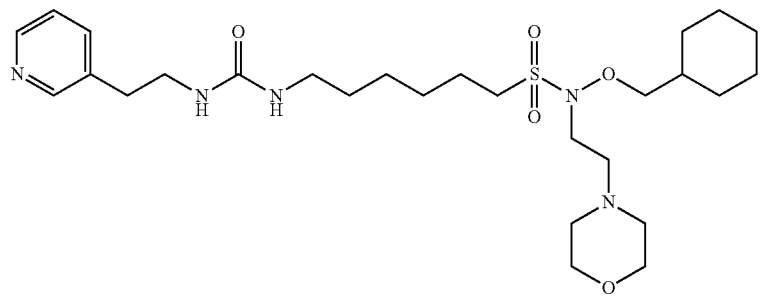 [SMILES: O=C(NCCCCCCS(=O)(=O)N(CCN1CCOCC1)OCC1CCCCC1)NCCc1cccnc1] |
| 1033. | 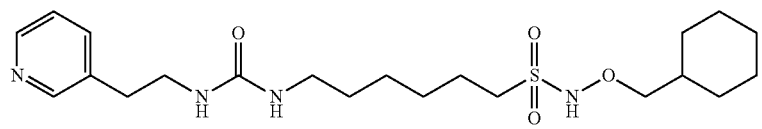 [SMILES: O=C(NCCCCCCS(=O)(=O)NOCC1CCCCC1)NCCc1cccnc1] |

-continued
| Compound | Structure |
|---|---|
| 1034. | 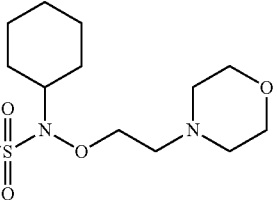 |
| 1035. | 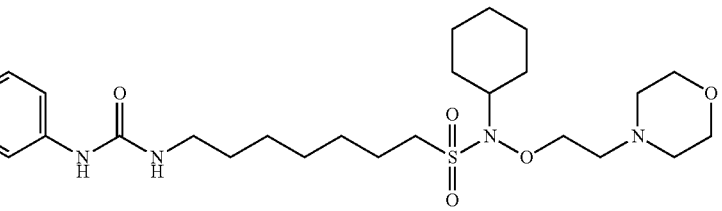 |
| 1036. | 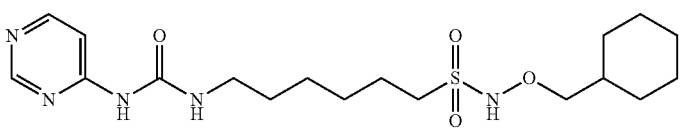 [SMILES: O=C(NCCCCCCS(=O)(=O)NOCC1CCCCC1)Nc1ccncn1] |
| 1037. | 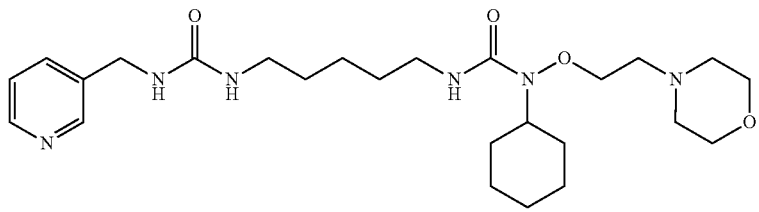 [SMILES: O=C(NCCCCCNC(=O)N(OCCN1CCOCC1)C1CCCCC1)NCc1cccnc1] |
| 1038. | 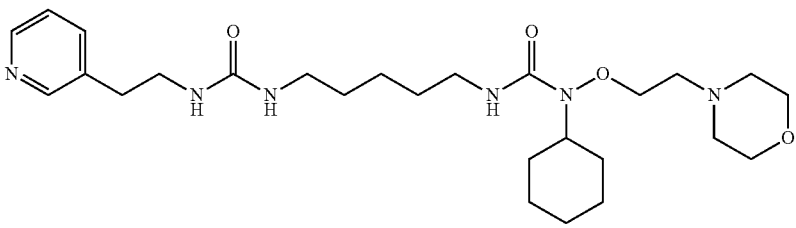 [SMILES: O=C(NCCCCCNC(=O)N(OCCN1CCOCC1)C1CCCCC1)NCCc1cccnc1] |
| 1039. | 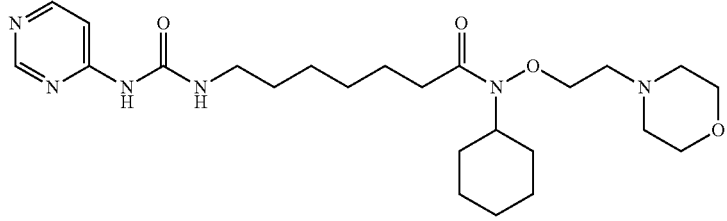 [SMILES: O=C(NCCCCCCC(=O)N(OCCN1CCOCC1)C1CCCCC1)Nc1ccncn1] |
| 1040. | 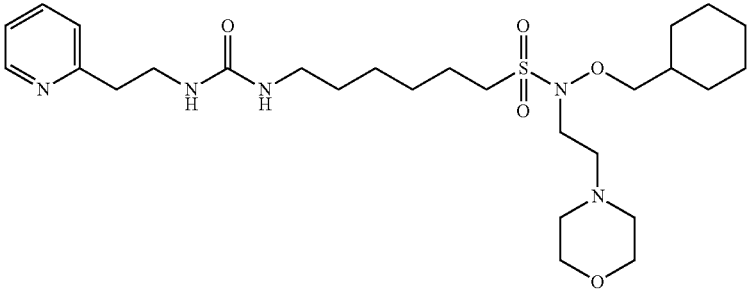 [SMILES: O=C(NCCCCCCS(=O)(=O)N(CCN1CCOCC1)OCC1CCCCC1)NCCc1ccccn1] |

| Compound | Structure |
|---|---|
| 1041. | 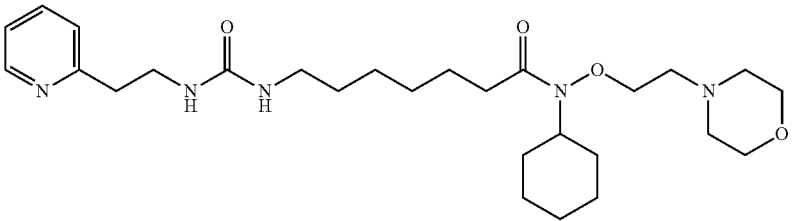 [SMILES: O=C(NCCCCCCC(=O)N(OCCN1CCOCC1)C1CCCCC1)NCCc1ccccn1] |
| 1042. | 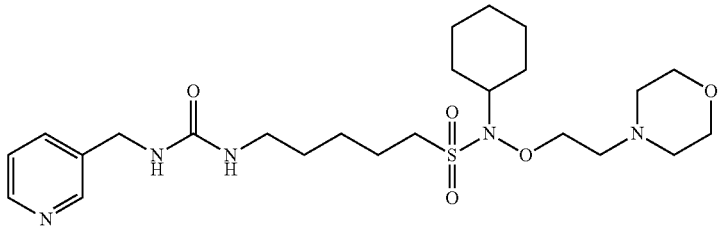 [SMILES: O=C(NCCCCCS(=O)(=O)N(OCCN1CCOCC1)C1CCCCC1)NCc1cccnc1] |
| 1043. | 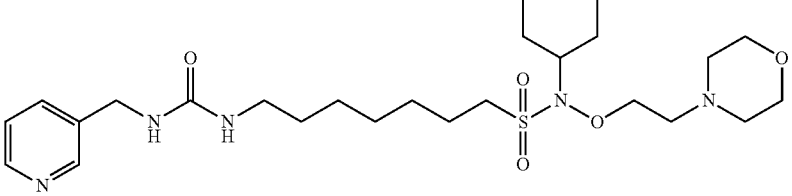 |
| 1044. | 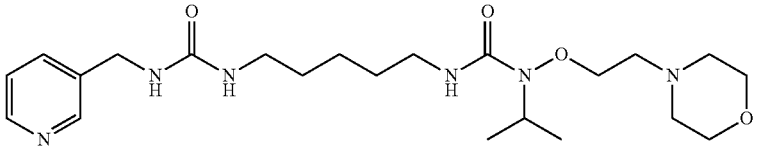 [SMILES: CC(C)N(OCCN1CCOCC1)C(=O)NCCCCCNC(=O)NCc1cccnc1] |
| 1045. | 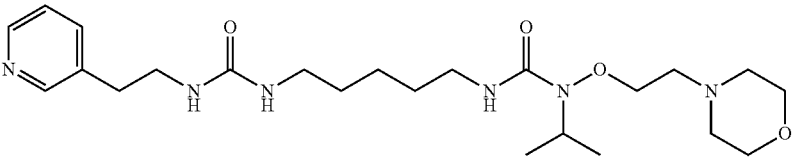 [SMILES: CC(C)N(OCCN1CCOCC1)C(=O)NCCCCCNC(=O)NCCc1cccnc1] |
| 1046. | 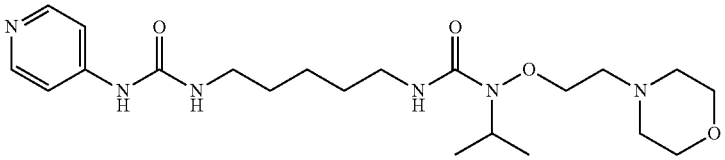 [SMILES: CC(C)N(OCCN1CCOCC1)C(=O)NCCCCCNC(=O)Nc1ccncc1] |
| 1047. | 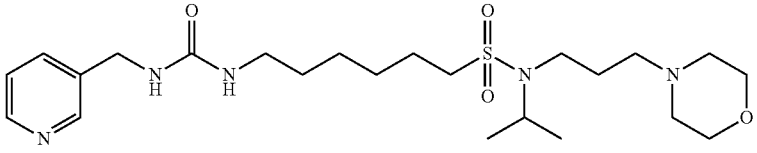 |
| 1048. | 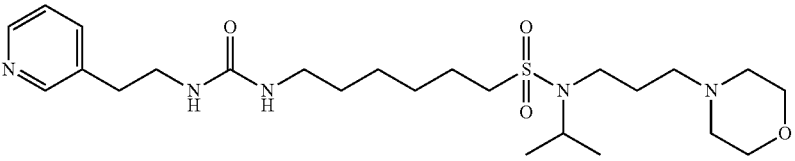 [SMILES: CC(C)N(CCCN1CCOCC1)S(=O)(=O)CCCCCCNC(=O)NCCc1cccnc1] |

| Compound | Structure |
|---|---|
| 1049. | (pyridin-4-yl)-NH-C(=O)-NH-(CH2)5-SO2-N(iPr)-(CH2)3-morpholine |
| 1050. | (pyridin-3-yl)-CH2-NH-C(=O)-NH-(CH2)5-SO2-N(cyclopentyl)-(CH2)3-morpholine |
| 1051. | (pyridin-3-yl)-CH2-NH-C(=O)-NH-(CH2)4-SO2-NH-O-CH2-cyclohexyl |
| 1052. | (pyridin-3-yl)-CH2-NH-C(=O)-NH-(CH2)4-SO2-N(1,2-oxazinane) |
| 1053. | (pyridin-3-yl)-CH2-NH-C(=O)-NH-(CH2)5-SO2-NH-O-CH2-cyclohexyl |
| 1054. | (pyridin-3-yl)-CH2-NH-C(=O)-NH-(CH2)5-SO2-N(1,2-oxazinane) |
| 1055. | (pyridin-2-yl)-CH2-NH-C(=O)-NH-(CH2)5-C(=O)-N(cyclohexyl)-O-CH2CH2-morpholine |
| 1056. | (pyridin-3-yl)-CH2-NH-C(=O)-NH-(CH2)5-SO2-N(cyclopentyl)-O-CH2CH2-morpholine |

| Compound | Structure |
|---|---|
| 1057. | 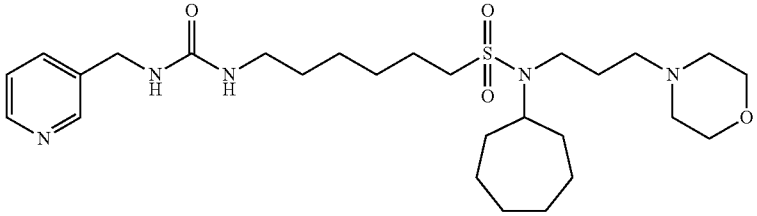 [SMILES: O=C(NCCCCCCS(=O)(=O)N(CCCN1CCOCC1)C1CCCCCC1)NCc1cccnc1] |
| 1058. | 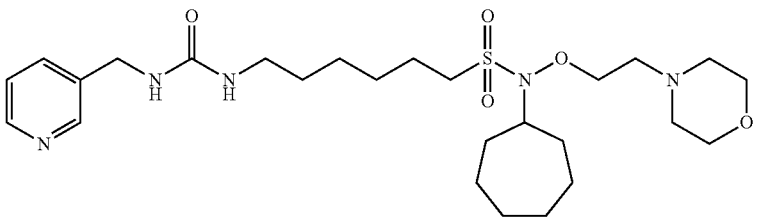 [SMILES: O=C(NCCCCCCS(=O)(=O)N(OCCN1CCOCC1)C1CCCCCC1)NCc1cccnc1] |
| 1059. | 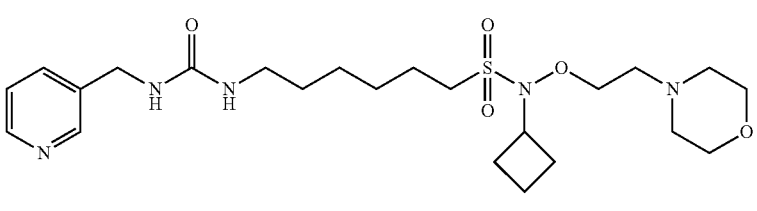 [SMILES: O=C(NCCCCCCS(=O)(=O)N(OCCN1CCOCC1)C1CCC1)NCc1cccnc1] |
| 1060. | 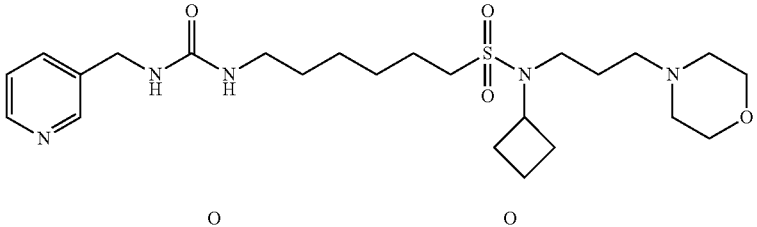 |
| 1061. | 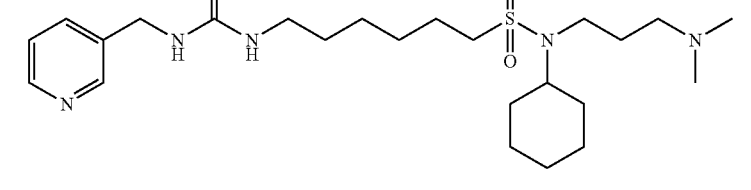 |
| 1062. | 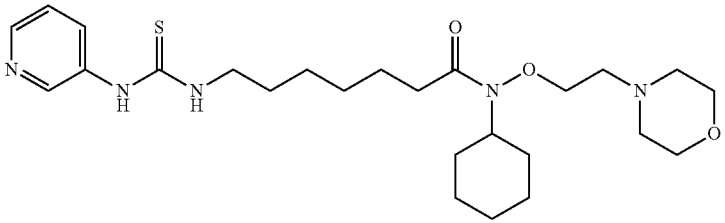 |
| 1063. | 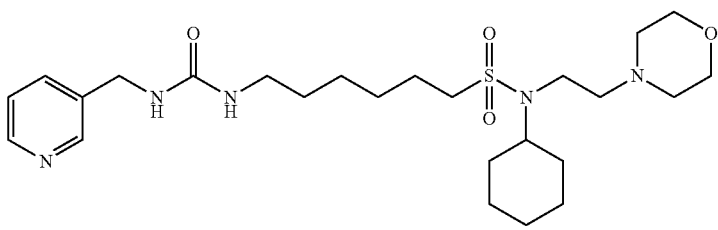 [SMILES: O=C(NCCCCCCS(=O)(=O)N(CCN1CCOCC1)C1CCCCC1)NCc1cccnc1] |

-continued
| Compound | Structure |
|---|---|
| 1064. | 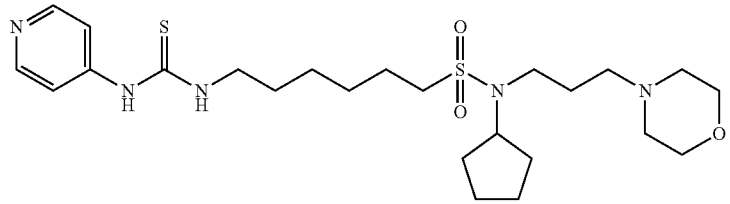 [SMILES: O=S(=O)(CCCCCCNC(=S)Nc1ccncc1)N(CCCN1CCOCC1)C1CCCC1] |
| 1065. | 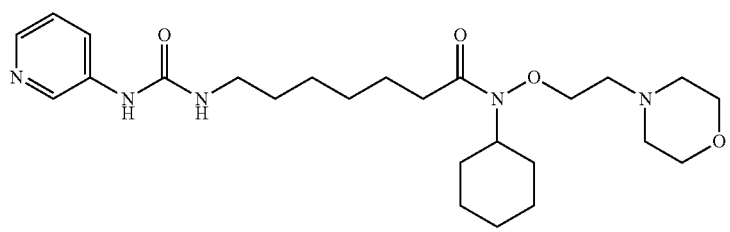 |
| 1066. | 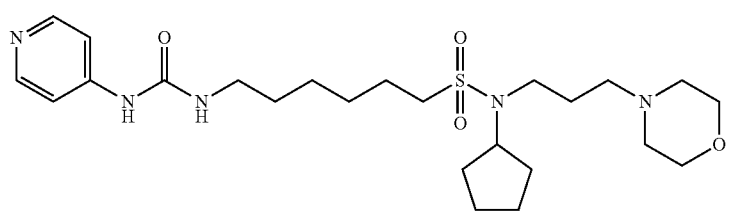 [SMILES: O=C(NCCCCCCS(=O)(=O)N(CCCN1CCOCC1)C1CCCC1)Nc1ccncc1] |
| 1067. | 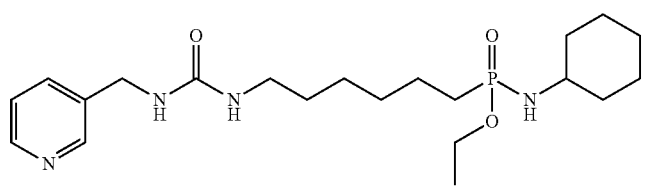 [SMILES: CCOP(=O)(CCCCCCNC(=O)NCc1cccnc1)NC1CCCCC1] |
| 1068. | 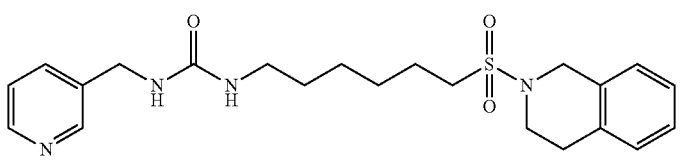 [SMILES: O=C(NCCCCCCS(=O)(=O)N1CCc2ccccc2C1)NCc1cccnc1] |
| 1069. | 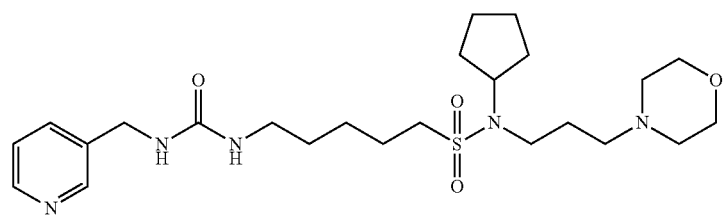 [SMILES: O=C(NCCCCCS(=O)(=O)N(CCCN1CCOCC1)C1CCCC1)NCc1cccnc1] |
| 1070. | 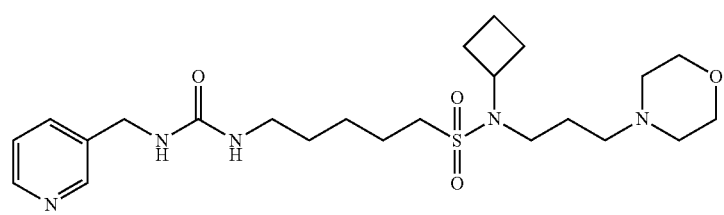 [SMILES: O=C(NCCCCCS(=O)(=O)N(CCCN1CCOCC1)C1CCC1)NCc1cccnc1] |

| Compound | Structure |
|---|---|
| 1071. | 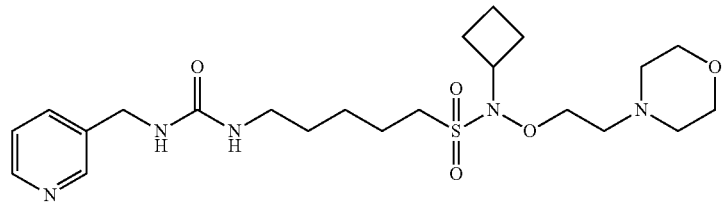 |
| 1072. | 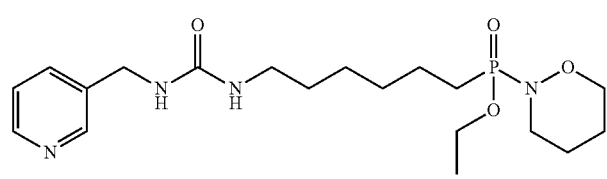 [SMILES: CCOP(=O)(CCCCCCNC(=O)NCc1cccnc1)N1CCCCO1] |
| 1073. | 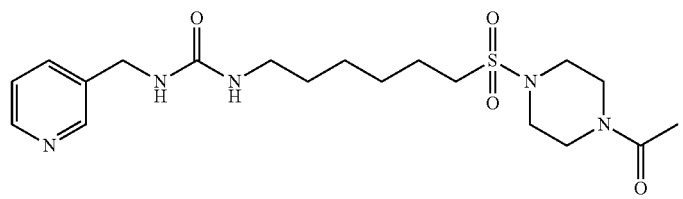 [SMILES: CC(=O)N1CCN(S(=O)(=O)CCCCCCNC(=O)NCc2cccnc2)CC1] |
| 1074. | 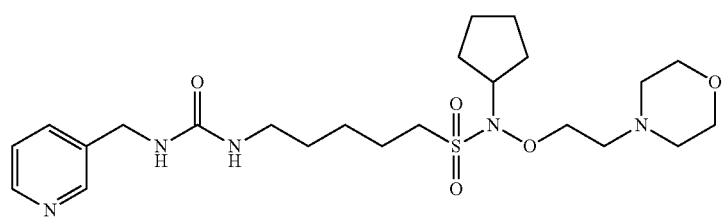 |
| 1075. | 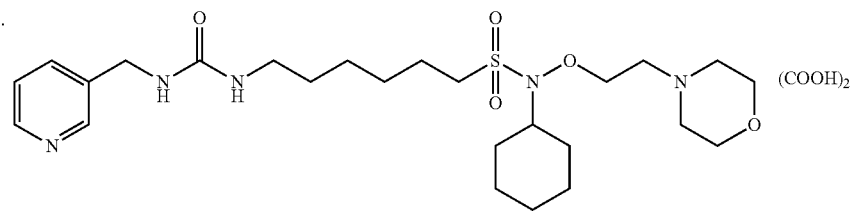 (COOH)$_2$ |
| 1076. | 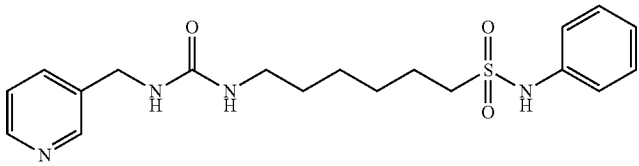 [SMILES: O=C(NCCCCCCS(=O)(=O)Nc1ccccc1)NCc1cccnc1] |
| 1077. | 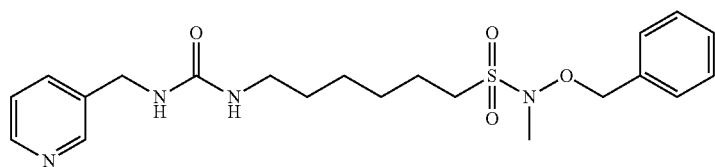 [SMILES: CN(OCc1ccccc1)S(=O)(=O)CCCCCCNC(=O)NCc1cccnc1] |

| Compound | Structure |
|---|---|
| 1078. | 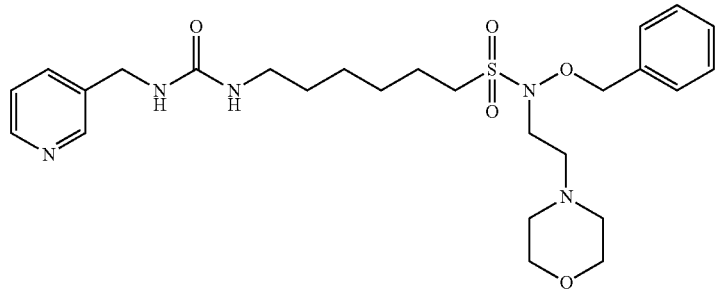 [SMILES: O=C(NCCCCCCS(=O)(=O)N(CCN1CCOCC1)OCc1ccccc1)NCc1cccnc1] |
| 1079. | 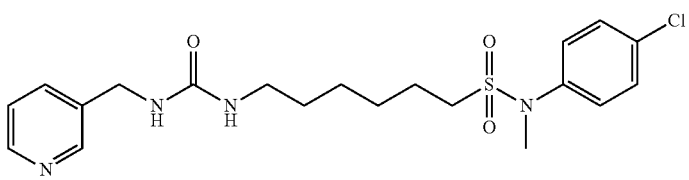 [SMILES: CN(c1ccc(Cl)cc1)S(=O)(=O)CCCCCCNC(=O)NCc1cccnc1] |
| 1080. | 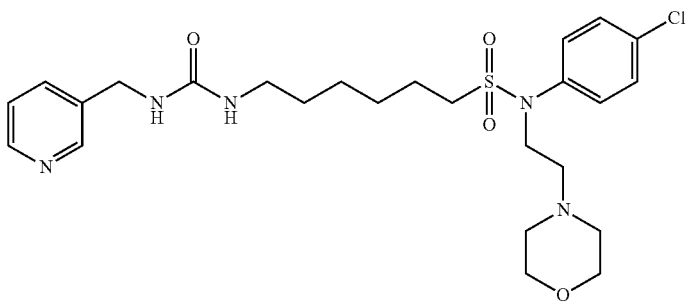 [SMILES: O=C(NCCCCCCS(=O)(=O)N(CCN1CCOCC1)c1ccc(Cl)cc1)NCc1cccnc1] |
| 1081. | 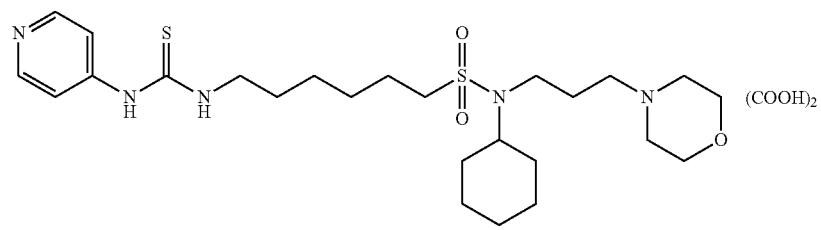 [SMILES: O=S(=O)(CCCCCCNC(=S)Nc1ccncc1)N(CCCN1CCOCC1)C1CCCCC1 ; "(COOH)2"] |
| 1082. | 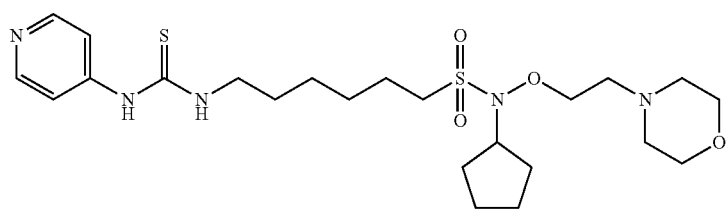 |
| 1083. | 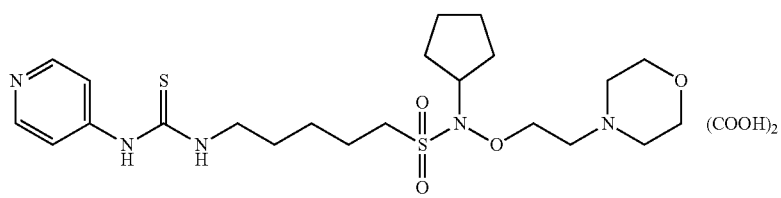 |

| Compound | Structure |
|---|---|
| 1084. | 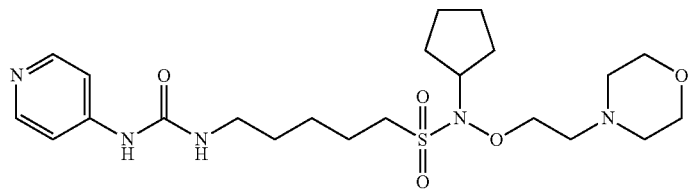 [SMILES: O=C(NCCCCCS(=O)(=O)N(OCCN1CCOCC1)C1CCCC1)Nc1ccncc1] |
| 1085. | 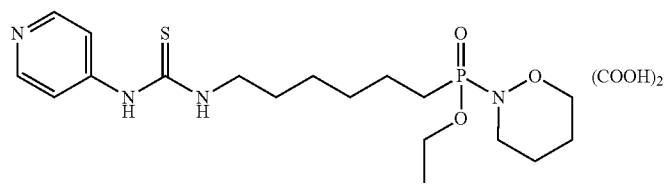 |
| 1086. | 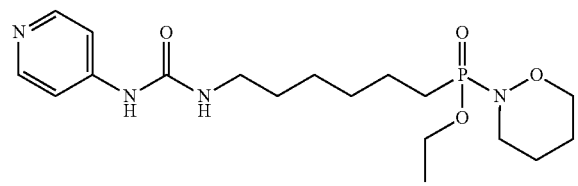 [SMILES: CCOP(=O)(CCCCCCNC(=O)Nc1ccncc1)N1CCCCO1] |
| 1087. | 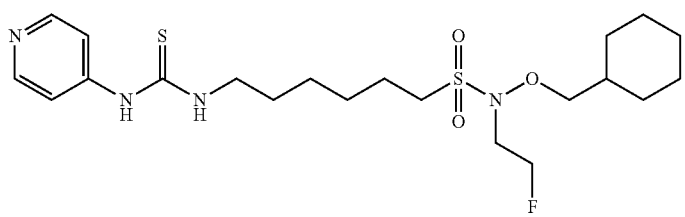 [SMILES: O=S(=O)(CCCCCCNC(=S)Nc1ccncc1)N(CCF)OCC1CCCCC1] |
| 1088. | 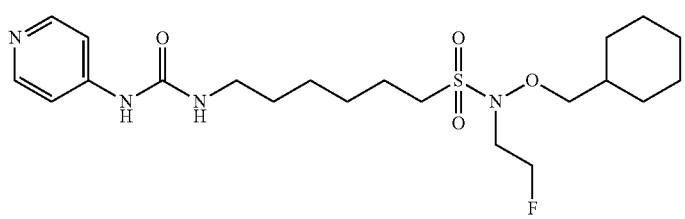 [SMILES: O=C(NCCCCCCS(=O)(=O)N(CCF)OCC1CCCCC1)Nc1ccncc1] |
| 1089. | 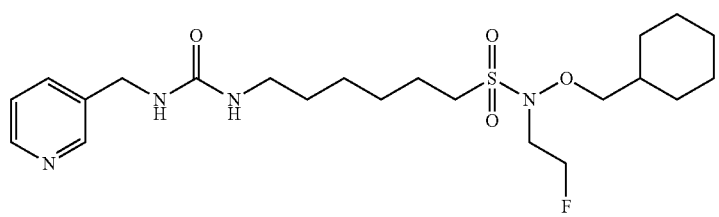 [SMILES: O=C(NCCCCCCS(=O)(=O)N(CCF)OCC1CCCCC1)NCc1cccnc1] |
| 1090. | 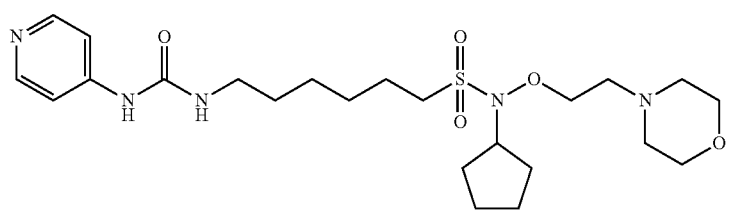 |

| Compound | Structure |
|---|---|
| 1091. | 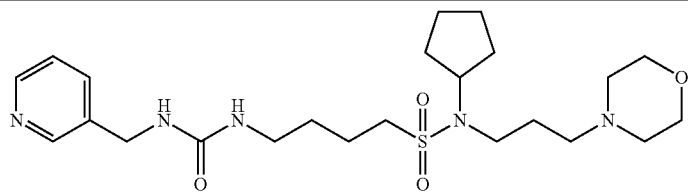 |
| 1092. | 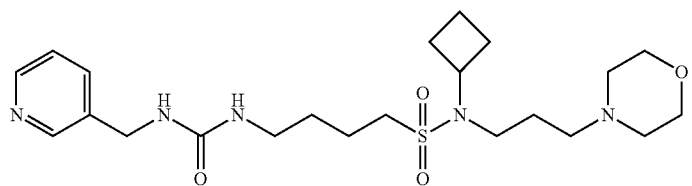 [SMILES: O=C(NCCCCS(=O)(=O)N(CCCN1CCOCC1)C1CCC1)NCc1cccnc1] |
| 1093. | 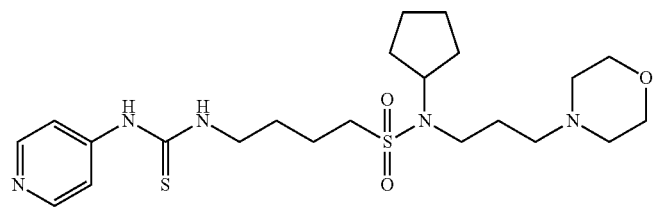 [SMILES: O=S(=O)(CCCCNC(=S)Nc1ccncc1)N(CCCN1CCOCC1)C1CCCC1] |
| 1094. | 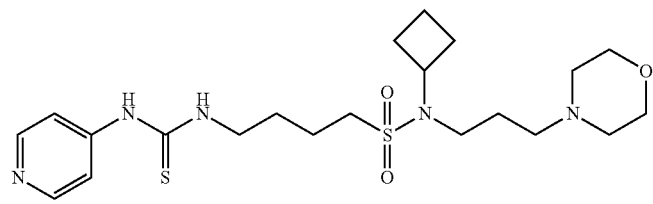 [SMILES: O=S(=O)(CCCCNC(=S)Nc1ccncc1)N(CCCN1CCOCC1)C1CCC1] |
| 1095. | 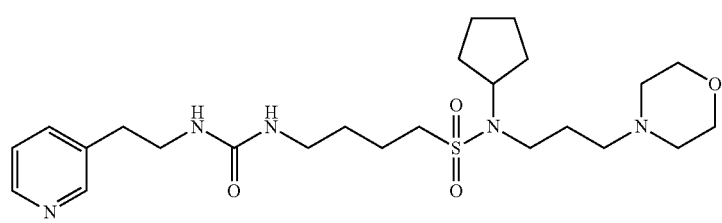 [SMILES: O=C(NCCCCS(=O)(=O)N(CCCN1CCOCC1)C1CCCC1)NCCc1cccnc1] |
| 1096. | 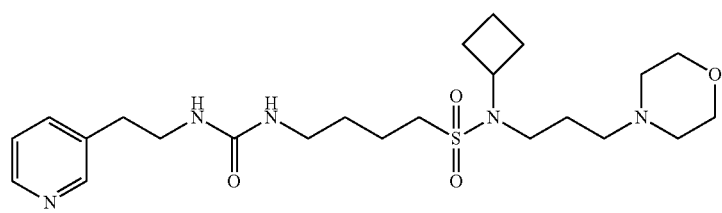 [SMILES: O=C(NCCCCS(=O)(=O)N(CCCN1CCOCC1)C1CCC1)NCCc1cccnc1] |
| 1097. | 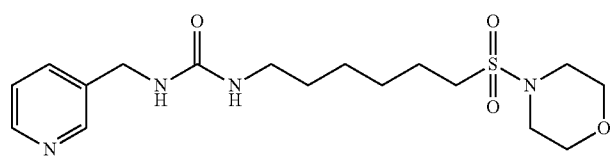 [SMILES: O=C(NCCCCCCS(=O)(=O)N1CCOCC1)NCc1cccnc1] |
| 1098. | 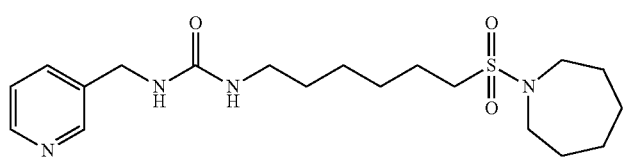 [SMILES: O=C(NCCCCCCS(=O)(=O)N1CCCCCC1)NCc1cccnc1] |

| Compound | Structure |
|---|---|
| 1099. | 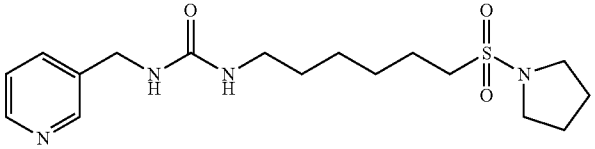 [SMILES: O=C(NCCCCCCS(=O)(=O)N1CCCC1)NCc1cccnc1] |
| 1100. | 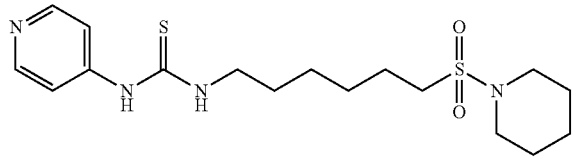 [SMILES: O=S(=O)(CCCCCCNC(=S)Nc1ccncc1)N1CCCCC1] |
| 1101. | 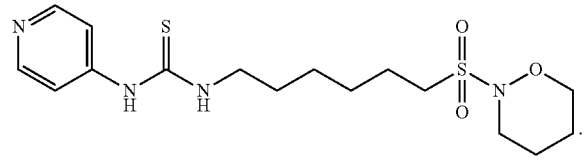 [SMILES: O=S(=O)(CCCCCCNC(=S)Nc1ccncc1)N1CCCCO1 ; "."] |
* * * * *